United States Patent
Utsumi et al.

(10) Patent No.: US 8,846,291 B2
(45) Date of Patent: Sep. 30, 2014

(54) RESIST COMPOSITION, METHOD OF FORMING RESIST PATTERN, AND NEW COMPOUND

(75) Inventors: Yoshiyuki Utsumi, Kawasaki (JP); Kenichiro Miyashita, Kawasaki (JP); Akiya Kawaue, Kawasaki (JP)

(73) Assignee: Tokyo Ohka Kogyo Co. Ltd., Kawasaki-shi (JP)

( * ) Notice: Subject to any disclaimer, the term of this patent is extended or adjusted under 35 U.S.C. 154(b) by 0 days.

(21) Appl. No.: 13/312,013

(22) Filed: Dec. 6, 2011

(65) Prior Publication Data
US 2012/0148955 A1 Jun. 14, 2012

(30) Foreign Application Priority Data

Dec. 8, 2010 (JP) .................. P2010-273831

(51) Int. Cl.
| | | |
|---|---|---|
| G03F 7/004 | (2006.01) | |
| C07C 303/32 | (2006.01) | |
| C07C 309/07 | (2006.01) | |
| C07D 213/79 | (2006.01) | |
| C07D 213/80 | (2006.01) | |
| C07D 215/48 | (2006.01) | |
| C07D 215/50 | (2006.01) | |
| C07D 215/54 | (2006.01) | |
| C07D 219/04 | (2006.01) | |
| C07D 221/10 | (2006.01) | |
| G03F 7/039 | (2006.01) | |

(52) U.S. Cl.
CPC ............ *C07D 213/79* (2013.01); *C07D 213/80* (2013.01); *C07D 215/48* (2013.01); *C07D 215/50* (2013.01); *C07D 215/54* (2013.01); *C07D 219/04* (2013.01); *C07D 221/10* (2013.01); *G03F 7/0045* (2013.01); *G03F 7/0046* (2013.01); *G03F 7/039* (2013.01); *G03F 7/0397* (2013.01); *Y10S 430/121* (2013.01); *Y10S 430/122* (2013.01); *Y10S 430/123* (2013.01)
USPC ........ 430/270.1; 430/326; 430/920; 430/921; 430/922; 546/326; 562/109; 562/113

(58) Field of Classification Search
CPC ... G03F 7/0045; G03F 7/0392; G03F 7/0046; G03F 7/039; G03F 7/0397; C07C 303/32; C07C 309/07; C07D 213/79; C07D 213/80; C07D 215/48; C07D 215/50; C07D 215/54; C07D 219/04; C07D 221/10
USPC .............. 430/270.1, 326, 910, 920, 921, 922; 546/326; 562/109, 113
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,949,325 B2 | 9/2005 | Li et al. | |
| 7,074,543 B2 | 7/2006 | Iwai et al. | |
| 7,524,609 B2 * | 4/2009 | Wada .................. | 430/270.1 |
| 8,236,842 B2 * | 8/2012 | Yoshida et al. ........... | 514/397 |
| 2001/0049073 A1 | 12/2001 | Hada et al. | |
| 2011/0171576 A1 * | 7/2011 | Yamaguchi et al. ....... | 430/270.1 |
| 2011/0201823 A1 * | 8/2011 | Yoshida et al. ........... | 548/334.1 |
| 2011/0217654 A1 * | 9/2011 | Yamato et al. ............ | 430/270.1 |
| 2011/0318688 A1 * | 12/2011 | Hiraoka et al. ........... | 430/270.1 |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2009-209128 | 9/2009 |
| WO | WO 2004/074242 A2 | 9/2004 |

* cited by examiner

*Primary Examiner* — John Chu
(74) *Attorney, Agent, or Firm* — Knobbe Martens Olson & Bear LLP

(57) ABSTRACT

A resist composition including: a base component (A) which exhibits changed solubility in a developing solution under action of acid; a nitrogen-containing organic compound component (C) containing a compound (C1) represented by general formula (c1) shown below; and an acid generator component (B) which generates acid upon exposure, provided that the compound (C1) is excluded from the acid generator component (B):

[Chemical Formula 1]

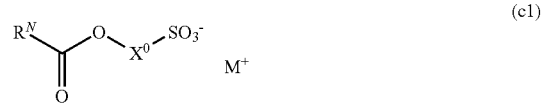

(c1)

wherein $R^N$ represents a nitrogen-containing heterocyclic group which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $M^+$ represents an organic cation.

12 Claims, No Drawings

RESIST COMPOSITION, METHOD OF FORMING RESIST PATTERN, AND NEW COMPOUND

BACKGROUND OF THE INVENTION

1. Field of the Invention

The present invention relates to a resist composition, a method of forming a resist pattern using the resist composition, and a novel compound useful as a quencher for the resist composition.

Priority is claimed on Japanese Patent Application No. 2010-273831, filed Dec. 8, 2010, the content of which is incorporated herein by reference.

2. Description of Related Art

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base material component that exhibits a changed solubility in an alkali developing solution under the action of acid and an acid generator component that generates acid upon exposure.

For example, as a chemically amplified positive resist composition, a chemically amplified resist composition is used, which includes a resin component (base resin) that exhibits increased solubility in an alkali developing solution under the action of acid, and an acid generator component. If the resist film formed using the resist composition is selectively exposed during formation of a resist pattern, then within the exposed portions, acid is generated from the acid generator component, and the action of this acid causes an increase in the solubility of the resin component in an alkali developing solution, making the exposed portions soluble in the alkali developing solution.

Currently, resins that contain structural units derived from (meth)acrylate esters within the main chain (acrylic resins) are now typically used as base resins for resists that use ArF excimer laser lithography, as they exhibit excellent transparency in the vicinity of 193 nm (for example, see Patent Document 1).

As acid generators usable in a chemically amplified resist composition, various types have been proposed including, for example, onium salt acid generators such as iodonium salts and sulfonium salts; oxime sulfonate acid generators; diazomethane acid generators; nitrobenzylsulfonate acid generators; iminosulfonate acid generators; and disulfone acid generators.

Furthermore, currently, in addition to the base resin and the acid generator, a nitrogen-containing organic compound such as an alkylamine, an alkylalcoholamine or the like is added to chemically amplified resist compositions. The nitrogen-containing organic compound functions as a quencher which traps the acid generated from the acid generator, and contributes to improving various lithography properties.

In recent years, as quenchers, studies have been made on photodegradable bases which are decomposed by light or radiation. The photodegradable bases included in the resist composition are those in which the unexposed portions function as a quencher whereas the exposed portions lose the quenching capacity due to decomposition of the nitrogen-containing organic compound itself, thereby maintaining, without reducing too much, the acid concentration within the exposed portions to an adequate level.

DOCUMENTS OF RELATED ART

Patent Documents

[Patent Document 1] Japanese Unexamined Patent Application, First Publication No. 2003-241385
[Patent Document 2] Japanese Unexamined Patent Application, First Publication No. 2009-209128

SUMMARY OF THE INVENTION

As the miniaturization of resist pattern progresses, for example, lithography using electron beam or EUV is aiming the formation of a fine pattern having a size of several tens of nanometers. As the size of the resist pattern becomes smaller, further improvement in the resolution of resist materials has been demanded while maintaining excellent lithography properties and capability of forming a resist pattern with excellent shape.

In order to meet such demands, there is a resist composition having an acid generator, which has been described in Patent Document 2, as a resist composition with improved lithography properties and resist pattern shape. Since the acid generator described in Patent Document 2 includes an organic group having a nitrogen atom in the anion moiety, it is excellent from the viewpoint of also functioning as a quencher for deactivating the acid generated from the acid generator. Because the organic group having a nitrogen atom is included by binding to the anion moiety, compatibility with the acid generator is improved, and the distribution of the organic group having a nitrogen atom within the resist film becomes more uniform, thereby suppressing the bias in the organic group distribution and the acid generator distribution.

However, in those cases where an acid generator as described in Patent Document 2 has been used, there was still room for improvement in terms of the lithography properties and resist pattern shape of the obtained resist pattern.

The present invention takes the above circumstances into consideration, with an object of providing a compound useful as a quencher for resist compositions, a resist composition that contains the quencher, and a method of forming a resist pattern that uses the resist composition.

For solving the above-mentioned problems, the present invention employs the following aspects.

Specifically, a first aspect of the present invention is a resist composition including a base component (A) which exhibits changed solubility in a developing solution under action of acid, a nitrogen-containing organic compound component (C) containing a compound (C1) represented by general formula (c1) shown below and an acid generator component (B) which generates acid upon exposure, provided that the compound (C1) is excluded from the acid generator component (B).

[Chemical Formula 1]

(c1)

In the formula, $R^N$ represents a nitrogen-containing heterocyclic group which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $M^+$ represents an organic cation.

A second aspect of the present invention is a method of forming a resist pattern, including: applying a resist composition of the first aspect to a substrate to form a resist film on the substrate; conducting exposure of the resist film; and developing the resist film to form a resist pattern.

A third aspect of the present invention is a compound represented by general formula (c1') shown below.

[Chemical Formula 2]

(c1')

In the formula, $R^N$ represents a nitrogen-containing heterocyclic group which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $Z^+$ represents an organic cation or a metal cation.

In the present description and claims, an "alkyl group" includes linear, branched or cyclic, monovalent saturated hydrocarbon groups, unless otherwise specified.

The term "alkylene group" includes linear, branched or cyclic divalent saturated hydrocarbon groups, unless otherwise specified.

A "lower alkyl group" is an alkyl group of 1 to 5 carbon atoms.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a polymeric compound (namely, a polymer or copolymer).

The term "exposure" is used as a general concept that includes irradiation with any form of radiation.

The term "(meth)acrylic acid" is a generic term that includes either or both of acrylic acid having a hydrogen atom bonded to the α-position and methacrylic acid having a methyl group bonded to the α-position.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

According to the present invention, there are provided a novel compound preferable as an acid generator for a resist composition, an acid generator including the compound, a resist composition including the acid generator, and a method of forming a resist pattern using the resist composition.

DETAILED DESCRIPTION OF THE INVENTION

Resist Composition

The resist composition according to a first aspect of the present invention includes a base component (A) (hereafter, referred to as "component (A)") which exhibits changed solubility in a developing solution under the action of acid, a nitrogen-containing organic compound component (C) (hereafter, referred to as "component (C)") containing a compound (C1) represented by general formula (c1) shown below and an acid generator component (B) (hereafter, referred to as "component (B)") which generates acid upon exposure, provided that the compound (C1) is excluded from the acid generator component (B).

If the resist film formed using this resist composition is selectively exposed, acid is generated from the component (B) or the compound (C1) within the exposed portions, and the action of this acid causes a change in the solubility of the component (A) in a developing solution, whereas the solubility of the component (A) in the developing solution remains unchanged in the unexposed portions. Accordingly, a difference in the solubility in a developing solution is developed between the exposed portions and the unexposed portions. Therefore, by developing this resist film using an alkali developing solution to be described later, the exposed portions are dissolved and removed in the case of a positive resist composition, whereas the unexposed portions are dissolved and removed in the case of a negative resist composition, and hence, a resist pattern can be formed.

In the present description, a resist composition for forming a positive resist pattern will be referred to as a positive resist composition, and a resist composition for forming a negative resist pattern will be referred to as a negative resist composition.

The resist composition of the present invention may be a resist composition for an alkali developing process that uses an alkali developing solution for developing during the resist pattern formation, or may be a resist composition for a solvent developing process (also referred to as "negative developing process") that uses a developing solution containing an organic solvent (organic developing solution) for the developing.

<Component (A)>

The component (A) is a base component that exhibits changed solubility in a developing solution under the action of acid.

In the present description and claims, the term "base component" refers to an organic compound capable of forming a film, and is preferably an organic compound having a molecular weight of 500 or more. When the organic compound has a molecular weight of 500 or more, the organic compound exhibits a satisfactory film-forming ability, and a resist pattern of nano level can be easily formed.

The "organic compound having a molecular weight of 500 or more" is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. In the present description and claims, the term "polymeric compound" or the term "resin" refers to a polymer having a molecular weight of 1,000 or more.

With respect to a polymeric compound, the "molecular weight" is the weight average molecular weight in terms of the polystyrene equivalent value determined by gel permeation chromatography (GPC).

As the component (A), a resin component which exhibits changed solubility in a developing solution under the action of acid may be used. Alternatively, as the component (A), a low molecular weight compound which exhibits changed solubility in a developing solution under the action of acid may be used.

When the resist composition of the present invention is a "negative resist composition for alkali developing process" which forms a negative pattern in an alkali developing process, for example, as the component (A), a base component that is soluble in an alkali developing solution is used, and a cross-linker component is also blended in the negative resist composition.

In the negative resist composition for alkali developing process, when acid is generated from the components (B) and (C) upon exposure, the action of the generated acid causes cross-linking between the base component and the cross-linker component, and the cross-linked portion becomes substantially insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) of a negative resist composition for alkali developing process, a resin that is soluble in an alkali developing solution (hereafter, referred to as "alkali-soluble resin") is used.

Examples of the alkali-soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; a (meth)acrylic resin or polycycloolefin resin having a sulfoneamide group, as disclosed in U.S. Pat. No. 6,949,325; a (meth)acrylic resin having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycycloolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linker component, at least one type of cross-linker selected from the group consisting of melamine-based cross-linkers, urea-based cross-linkers, alkylene urea-based cross-linkers, glycoluril-based cross-linkers and epoxy-based cross-linkers is preferably used. For example, typically, it is preferable to use a glycoluril-based cross-linker having a methylol group or alkoxymethyl group, a melamine-based cross-linker, or the like, as it enables formation of a favorable resist pattern with minimal swelling. The amount of the cross-linker component added is preferably within the range from 1 to 50 parts by weight, relative to 100 parts by weight of the alkali-soluble resin.

In the case where the resist composition of the present invention is a resist composition which forms a positive pattern in an alkali developing process and forms a negative pattern in a solvent developing process, it is preferable to use a base component (hereafter, referred to as "component (A0)") which exhibits increased polarity by the action of acid as the component (A). By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the component (B) and the compound (C1) upon exposure, the action of this acid causes an increase in the polarity of the base component, thereby increasing the solubility of the component (A0) in an alkali developing solution. Therefore, in the formation of a resist pattern, by conducting selective exposure of a resist film formed by applying the resist composition to a substrate, the exposed portions changes from an insoluble state to a soluble state in an alkali developing solution, whereas the unexposed portions remain insoluble in an alkali developing solution, and hence, a positive resist pattern can be formed by alkali developing.

On the other hand, in the case of applying a solvent developing process, the component (A0) exhibits high solubility in an organic developing solution prior to exposure, and when acid is generated from the component (B) and the compound (C1) upon exposure, the polarity of the component (A0) is increased by the action of the generated acid, thereby reducing the solubility of the component (A0) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be generated between the exposed portions and the unexposed portions, thereby enabling the formation of a negative resist pattern.

In the resist composition of the present invention, the component (A) is preferably a base component which exhibits increased polarity by the action of acid (i.e., a component (A0)). That is, the resist composition of the present invention is preferably a chemically amplified resist composition which becomes a positive type in the case of an alkali developing process, and a negative type in the case of a solvent developing process.

The component (A0) may be a resin component (A1) that exhibits increased polarity under the action of acid (hereafter, frequently referred to as "component (A1)"), a low molecular weight compound (A2) that exhibits increased polarity under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

In the present invention, the component (A1) preferably includes a structural unit derived from an acrylate ester or a structural unit derived from an acrylate ester in which the hydrogen atom bonded to the carbon atom on the α-position has been substituted with a substituent, i.e., a structural unit derived from an acrylate ester in which the hydrogen atom bonded to the carbon atom on the α-position may be substituted with a substituent.

In the present descriptions and the claims, the expression "structural unit derived from an acrylate ester" refers to a structural unit that is formed by the cleavage of the ethylenic double bond of an acrylate ester.

An "acrylate ester" is a compound in which the hydrogen atom at the carboxyl group terminal of acrylic acid ($CH_2$=CH—COOH) has been substituted with an organic group.

With respect to an "acrylate ester in which the hydrogen atom bonded to the carbon atom on the α-position has been substituted with a substituent", examples of the substituent include a halogen atom, an alkyl group of 1 to 5 carbon atoms, a halogenated alkyl group of 1 to 5 carbon atoms and a hydroxyalkyl group.

A carbon atom on the α-position of an acrylate ester refers to the carbon atom having the carbonyl group bonded thereto, unless specified otherwise.

Hereafter, acrylate esters in which the hydrogen atom bonded to the carbon atom on the α-position has been substituted with a substituent are frequently referred to as an "α-substituted acrylate esters". Further, acrylate esters and α-substituted acrylate esters are sometimes collectively referred to as "(α-substituted) acrylate esters".

With respect to the "α-substituted acrylate esters", examples of the halogen atom for substituting the hydrogen atom bonded to the carbon atom on the α-position include a fluorine atom, a chlorine atom, a bromine atom and an iodine atom, and a fluorine atom is particularly desirable.

The alkyl group for substituting the hydrogen atom bonded to the carbon atom on the α-position is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group.

Further, specific examples of the halogenated alkyl group for substituting the hydrogen atom bonded to the carbon atom on the α-position include groups in which some or all of the hydrogen atoms of the aforementioned "alkyl group for substituting the hydrogen atom bonded to the carbon atom on the α-position" are substituted with halogen atoms. Examples of the halogen atom include a fluorine atom, a chlorine atom, a bromine atom and an iodine atom, and a fluorine atom is particularly desirable.

Further, examples of the hydroxyalkyl group for substituting the hydrogen atom bonded to the carbon atom on the α-position include groups in which some or all of the hydrogen atoms of the aforementioned "alkyl group for substituting the hydrogen atom bonded to the carbon atom on the α-position" are substituted with hydroxyl groups.

It is preferable that a hydrogen atom, an alkyl group of 1 to 5 carbon atoms or a halogenated alkyl group of 1 to 5 carbon atoms, and more preferably a hydrogen atom, an alkyl group of 1 to 5 carbon atoms or a fluorinated alkyl group of 1 to 5 carbon atoms, be bonded to the carbon atom on the α-position in (α-substituted) acrylate esters. In terms of industrial availability, a hydrogen atom or a methyl group is the most desirable.

In the resist composition of the present invention, it is particularly desirable that the component (A1) include a structural unit (a1) derived from an acrylate ester, in which the hydrogen atom bonded to the carbon atom on the α-position may be substituted with a substituent, and also containing an acid decomposable group that exhibits increased polarity by the action of acid.

Further, in addition to the structural unit (a1), the component (A1) preferably also includes at least one type of structural unit (a2) derived from an acrylate ester in which the hydrogen atom bonded to the carbon atom on the α-position may be substituted with a substituent, and selected from the group consisting of a structural unit ($a2^L$) containing a lactone-containing cyclic group and a structural unit ($a2^S$) containing a —$SO_2$-containing cyclic group.

Moreover, in addition to the structural unit (a1) or in addition to the structural units (a1) and (a2), the component (A1) preferably also includes a structural unit (a3) derived from an acrylate ester in which the hydrogen atom bonded to the carbon atom on the α-position may be substituted with a substituent, and containing a polar group-containing aliphatic hydrocarbon group.

Furthermore, in the present invention, the component (A1) may also include a structural unit other than the aforementioned structural units (a1) to (a3).

(Structural Unit (a1))

The structural unit (a1) is a structural unit derived from an acrylate ester in which the hydrogen atom bonded to the carbon atom on the α-position may be substituted with a substituent, and containing an acid decomposable group which exhibits increased polarity by the action of acid.

As the acid decomposable group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) substantially insoluble in an alkali developing solution prior to dissociation, and then following dissociation by the action of acid, increases the solubility of the entire component (A1) in the alkali developing solution. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic" is a relative concept used in relation to the term "aromatic", and defines a group or compound that has no aromaticity.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of the substituent include an alkyl group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group.

Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cyclic alkyl group can be used. Specific examples include a 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as the groups bonded to the oxygen atom of the carbonyloxy group (—C(O)—O—) within the structural units represented by general formulas (a1"-1) to (a1"-6) shown below, can be used.

[Chemical Formula 3]

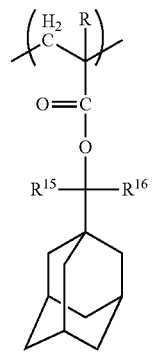

(a1"-1)

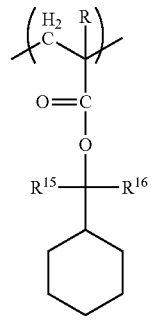

(a1"-2)

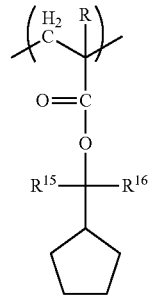

(a1"-3)

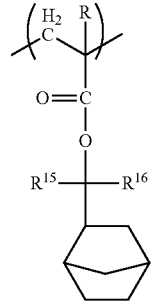

(a1"-4)

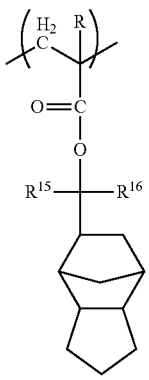

(a1″-5)

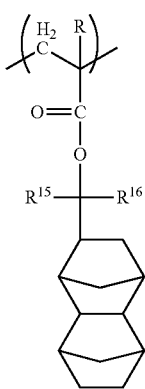

(a1″-6)

In the formulas, R represents a hydrogen atom, an alkyl group of 1 to 5 carbon atoms or a halogenated alkyl group of 1 to 5 carbon atoms; and $R^{15}$ and $R^{16}$ each represents an alkyl group (which may be linear or branched, and preferably has 1 to 5 carbon atoms).

In general formulas (a1″-1) to (a1″-6), as the alkyl group of 1 to 5 carbon atoms or halogenated alkyl group of 1 to 5 carbon atoms for R, the same alkyl groups of 1 to 5 carbon atoms or halogenated alkyl groups of 1 to 5 carbon atoms as those defined above for substituting the hydrogen atom bonded to the carbon atom on the α-position can be used.

An "acetal-type acid dissociable, dissolution inhibiting group" generally substitutes a hydrogen atom at the terminal of an alkali-soluble group such as a carboxyl group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 4]

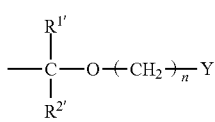

(p1)

In the formula, each of $R^{1'}$ and $R^{2'}$ independently represents a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1) above, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, and a methyl group or an ethyl group is preferable, and a methyl group is most preferable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 5]

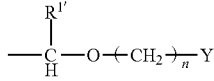

(p1-1)

In the formula, $R^{1'}$, n and Y are the same as defined above.

As the alkyl group of 1 to 5 carbon atoms for Y, the same alkyl groups of 1 to 5 carbon atoms as those described above for R can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 6]

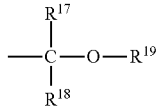

(p2)

In the formula, $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ may be bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a1), it is preferable to use at least one member selected from the group consisting of structural units represented by general formula (a1-O-1) shown below and structural units represented by general formula (a1-O-2) shown below.

[Chemical Formula 7]

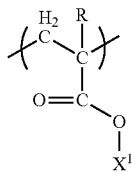

(a1-0-1)

In the formula, R represents a hydrogen atom, an alkyl group of 1 to 5 carbon atoms or a halogenated alkyl group of 1 to 5 carbon atoms; and $X^1$ represents an acid dissociable, dissolution inhibiting group.

[Chemical Formula 8]

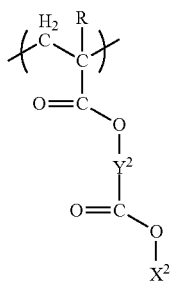

(a1-0-2)

In the formula, R represents a hydrogen atom, an alkyl group of 1 to 5 carbon atoms or a halogenated alkyl group of 1 to 5 carbon atoms; $X^2$ represents an acid dissociable, dissolution inhibiting group; and $Y^2$ represents a divalent linking group.

In general formula (a1-0-1) shown above, the alkyl group of 1 to 5 carbon atoms or halogenated alkyl group of 1 to 5 carbon atoms for R are the same as the alkyl groups of 1 to 5 carbon atoms or halogenated alkyl groups of 1 to 5 carbon atoms as those defined above which may be bonded to the α-position of the acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

Examples of the divalent linking group for $Y^2$ include an alkylene group, a divalent aliphatic cyclic group and a divalent linking group containing a hetero atom.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples of the divalent linking groups containing a hetero atom include —O—, —C(=O)—O—, —C(=O)—, —O—C(=O)—O—, —C(=O)—NH—, —NH— (H may be replaced with a substituent such as an alkyl group, an acyl group or the like), —S—, —S(=O)$_2$—, —S(=O)$_2$—O—, and groups represented by general formula "-A-O (oxygen atom)-B— (provided that in the formulas, each of A and B independently represents a divalent hydrocarbon group which may have a substituent)".

When $Y^2$ represents —NH—, the substituent (an alkyl group, an acyl group or the like) preferably has 1 to 10 carbon atoms, more preferably 1 to 8 carbon atoms, and most preferably 1 to 5 carbon atoms.

When $Y^2$ is a group represented by formula "-A-O—B—", each of A and B independently represents a divalent hydrocarbon group which may have a substituent.

The description that the hydrocarbon group "may have a substituent" means that some or all of the hydrogen atoms within the hydrocarbon group may be substituted with an atom other than a hydrogen atom or with a group.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8 carbon atoms, still more preferably 2 to 5 carbon atoms, and most preferably 2 carbon atoms.

As a linear aliphatic hydrocarbon group, a linear alkylene group is preferable, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; alkylethylene groups such as —$CH(CH_3)CH_2$—, —$CH(CH_3)CH(CH_3)$—, —$C(CH_3)_2CH_2$— and —$CH(CH_2CH_3)CH_2$—; alkyltrimethylene groups such as —$CH(CH_3)CH_2CH_2$— and —$CH_2CH(CH_3)CH_2$—; and alkyltetramethylene groups such as —$CH(CH_3)CH_2CH_2CH_2$— and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Examples of the aliphatic hydrocarbon group containing a ring include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an aforementioned chain-like aliphatic hydrocarbon group, or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

As A, a linear aliphatic hydrocarbon group is preferred, a linear alkylene group is more preferred, a linear alkylene group of 2 to 5 carbon atoms is still more preferred, and an ethylene group is particularly desirable.

Examples of the aromatic hydrocarbon group for A include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

Examples of the hydrocarbon groups for B include the same divalent hydrocarbon groups as those described above for A.

As B, a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 9]

(a1-1)

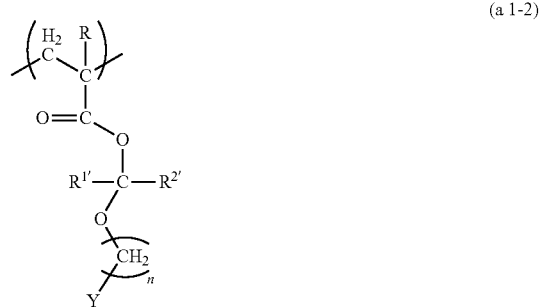

(a1-2)

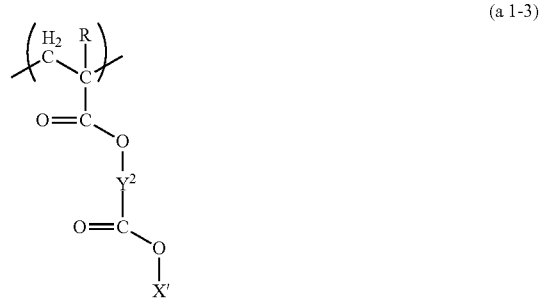

(a1-3)

(a1-4)

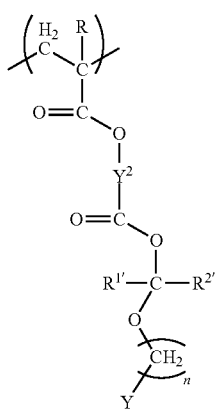

In the formulas, X' represents a tertiary alkyl ester-type acid dissociable, dissolution inhibiting group; Y represents an alkyl group of 1 to 5 carbon atoms or an aliphatic cyclic group; n represents an integer of 0 to 3; $Y^2$ represents a divalent linking group; R is the same as defined above; and each of $R^{1'}$ and $R^{2'}$ independently represents a hydrogen atom or an alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1'}$, $R^{2'}$, n and Y are respectively the same as defined for $R^{1'}$, $R^{2'}$, n' and Y in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 10]

(a1-1-1)

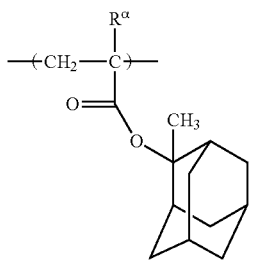

(a1-1-2)

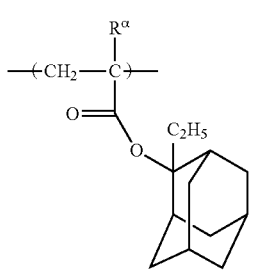

(a1-1-3)

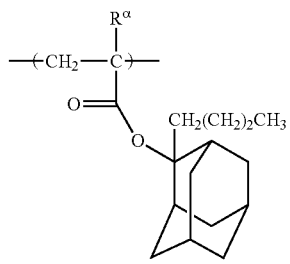

(a1-1-4)

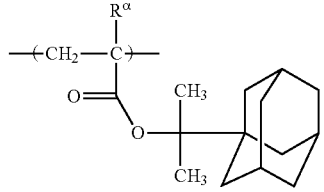

(a1-1-5)

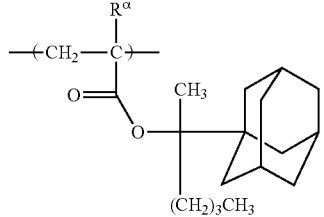

(a1-1-6)

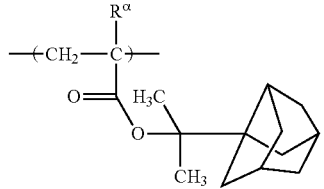

(a1-1-7)

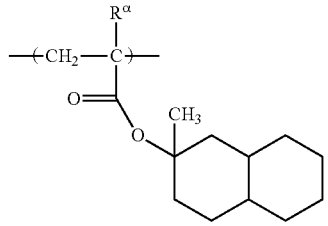

(a1-1-8)

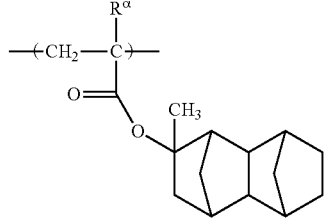

(a1-1-9)

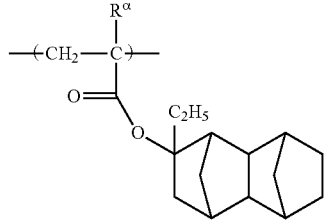

[Chemical Formula 11]

(a1-1-10) 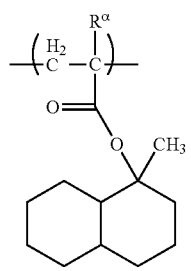
(a1-1-11) 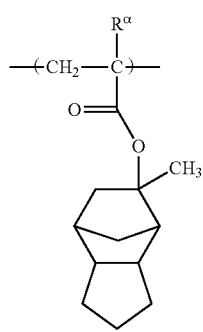
(a1-1-12) 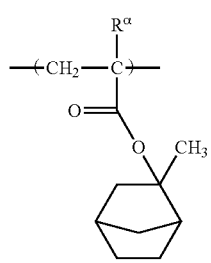
(a1-1-13) 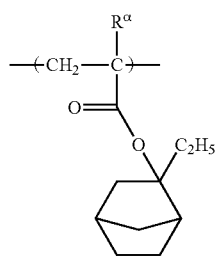
(a1-1-14) 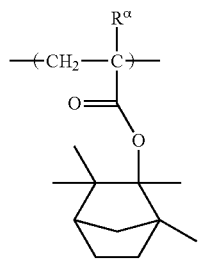
(a1-1-15) 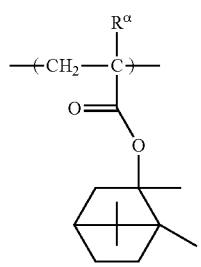
(a1-1-16) 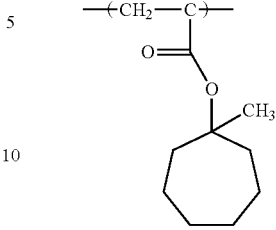
(a1-1-17) 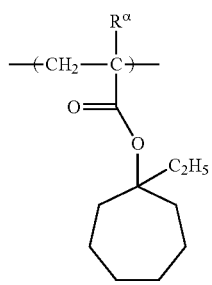
(a1-1-18) 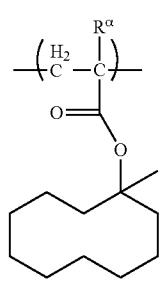
(a1-1-19) 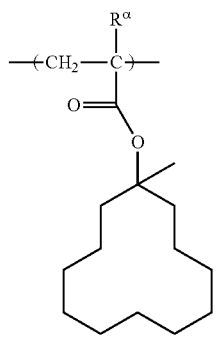
(a1-1-20) 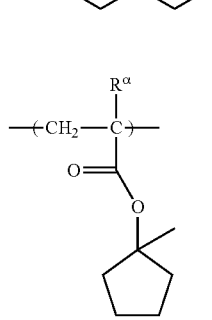

(a1-1-21) 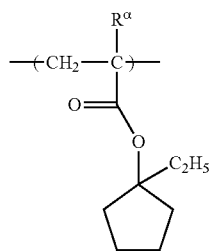
[Chemical Formula 12]
(a1-1-22) 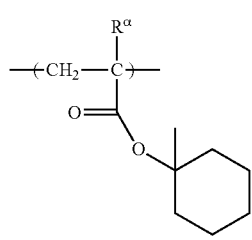
(a1-1-23) 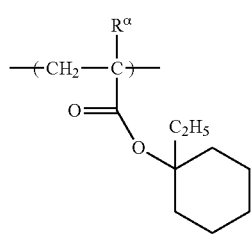
(a1-1-24) 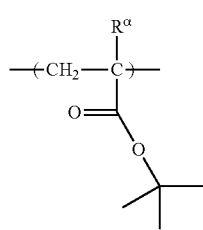
(a1-1-25) 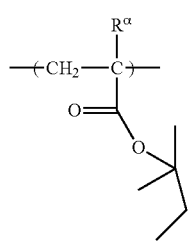
(a1-1-26) 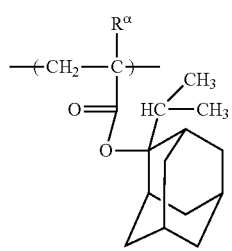
(a1-1-27) 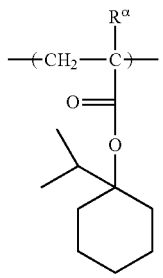
(a1-1-28) 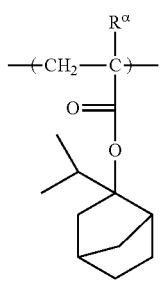
(a1-1-29) 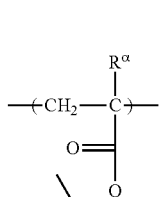
(a1-1-30) 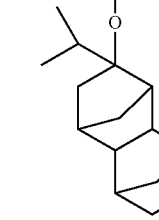
(a1-1-31) 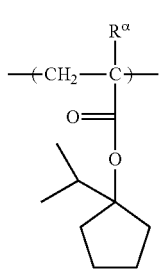

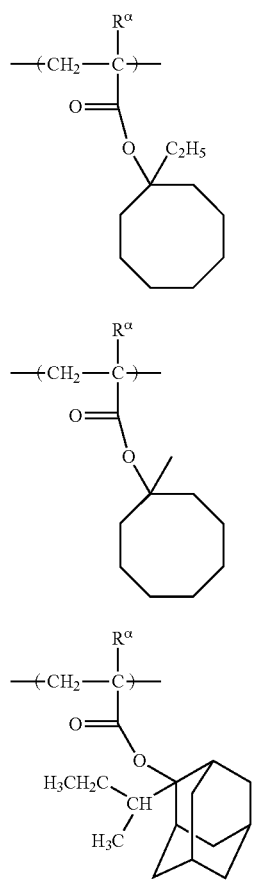
(a1-1-32)
(a1-1-33)
(a1-1-34)
[Chemical Formula 13]
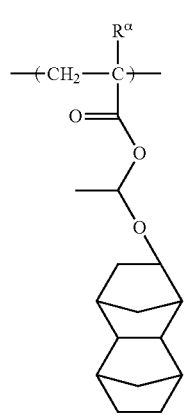
(a1-2-1)
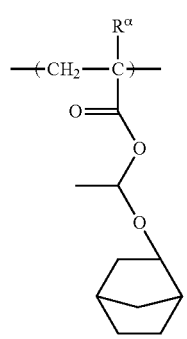
(a1-2-2)
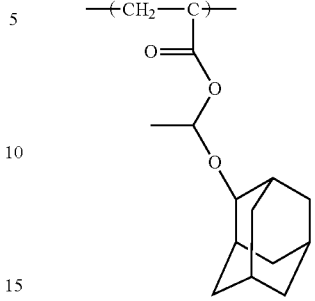
(a1-2-3)
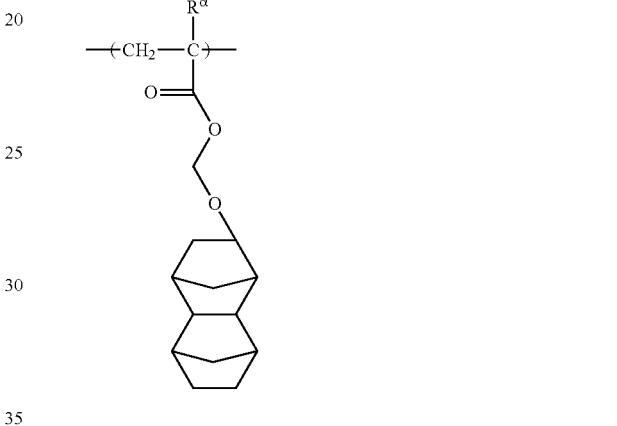
(a1-2-4)
(a1-2-5)
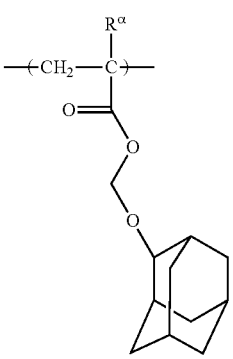
(a1-2-6)

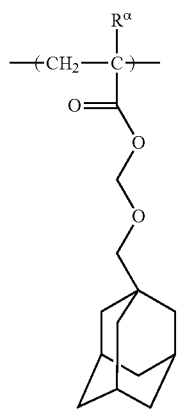
(a1-2-7)
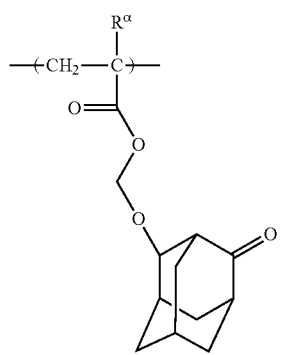
(a1-2-8)
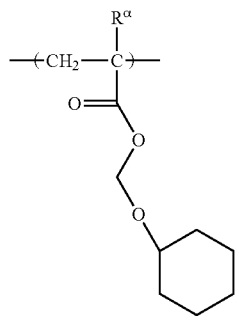
(a1-2-9)
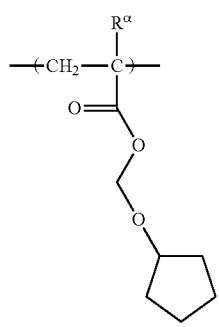
(a1-2-10)
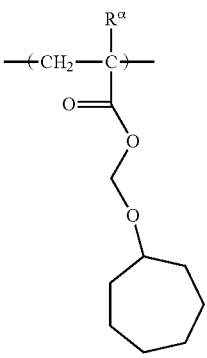
(a1-2-11)
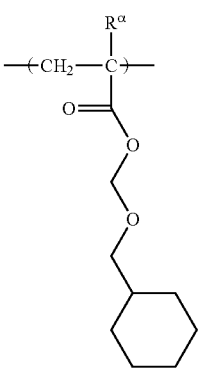
(a1-2-12)
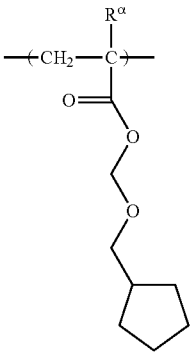
(a1-2-13)
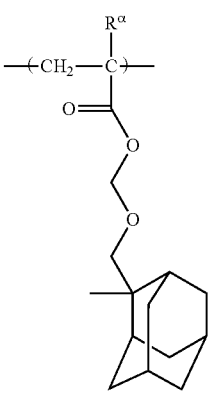
(a1-2-14)

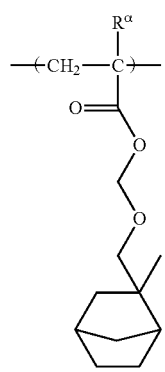 (a1-2-15)
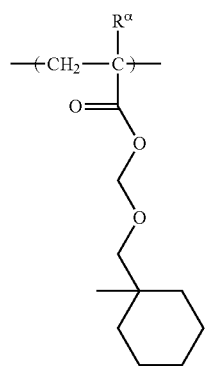 (a1-2-16)
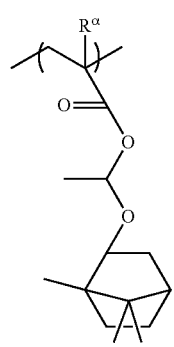 (a1-2-17)
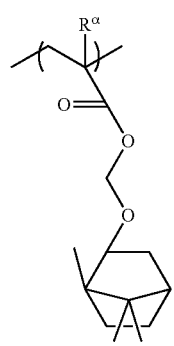 (a1-2-18)
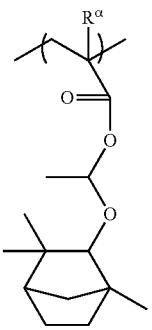 (a1-2-19)
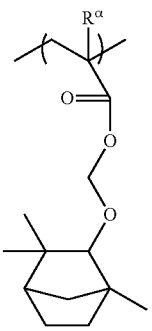 (a1-2-20)
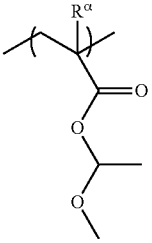 (a1-2-21)
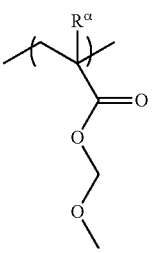 (a1-2-22)
(a1-2-23)

-continued
(a1-2-24)
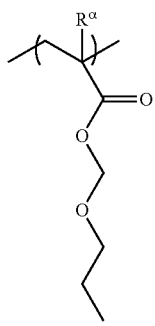
[Chemical Formula 14]
(a1-3-1)
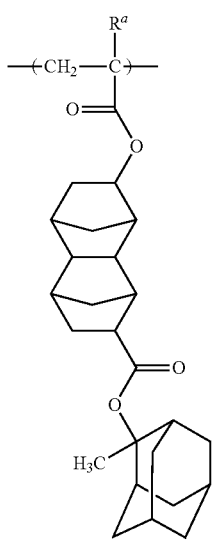
(a1-3-2)
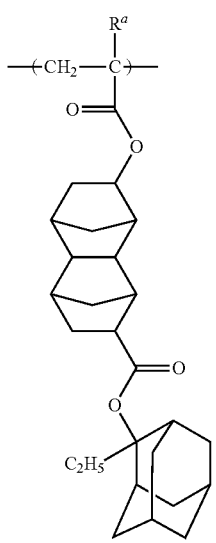
(a1-3-3)
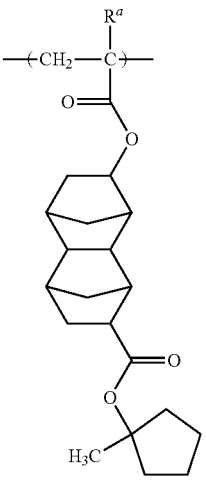
(a1-3-4)
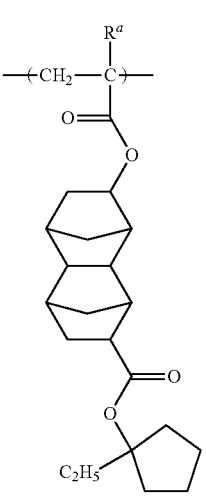
(a1-3-5)
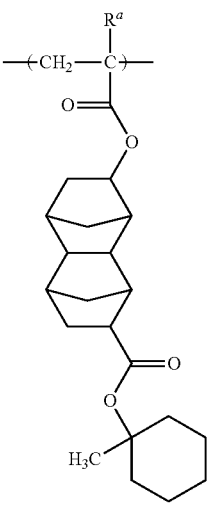

(a1-3-6) 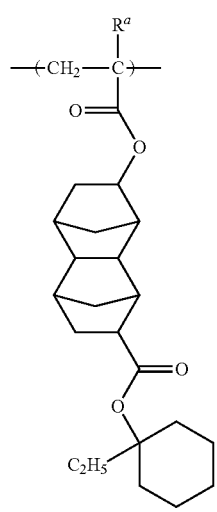
(a1-3-7) 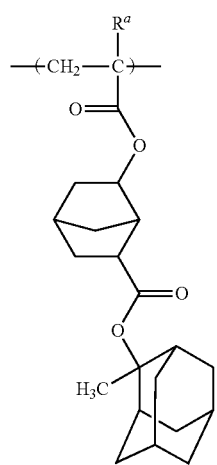
(a1-3-8) 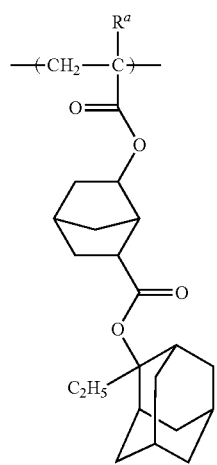
(a1-3-9) 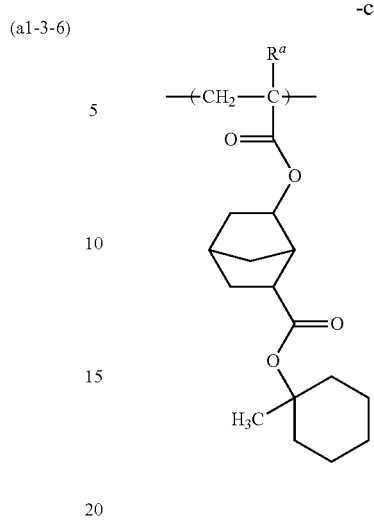
(a1-3-10) 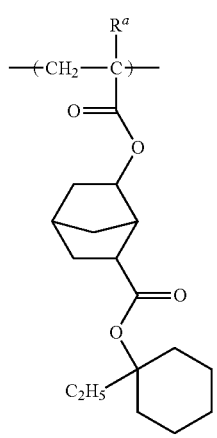
(a1-3-11) 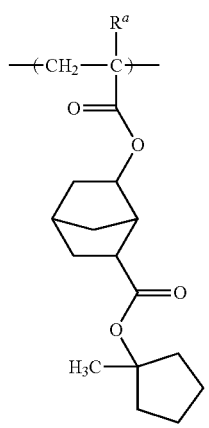

(a1-3-12) 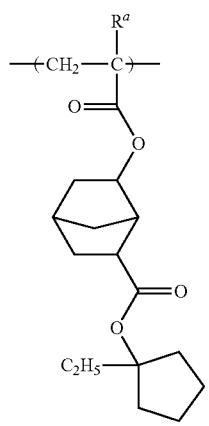
(a1-3-13) 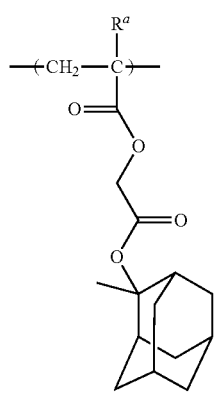
(a1-3-14) 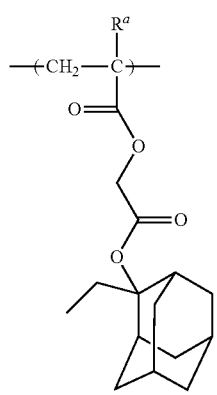
(a1-3-15) 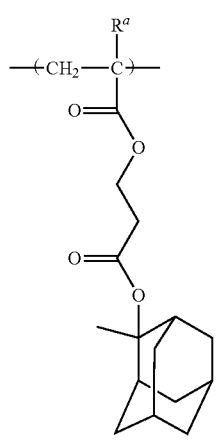
(a1-3-16) 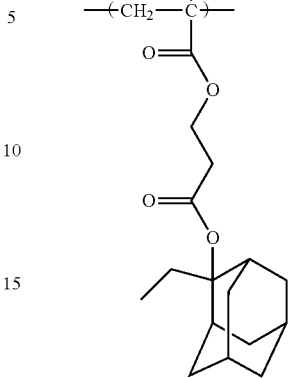
(a1-3-17) 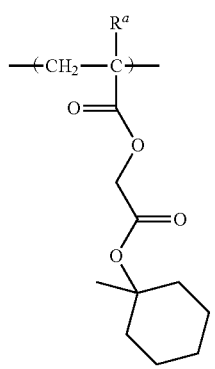
(a1-3-18) 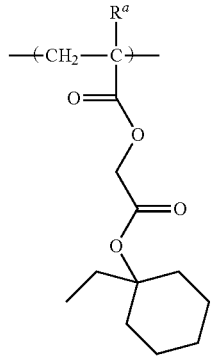
[Chemical Formula 15]
(a1-3-19) 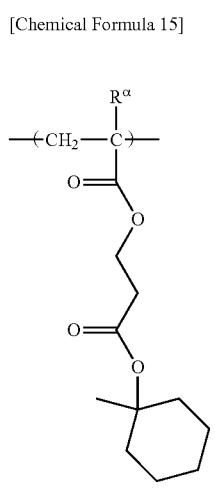

-continued
(a1-3-20)
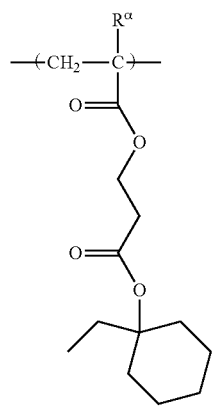
(a1-3-21)
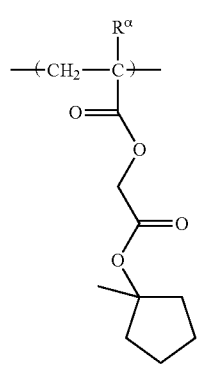
(a1-3-22)
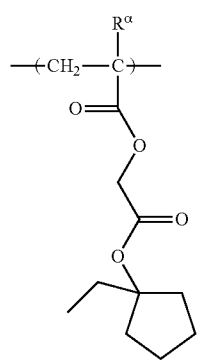
(a1-3-23)
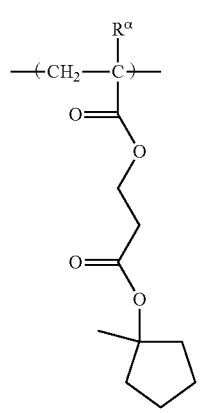
-continued
(a1-3-24)
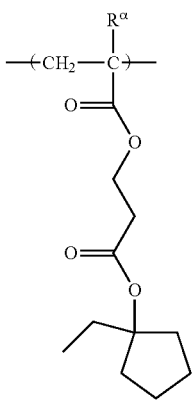
[Chemical Formula 16]
(a1-3-25)
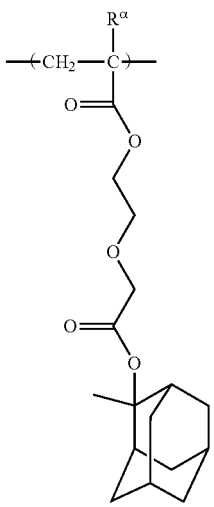
(a1-3-26)
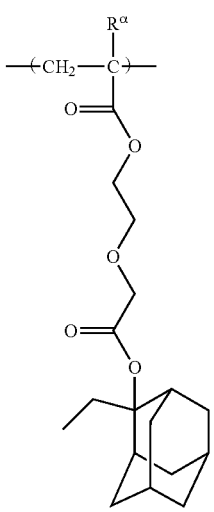

(a1-3-27) 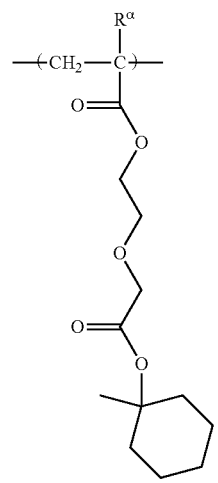
(a1-3-28) 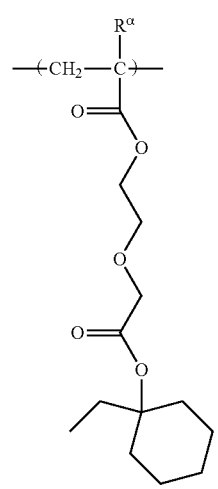
(a1-3-29) 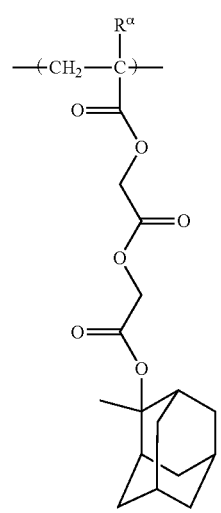
(a1-3-30) 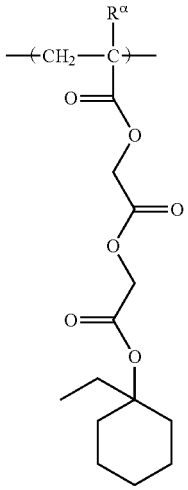
(a1-3-31) 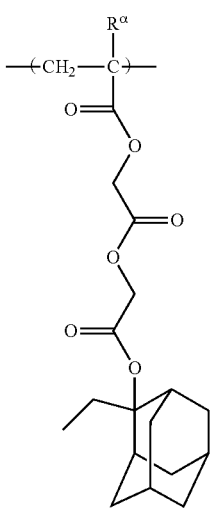
(a1-3-32) 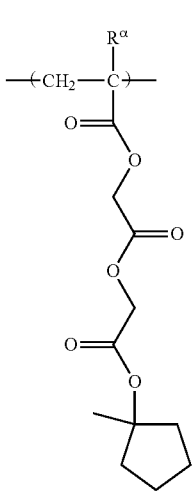

[Chemical Formula 17]
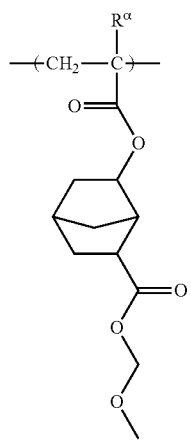
(a1-4-1)
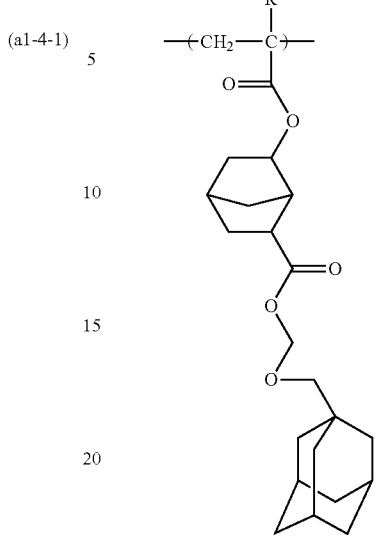
(a1-4-2)
(a1-4-3)
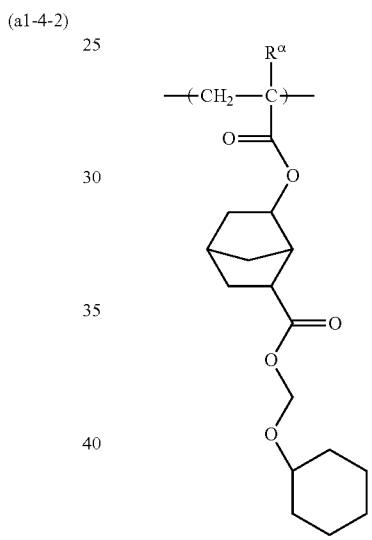
(a1-4-4)
(a1-4-5)
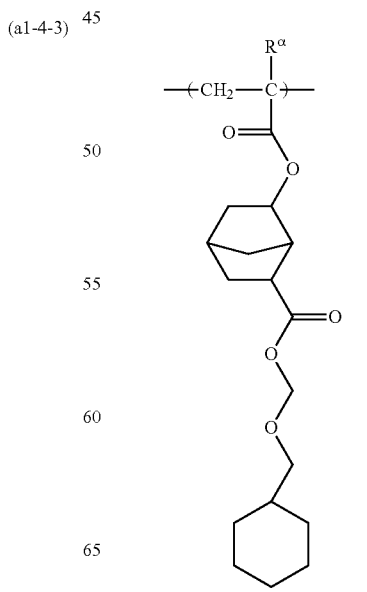
(a1-4-6)

(a1-4-7)
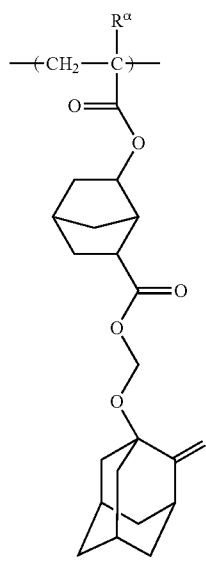
(a1-4-8)
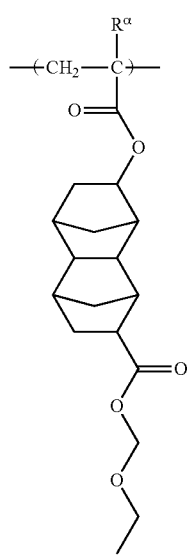
(a1-4-9)
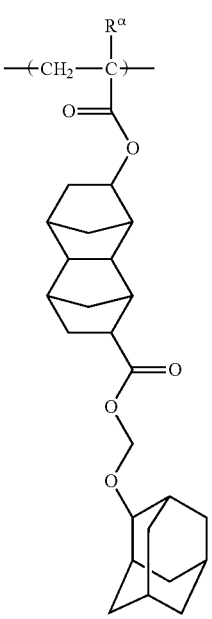
(a1-4-10)
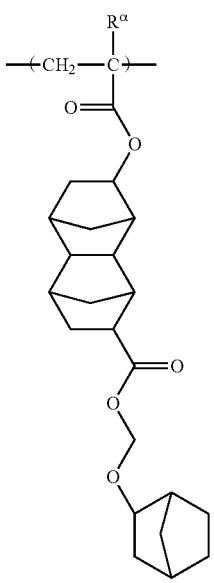

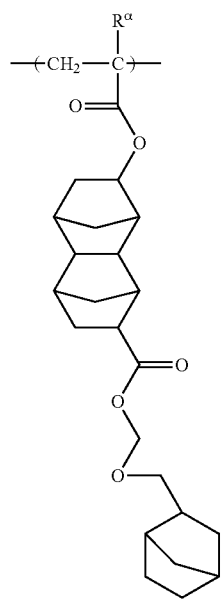
(a1-4-11)
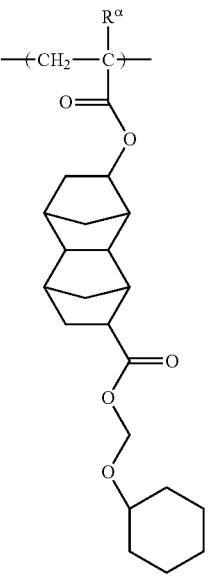
(a1-4-13)
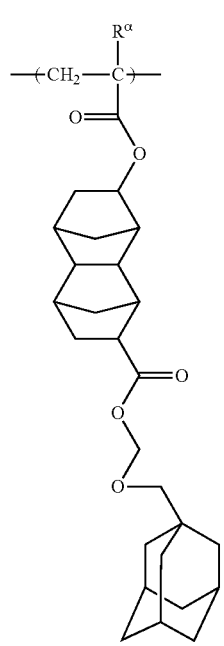
(a1-4-12)
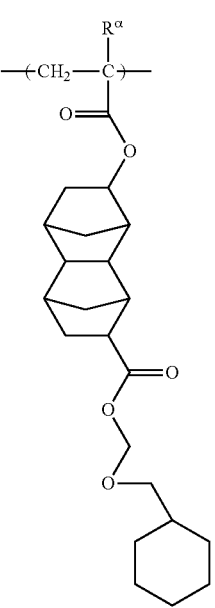
(a1-4-14)

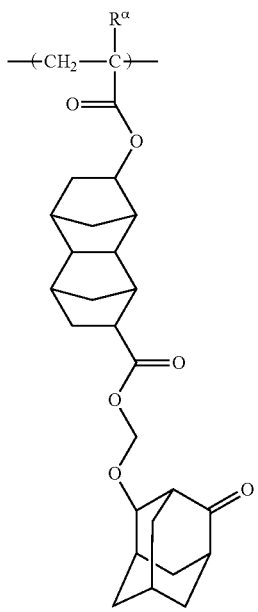

(a1-4-15)

As the structural unit (a1), one type of structural unit may be used alone, or two or more types of structural units may be used in combination.

Among these, structural units represented by general formula (a1-1) or (a1-3) are preferable. More specifically, at least one structural unit selected from the group consisting of structural units represented by formulas (a1-1-1) to (a1-1-4), (a1-1-16) to (a1-1-17), (a1-1-20) to (a1-1-23), (a1-1-26), (a1-1-32) to (a1-1-33), (a1-1-34) and (a1-3-25) to (a1-3-28) is more preferable.

Furthermore, as the structural unit (a1), structural units represented by general formula (a1-1-01) shown below which includes the structural units represented by formulas (a1-1-1) to (a1-1-3), (a1-1-26) and (a1-1-34); structural units represented by general formula (a1-1-02) shown below which includes the structural units represented by formulas (a1-1-16) to (a1-1-17), (a1-1-20) to (a1-1-23) and (a1-1-32) to (a1-1-33); structural units represented by general formula (a1-3-01) shown below which includes the structural units represented by formulas (a1-3-25) to (a1-3-26); structural units represented by general formula (a1-3-02) shown below which includes the structural units represented by formulas (a1-3-27) to (a1-3-28); structural units represented by general formula (a1-3-03-1) shown below which includes the structural units represented by formulas (a1-3-29) and (a1-3-31); or structural units represented by general formula (a1-3-03-2) shown below which includes the structural units represented by formulas (a1-3-30) and (a1-3-32) are also particularly desirable.

[Chemical Formula 18]

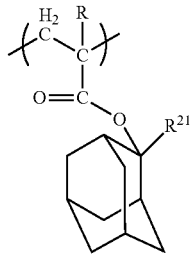

(a1-1-01)

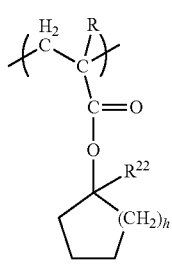

(a1-1-02)

In formula (a1-1-01), R represents a hydrogen atom, an alkyl group of 1 to 5 carbon atoms or a halogenated alkyl group of 1 to 5 carbon atoms; and $R^{21}$ represents an alkyl group of 1 to 5 carbon atoms. In formula (a1-1-02), R is the same as defined above; $R^{22}$ represents an alkyl group of 1 to 5 carbon atoms; and h represents an integer of 1 to 6.

In general formula (a1-1-01), R is the same as defined above.

As the alkyl group of 1 to 5 carbon atoms for $R^{21}$, the same alkyl groups of 1 to 5 carbon atoms as those described above for R can be used, and a methyl group, an ethyl group or an isopropyl group is preferable.

In general formula (a1-1-02), R is the same as defined above.

As the alkyl group of 1 to 5 carbon atoms for $R^{22}$, the same alkyl groups of 1 to 5 carbon atoms as those described above for R can be used, and a methyl group, an ethyl group or an isopropyl group is preferable. h is preferably 1 or 2, and more preferably 2.

[Chemical Formula 19]

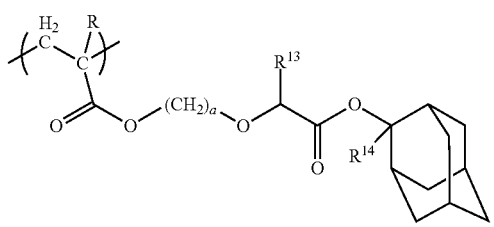

(a1-3-01)

In the formula, R represents a hydrogen atom, an alkyl group of 1 to 5 carbon atoms or a halogenated alkyl group of 1 to 5 carbon atoms; $R^{14}$ represents an alkyl group of 1 to 5 carbon atoms; $R^{13}$ represents a hydrogen atom or a methyl group; and a represents an integer of 1 to 10.

[Chemical Formula 20]

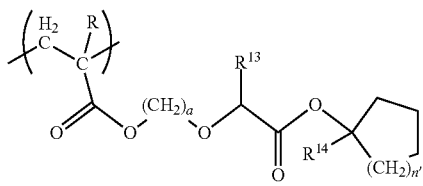
(a1-3-02)

In the formula, R represents a hydrogen atom, an alkyl group of 1 to 5 carbon atoms or a halogenated alkyl group of 1 to 5 carbon atoms; $R^{14}$ represents an alkyl group of 1 to 5 carbon atoms; $R^{13}$ represents a hydrogen atom or a methyl group; a represents an integer of 1 to 10; and n' represents an integer of 1 to 6.

In general formulas (a1-3-01) and (a1-3-02), R is the same as defined above.

$R^{13}$ is preferably a hydrogen atom.

As the alkyl group of 1 to 5 carbon atoms for $R^{14}$, the same alkyl groups of 1 to 5 carbon atoms as those described above for R can be used, and a methyl group or an ethyl group is preferable.

a is preferably an integer of 1 to 8, more preferably an integer of 2 to 5, and most preferably 2.

n' is preferably an integer of 1 or 2, more preferably 1.

[Chemical Formula 21]

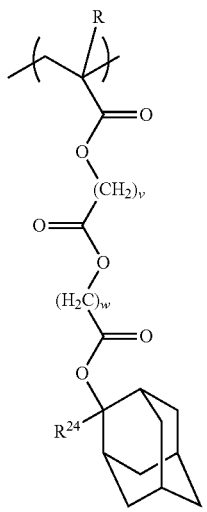
(a1-3-03-1)

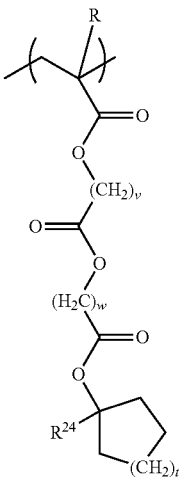
(a1-3-03-2)

In the formulas, R is the same as defined above; $R^{24}$ represents an alkyl group of 1 to 5 carbon atoms; v represents an integer of 1 to 10; w represents an integer of 1 to 10; and t represents an integer of 0 to 3.

R is the same as defined above.

As the alkyl group of 1 to 5 carbon atoms for $R^{24}$, the same alkyl groups of 1 to 5 carbon atoms as those described above for R can be used, and a methyl group or an ethyl group is preferable.

v is preferably an integer of 1 to 5, and most preferably 1 or 2.

w is preferably an integer of 1 to 5, and most preferably 1 or 2.

t is preferably an integer of 1 to 3, and most preferably 1 or 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

—Structural Unit (a2)

The structural unit (a2) is a structural unit derived from an acrylate ester in which the hydrogen atom bonded to the carbon atom on the α-position may be substituted with a substituent, and is at least one structural unit selected from the group consisting of structural units containing a —SO$_2$-containing cyclic group and derived from an acrylate ester (hereafter, referred to as "structural unit (a2$^S$)") and structural units containing a lactone-containing cyclic group and derived from an acrylate ester (hereafter, referred to as "structural unit (a2$^L$)").

By virtue of the structural unit (a2) containing a —SO$_2$-containing cyclic group or a lactone-containing cyclic group, a positive resist composition containing the component (A1) is capable of improving the adhesion of a resist film to a substrate, and increasing the compatibility with the developing solution containing water, thereby contributing to improvement of lithography properties.

—Structural unit (a2$^S$):

The structural unit (a2$^S$) is a structural unit derived from an acrylate ester in which the hydrogen atom bonded to the carbon atom on the α-position may be substituted with a substituent, and is a structural unit derived from an acrylate ester containing a —SO$_2$-containing cyclic group.

Here, a "—SO$_2$-containing cyclic group" refers to a cyclic group having a ring that contains —SO$_2$— within the ring skeleton thereof, i.e., a cyclic group in which the sulfur atom (S) within —SO$_2$— forms part of the ring skeleton of the cyclic group. This ring that contains —SO$_2$— within the ring skeleton thereof is counted as the first ring. A cyclic group in which the only ring structure is this ring is referred to as a monocyclic group, and a group containing other ring structures is described as a polycyclic group regardless of the structure of the other rings. The —SO$_2$-containing cyclic group may be either a monocyclic group or a polycyclic group.

As the —SO$_2$-containing cyclic group, a cyclic group containing —O—SO$_2$— within the ring skeleton thereof, i.e., a cyclic group containing a sultone ring in which —O—S— within the —O—SO$_2$— group forms part of the ring skeleton thereof is particularly desirable.

The —SO$_2$-containing cyclic group preferably has 3 to 30 carbon atoms, more preferably 4 to 20 carbon atoms, still more preferably 4 to 15 carbon atoms, and most preferably 4 to 12 carbon atoms. Herein, the number of carbon atoms refers to the number of carbon atoms constituting the ring skeleton, excluding the number of carbon atoms within a substituent.

The —SO$_2$-containing cyclic group may be either a —SO$_2$-containing aliphatic cyclic group or a —SO$_2$-containing aromatic cyclic group, but is preferably a —SO$_2$-containing aliphatic cyclic group.

Examples of the —SO$_2$-containing aliphatic cyclic group include groups in which part of the carbon atoms constituting the ring skeleton thereof has been substituted with a —SO$_2$— group or a —O—SO$_2$— group and has at least one hydrogen atom removed from the aliphatic hydrocarbon ring. Specific examples include groups in which a —CH$_2$— group constituting the ring skeleton thereof has been substituted with a —SO$_2$— group and has at least one hydrogen atom removed from the aliphatic hydrocarbon ring; and groups in which a —CH$_2$—CH$_2$— group constituting the ring skeleton thereof has been substituted with a —O—SO$_2$— group and has at least one hydrogen atom removed from the aliphatic hydrocarbon ring.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —SO$_2$-containing cyclic group may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

In those cases where R" represents a cyclic alkyl group, the cyclic alkyl group preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxyl group.

More specific examples of the —SO$_2$-containing cyclic group include groups represented by general formulas (3-1) to (3-4) shown below.

[Chemical Formula 22]

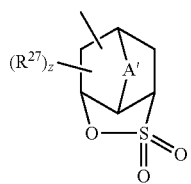

(3-1)

-continued

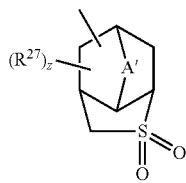 (3-2)

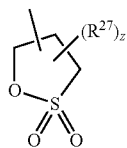 (3-3)

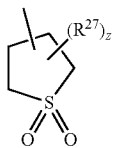 (3-4)

[Chemical Formula 23]

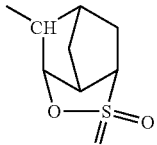 (3-1-1)

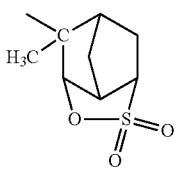 (3-1-2)

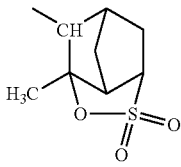 (3-1-3)

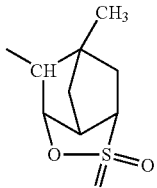 (3-1-4)

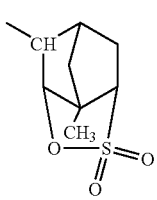 (3-1-5)

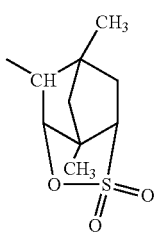 (3-1-6)

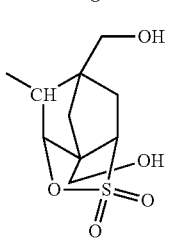 (3-1-7)

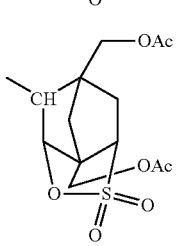 (3-1-8)

In the formulas, A' represents an oxygen atom, a sulfur atom or an alkylene group of 1 to 5 carbon atoms which may contain an oxygen atom or a sulfur atom; z represents an integer of 0 to 2; and $R^{27}$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH₂—, —CH₂—O—CH₂—, —S—CH₂— and —CH₂—S—CH₂—.

A' is preferably an alkylene group of 1 to 5 carbon atoms or —O—, is more preferably an alkylene group of 1 to 5 carbon atoms, and is most preferably a methylene group.

z represents an integer of 0 to 2, and is most preferably 0.

When z is 2, the plurality of $R^{27}$ may be the same or different from each other.

As the alkyl group, alkoxy group, halogenated alkyl group, —COOR", —OC(=O)R" and hydroxyalkyl group for $R^{27}$, the same alkyl groups, alkoxy groups, halogenated alkyl groups, —COOR", —OC(=O)R" and hydroxyalkyl groups as those described above as the substituent which the —SO₂- containing cyclic group may have can be used.

Specific examples of the cyclic groups represented by general formulas (3-1) to (3-4) are shown below. In the formulas shown below, "Ac" represents an acetyl group.

(3-1-9)
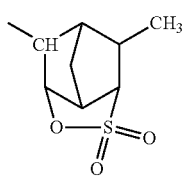
(3-1-10)
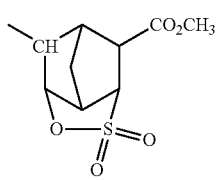
(3-1-11)
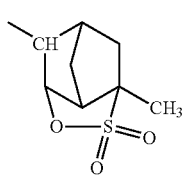
(3-1-12)
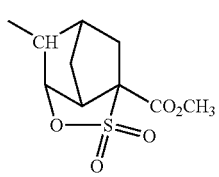
[Chemical Formula 24]
(3-1-13)
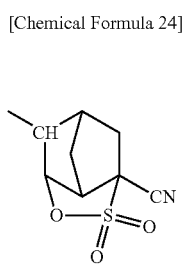
(3-1-14)
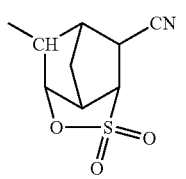
(3-1-15)
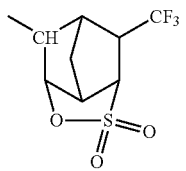
(3-1-16)
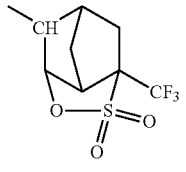
(3-1-17)
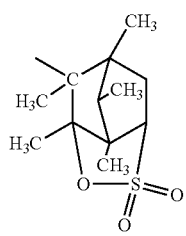
[Chemical Formula 25]
(3-1-18)
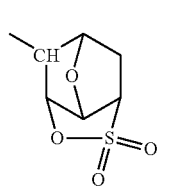
(3-1-19)
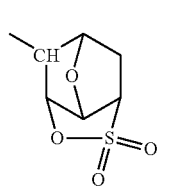
(3-1-20)
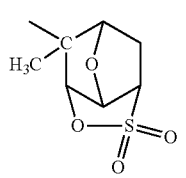
(3-1-21)
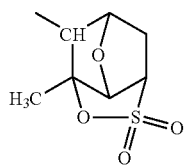
(3-1-22)
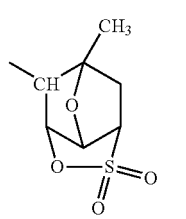
(3-1-23)
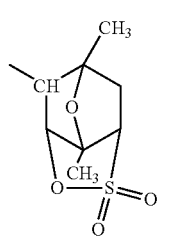

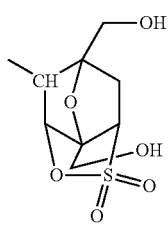 (3-1-24)

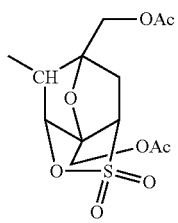 (3-1-25)

[Chemical Formula 26]

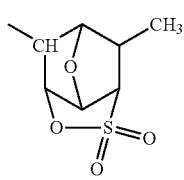 (3-1-26)

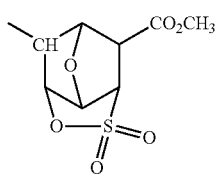 (3-1-27)

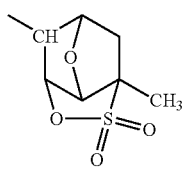 (3-1-28)

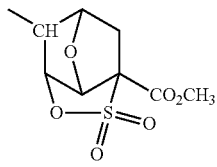 (3-1-29)

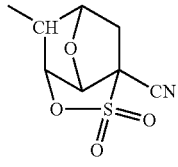 (3-1-30)

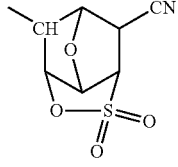 (3-1-31)

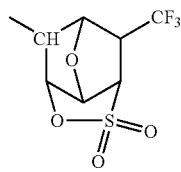 (3-1-32)

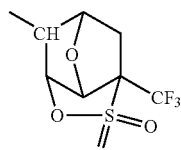 (3-1-33)

[Chemical Formula 27]

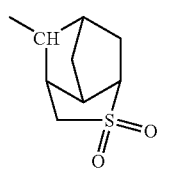 (3-2-1)

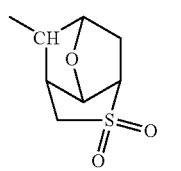 (3-2-2)

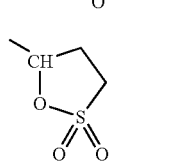 (3-3-1)

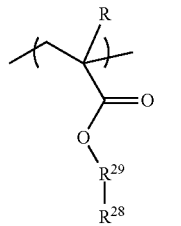 (3-4-1)

Of the various possibilities described above, as the —SO$_2$-containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by the aforementioned chemical formula (3-1-1) is most preferable.

More specific examples of the structural unit (a2$^S$) include structural units represented by general formula (a2-0) shown below.

[Chemical Formula 28]

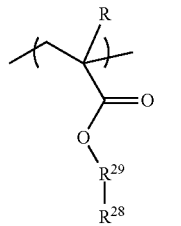 (a2-0)

In the formula, R represents a hydrogen atom, an alkyl group of 1 to 5 carbon atoms or a halogenated alkyl group of 1 to 5 carbon atoms; $R^{28}$ represents a —$SO_2$-containing cyclic group; and $R^{29}$ represents a single bond or a divalent linking group.

In general formula (a2-0), R is the same as defined above.

$R^{28}$ is the same as defined for the aforementioned —$SO_2$-containing cyclic group.

$R^{29}$ may be either a single bond or a divalent linking group. In terms of the effects of the present invention, a divalent linking group is preferable.

The divalent linking group for $R^{29}$ is not particularly limited. For example, the same divalent linking groups as those listed for $Y^2$ in the above general formula (a1-0-2) described in connection with the structural unit (a1) can be used. Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^2$.

As the divalent linking group containing an ester bond, a group represented by general formula: —$R^{30}$—C(=O)—O— (in the formula, $R^{30}$ represents a divalent linking group) is particularly desirable. That is, the structural unit (a2$^S$) is preferably a structural unit represented by general formula (a2-0-1) shown below.

[Chemical Formula 29]

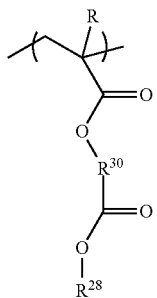

(a2-0-1)

In the formula, R and $R^{28}$ are the same as defined above; and $R^{30}$ represents a divalent linking group.

$R^{30}$ is not particularly limited, and examples thereof include the same divalent linking groups as those listed for $Y^2$ in the above general formula (a1-0-2) described in connection with the structural unit (a1).

As the divalent linking group for $R^{30}$, a linear or branched alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, divalent alicyclic hydrocarbon group and divalent linking group containing a hetero atom as those described above as preferred examples for $Y^2$ can be used.

Among these, a linear or branched alkylene group, or a divalent linking group containing an oxygen atom as a hetero atom is preferable.

As the linear alkylene group, a methylene group or an ethylene group is preferable, and a methylene group is particularly desirable.

As the branched alkylene group, an alkylmethylene group or an alkylethylene group is preferable, and —CH($CH_3$)—, —C($CH_3$)$_2$— or —C($CH_3$)$_2CH_2$— is particularly desirable.

As the divalent linking group containing an oxygen atom, a divalent linking group containing an ether bond or an ester bond is preferable, and a group represented by the aforementioned formula -A-O—B—, -[A-C(=O)—O]$_m$—B— or -A-O—C(=O)—B— is more preferable.

Among these, a group represented by the formula -A-O—C(=O)—B— is preferable, and a group represented by the formula: —($CH_2$)$_c$—C(=O)—O—($CH_2$)$_d$— is particularly desirable. c represents an integer of 1 to 5, and preferably 1 or 2. d represents an integer of 1 to 5, and preferably 1 or 2.

In particular, as the structural unit (a2$^S$), a structural unit represented by general formula (a0-1-11) or (a0-1-12) shown below is preferable, and a structural unit represented by general formula (a0-1-12) shown below is more preferable.

[Chemical Formula 30]

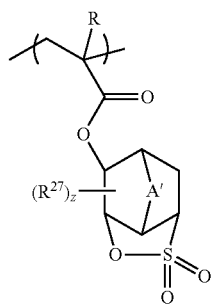

(a0-1-11)

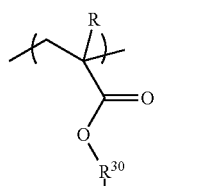

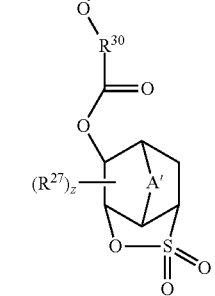

(a0-1-12)

In the formulas, R, A', $R^{27}$, z and $R^{30}$ are the same as defined above.

In general formula (a0-1-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a0-1-12), a structural unit represented by general formula (a0-1-12a) or (a0-1-12b) shown below is particularly desirable.

[Chemical Formula 31]

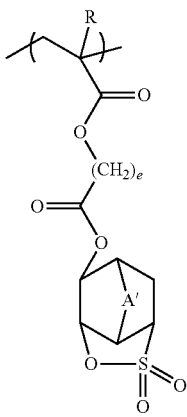
(a0-1-12a)

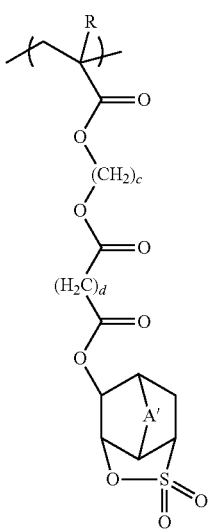
(a0-1-12b)

In the formulas, R and A' are the same as defined above; and each of c to e independently represents an integer of 1 to 3.

Structural Unit (a2$^L$):

The structural unit (a2$^L$) is a structural unit derived from an acrylate ester in which the hydrogen atom bonded to the carbon atom on the α-position may be substituted with a substituent, and is a structural unit derived from an acrylate ester containing a lactone-containing cyclic group.

The term "lactone-containing cyclic group" refers to a cyclic group including a ring containing a —O—C(O)— group within the ring structure thereof (lactone ring). This "lactone ring" is counted as the first ring, so that a lactone-containing cyclic group in which the only ring structure is the lactone ring is referred to as a monocyclic group, and groups that also contain other ring structures are described as polycyclic groups regardless of the structure of the other rings. The lactone-containing cyclic group may be either a monocyclic group or a polycyclic group.

The lactone-containing cyclic group for the structural unit (a2$^L$) is not particularly limited, and an arbitrary group may be used. Specific examples of lactone-containing monocyclic groups include a group in which one hydrogen atom has been removed from a 4- to 6-membered lactone ring, such as a group in which one hydrogen atom has been removed from β-propionolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

Examples of the structural unit (a2$^L$) include structural units represented by the aforementioned general formula (a2-0) in which the R$^{28}$ group has been substituted with a lactone-containing cyclic group. Specific examples thereof include structural units represented by general formulas (a2-1) to (a2-5) shown below.

[Chemical Formula 32]

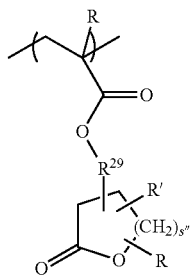
(a2-1)

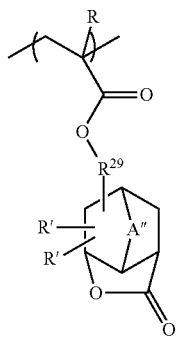
(a2-2)

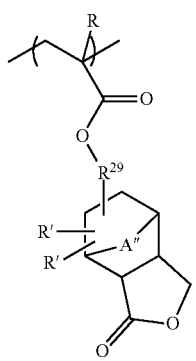
(a2-3)

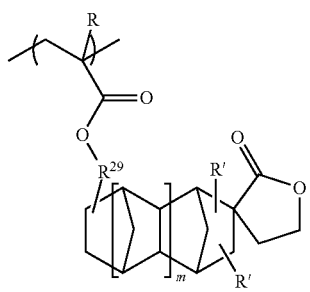
(a2-4)

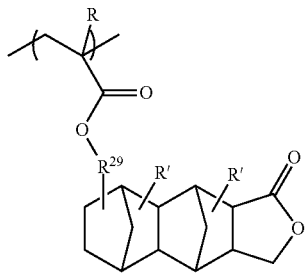
(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group.

In terms of industrial availability, R' is preferably a hydrogen atom.

The alkyl group for R" may be any of linear, branched or cyclic.

In those cases where R" represents a linear or branched alkyl group, the alkyl group preferably has 1 to 10 carbon atoms, and more preferably 1 to 5 carbon atoms.

In those cases where R" represents a cyclic alkyl group, the cyclic alkyl group preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylmethylene group is preferable, and a methylene group is particularly desirable.

$R^{29}$ is the same as defined for $R^{29}$ in the aforementioned general formula (a2-0).

In formula (a2-1), s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 33]

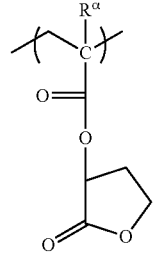
(a2-1-1)

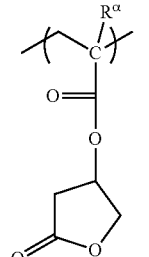
(a2-1-2)

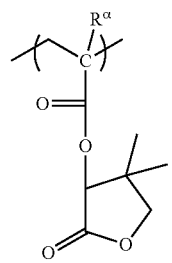
(a2-1-3)

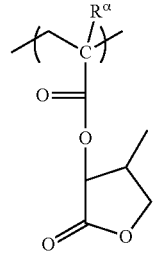
(a2-1-4)

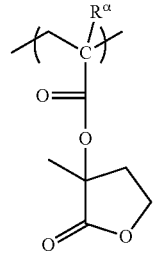
(a2-1-5)

(a2-1-6)
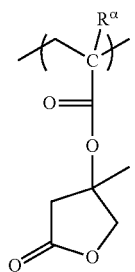
(a2-1-7)
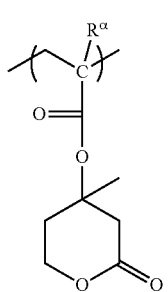
(a2-1-8)
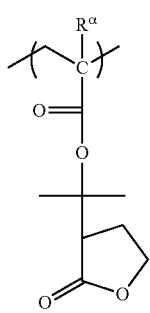
(a2-1-9)
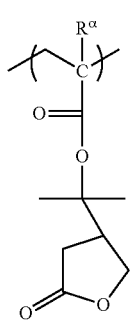
(a2-1-10)
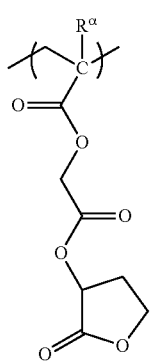
(a2-1-11)
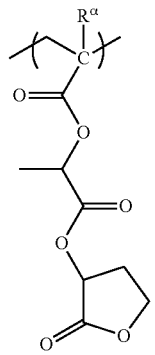
(a2-1-12)
(a2-1-13)
[Chemical Formula 34]
(a2-2-1)
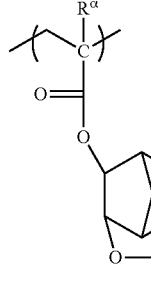

(a2-2-2)
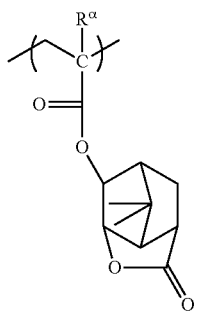
(a2-2-3)
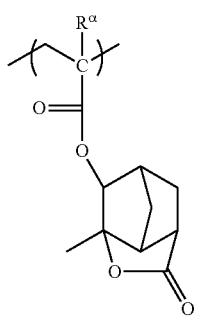
(a2-2-4)
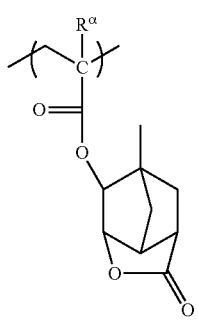
(a2-2-5)
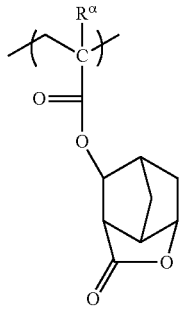
(a2-2-6)
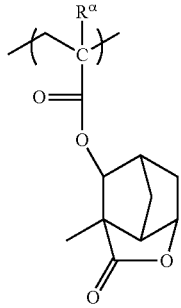
(a2-2-7)
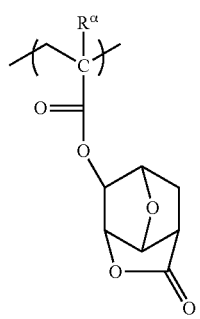
(a2-2-8)
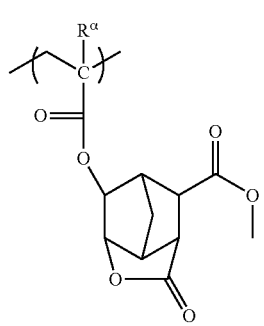
(a2-2-9)
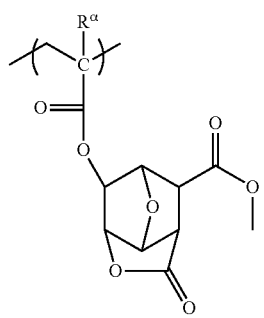
(a2-2-10)
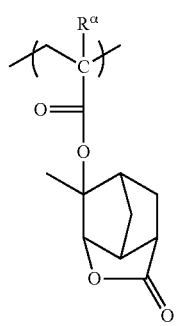
(a2-2-11)
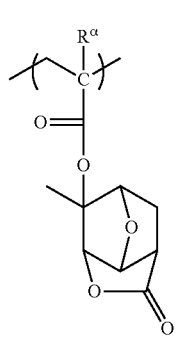

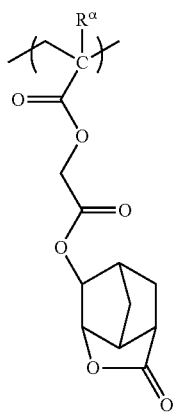 (a2-2-12)
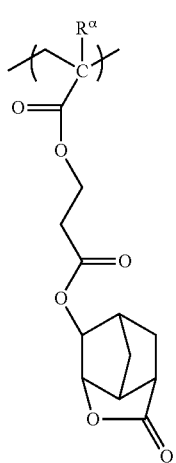 (a2-2-13)
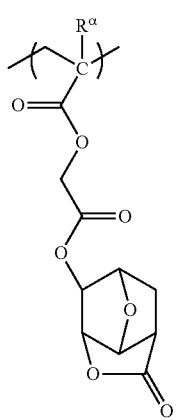 (a2-2-14)
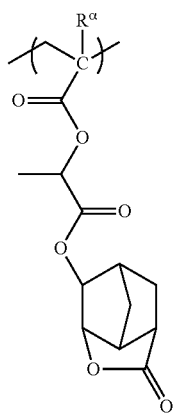 (a2-2-15)
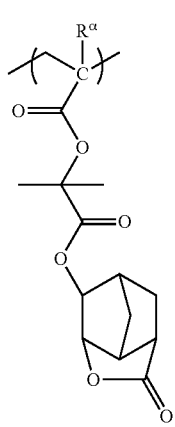 (a2-2-16)
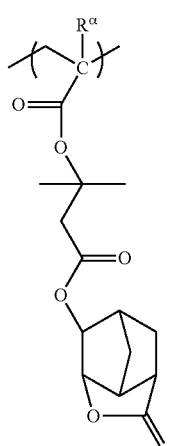 (a2-2-17)
[Chemical Formula 35]
(a2-3-1)

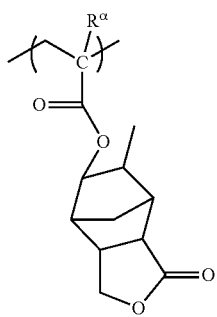
(a2-3-2)
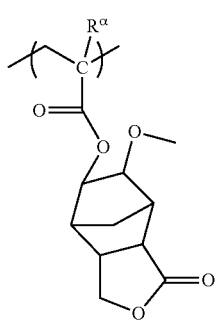
(a2-3-3)
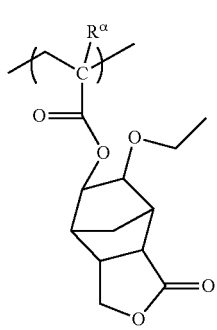
(a2-3-4)
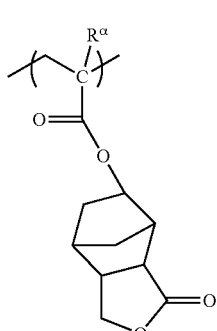
(a2-3-5)
[Chemical Formula 36]
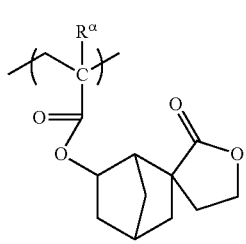
(a2-4-1)
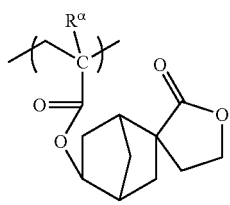
(a2-4-2)
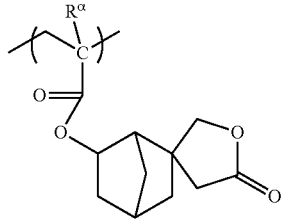
(a2-4-3)
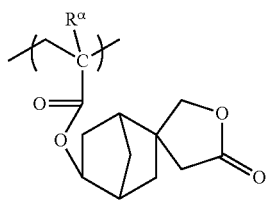
(a2-4-4)
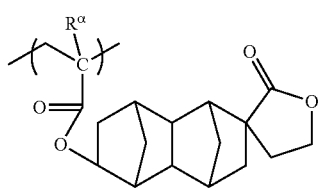
(a2-4-5)
(a2-4-6)
(a2-4-7)
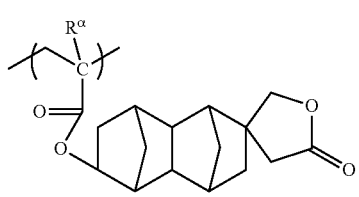
(a2-4-8)

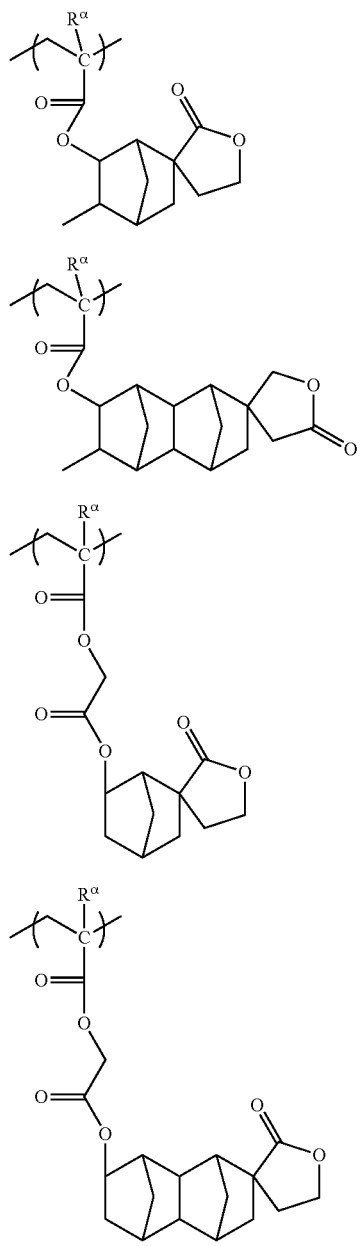
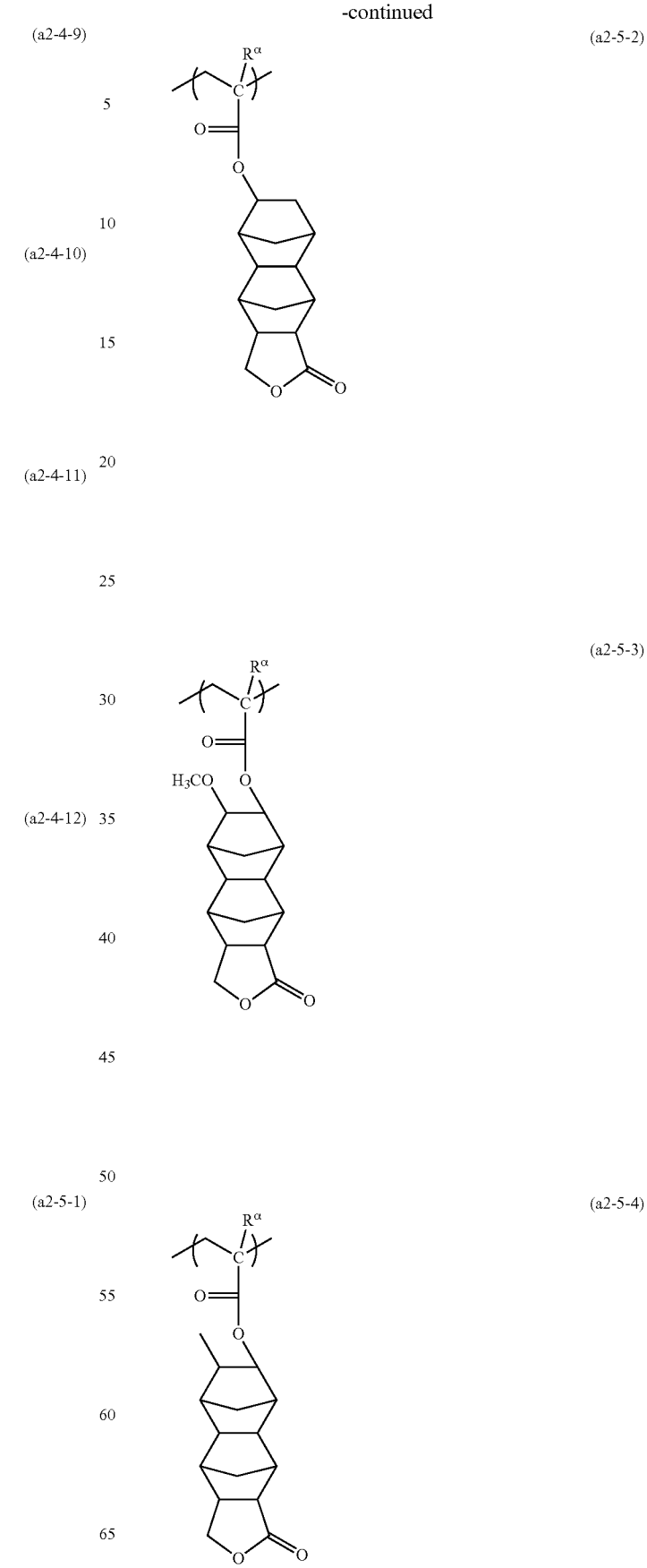

-continued (a2-5-5)

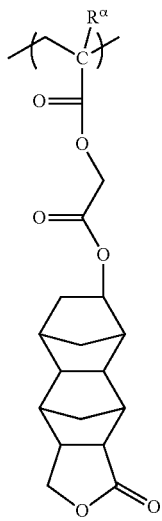

(a2-5-6)

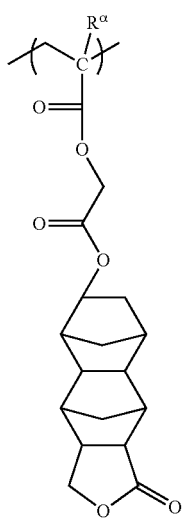

As the structural unit (a2$^L$), at least one structural unit selected from the group consisting of structural units represented by the aforementioned general formulas (a2-1) to (a2-5) is preferable, at least one structural unit selected from the group consisting of structural units represented by the aforementioned general formulas (a2-1) to (a2-3) is more preferable, and at least one structural unit selected from the group consisting of structural units represented by the aforementioned general formulas (a2-1) and (a2-2) is particularly desirable.

Of these, it is particularly preferable to use at least one structural unit selected from the group consisting of structural units represented by the aforementioned formulas (a2-1-1), (a2-1-2), (a2-2-1), (a2-2-7), (a2-2-12), (a2-2-14), (a2-3-1) and (a2-3-5).

In the component (A1), as the structural unit (a2), one type of structural unit may be used alone, or two or more types of structural units may be used in combination. For example, as the structural unit (a2), a structural unit (a2$^S$) may be used alone, or a structural unit (a2$^L$) may be used alone, or a combination of these structural units may be used. Further, as the structural unit (a2$^S$) or the structural unit (a2$^L$), either a single type of structural unit may be used, or two or more types may be used in combination.

In the component (A1), the amount of the structural unit (a2) based on the combined total of all structural units constituting the component (A1) is preferably 1 to 80 mol %, more preferably 10 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties, such as DOF and CDU, and pattern shape can be improved.

—Structural Unit (a3)

The structural unit (a3) is derived from an acrylate ester in which the hydrogen atom bonded to the carbon atom on the α-position may be substituted with a substituent, and is a structural unit derived from an acrylate ester containing a polar group-containing aliphatic hydrocarbon group.

When the component (A 1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 38]

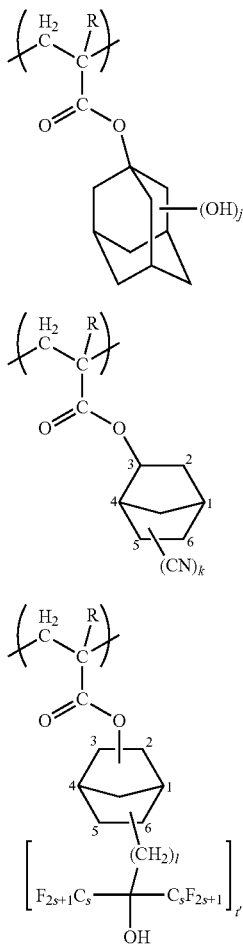

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group be bonded to the terminal of the carboxyl group of the acrylic acid. The fluorinated alkyl alcohol is preferably bonded to the 5th or 6th position of the norbornyl group.

In the component (A1), as the structural unit (a3), one type of structural unit may be used alone, or two or more types of structural units may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

—Structural Unit (a4)

The component (A1) may also include a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), for example, structural units derived from an acrylate ester in which the hydrogen atom bonded to the carbon atom on the α-position may be substituted with a substituent that are structural units derived from an acrylate ester containing a non-acid dissociable, aliphatic polycyclic group, or the like are preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a-4-1) to (a-4-5) shown below.

[Chemical Formula 39]

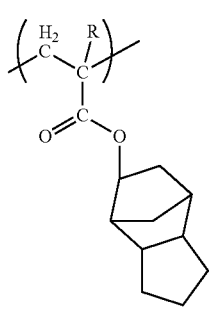

(a4-1)

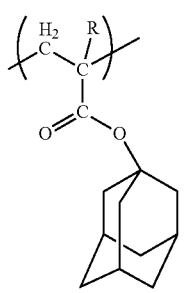

(a4-2)

-continued

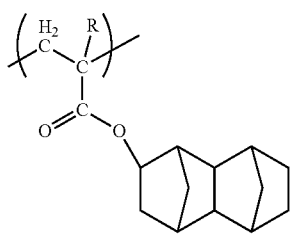
(a4-3)

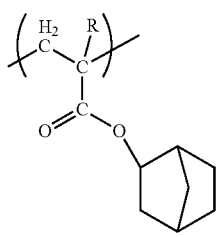
(a4-4)

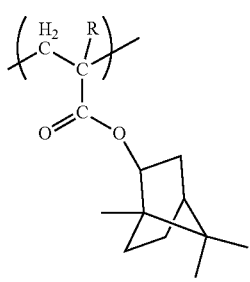
(a4-5)

In the formulas, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the resist composition of the present invention, the component (A1) is preferably a polymeric compound having a structural unit (a1).

Examples of the component (A1) include a copolymer consisting of the structural units (a1), (a2) and (a3); a copolymer consisting of the structural units (a1), (a2), (a3) and (a4); and a copolymer consisting of the structural units (a1) and (a3).

In the component (A1), each of the structural units may be composed of a plurality of different structural units.

In the component (A), as the component (A1), one type may be used alone, or two or more types may be used in combination.

In the present invention, as the component (A1), a polymeric compound that includes a combination of structural units such as that shown below is particularly desirable.

[Chemical Formula 40]

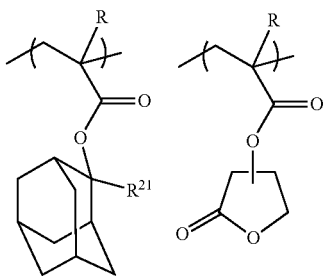
(A1-11)

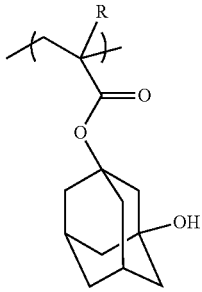

In the formulas, R and $R^{21}$ are the same as defined above, and the plurality of R may be the same or different from each other.

In formula (A1-11), as the alkyl group of 1 to 5 carbon atoms for $R^{21}$, the same alkyl groups of 1 to 5 carbon atoms as those described above for R can be used, and a methyl group or an ethyl group is preferable.

[Chemical Formula 41]

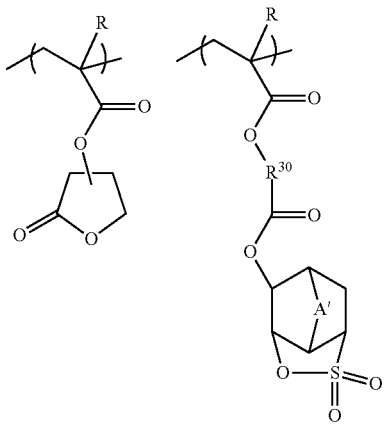
(A1-12)

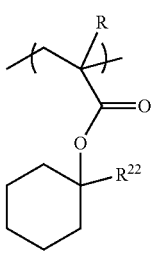

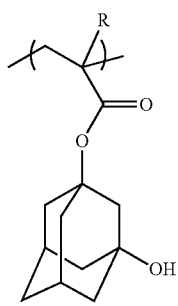

In the formulas, R, $R^{30}$, A', $R^{21}$ and $R^{22}$ are the same as defined above; and the plurality of R may be the same or different from each other.

[Chemical Formula 42]

(A1-13)

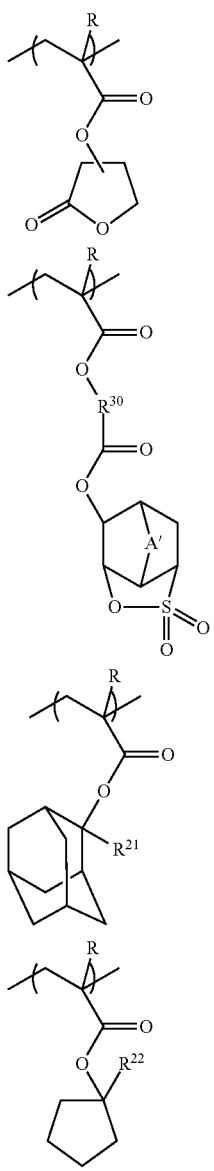

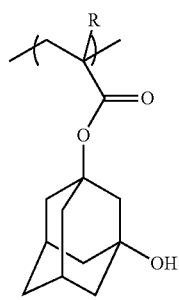

In the formulas, R, $R^{30}$, A', $R^{21}$ and $R^{22}$ are the same as defined above; and the plurality of R may be the same or different from each other.

[Chemical Formula 43]

(A1-14)

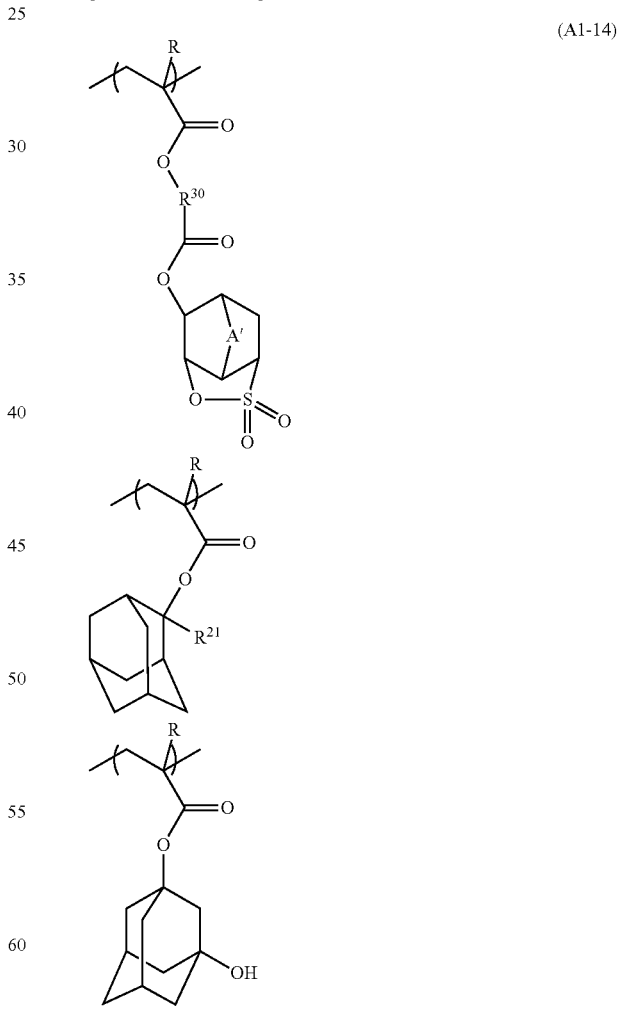

In the formulas, R, $R^{30}$, A' and $R^{21}$ are the same as defined above; and the plurality of R may be the same or different from each other.

[Chemical Formula 44]
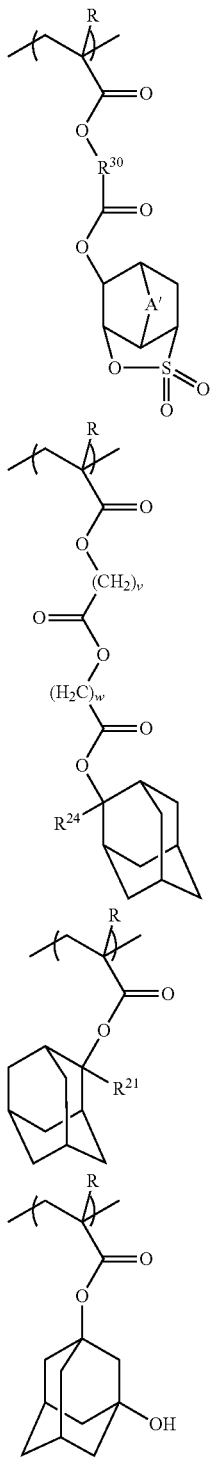
(A1-15)
In the formulas, R, R$^{30}$, A', v, w and R$^{21}$ are the same as defined above; and the plurality of R may be the same or different from each other.
[Chemical Formula 45]
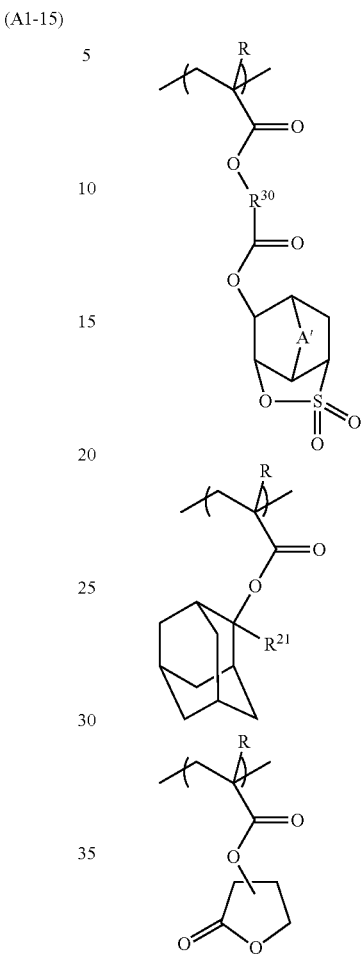
(A1-16)
In the formulas, R, R$^{30}$, A' and R$^{21}$ are the same as defined above; and the plurality of R may be the same or different from each other.
[Chemical Formula 46]
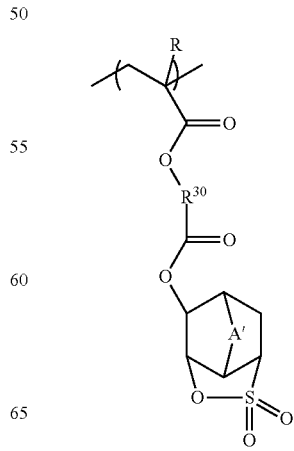
(A1-17)

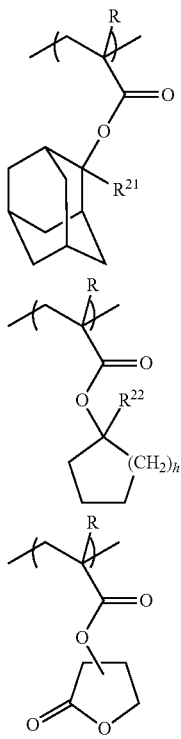

In the formulas, R, R³⁰, A', R²¹, R²² and h are the same as defined above; and the plurality of R may be the same or different from each other.

[Chemical Formula 47]

(A1-18)

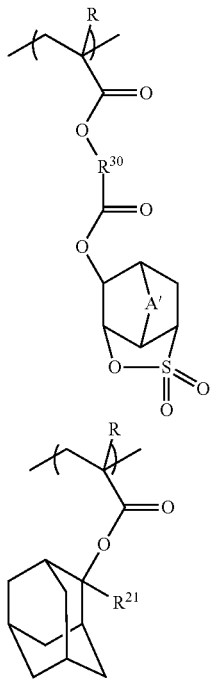

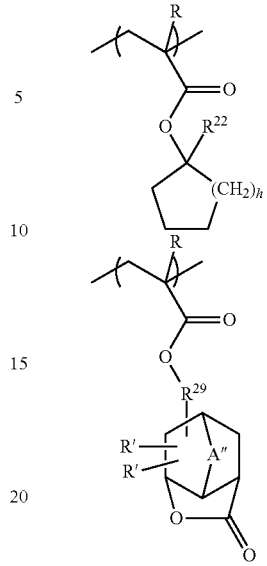

In the formulas, R, R³⁰, A', R²¹, R²², h, R²⁹, A" and R' are the same as defined above; and the plurality of R and R' may be the same or different from each other.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—CH$_2$—CH$_2$—CH$_2$—C(CF$_3$)$_2$—OH during the above polymerization, a —C(CF$_3$)$_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably within a range from 1,000 to 50,000, more preferably from 1,500 to 30,000, and most preferably from 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is preferably 1.0 to 5.0, more preferably 1.0 to 3.0, and most preferably 1.0 to 2.5. Here, Mn is the number average molecular weight.

In the resist composition of the present invention, the component (A) may contain "a base component which exhibits increased solubility in an alkali developing solution under the action of acid" other than the component (A1).

Such base component other than the component (A1) is not particularly limited, and any of the multitude of conventional base components used within chemically amplified resist compositions (e.g., a novolak resin, a polyhydroxystyrene-based resin (PHS), a low molecular weight compound (component (A2))) can be appropriately selected for use.

Examples of the component (A2) include low molecular weight compounds that have a molecular weight of at least 500 and less than 4,000, contains a hydrophilic group, and also contains an acid dissociable, dissolution inhibiting group described above in connection with the component (A1). Specific examples of the low molecular weight compound include compounds containing a plurality of phenol skeletons in which a part of the hydrogen atoms within hydroxyl groups have been substituted with the aforementioned acid dissociable, dissolution inhibiting groups.

In the resist composition of the present invention, as the component (A), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, a resist pattern exhibiting a high resolution and a high rectangularity can be easily formed.

In the resist composition of the present invention, the amount of the component (A) can be appropriately adjusted depending on the thickness of the resist film to be formed, and the like.

<Component (C)>

In the present invention, the component (C) includes a compound (C1) represented by general formula (c1) shown below (hereafter, referred to as "component (C1)"). In the present invention, the component (C) functions as an acid diffusion control agent, i.e., a quencher which traps the acid generated from the component (B) upon exposure.

Further, in the present invention, the component (C) may contain a nitrogen-containing organic compound (C2) (hereafter, referred to as component (C2)) which does not fall under the definition of component (C1).

[Chemical Formula 48]

(c1)

In the formula, $R^N$ represents a nitrogen-containing heterocyclic group which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $M^+$ represents an organic cation.

[Component (C1)]

The component (C1) is a compound consisting of an anion moiety and a cation moiety represented by formula (c1).

In formula (c1), $R^N$ represents a nitrogen-containing heterocyclic group which may have a substituent. Here, the term "nitrogen-containing heterocyclic group" refers to a heterocyclic group containing a nitrogen atom as the hetero atom. These nitrogen-containing heterocyclic groups may have, in addition to a substituent containing a nitrogen atom (hereafter, this group is referred to as "nitrogen-containing substituent"), a substituent that contains no nitrogen atom (hereafter, referred to as "non-nitrogen-containing substituent").

As the nitrogen-containing heterocyclic group for $R^N$, a monovalent group in which one hydrogen atom has been removed from a heterocyclic group containing a nitrogen atom as the hetero atom (i.e., a nitrogen-containing heterocyclic group) can be mentioned. Examples of the nitrogen-containing heterocyclic group include unsaturated, monocyclic nitrogen-containing hetero rings, such as pyridine, pyrrole, pyrazole, imidazole, 1,2,3-triazole, 1,2,4-triazole, tetrazole, pyrimidine, pyrazine and 1,3,5-triazine; saturated, monocyclic nitrogen-containing hetero rings, such as piperidine, piperazine and pyrrolidine; and polycyclic nitrogen-containing hetero rings, such as quinoline, isoquinoline, indole, pyrrolo[2,3-b]pyridine, indazole, benzimidazole, benzotriazole, carbazole, acridine, 1,5-diazabicyclo[4.3.0]-5-nonene, 1,8-diazabicyclo[5.4.0]-7-undecene, hexamethylenetetramine and 1,4-diazabicyclo[2.2.2]octane. The nitrogen-containing heterocyclic group may be either a monocyclic group or a polycyclic group, and is preferably a group that has aromaticity. The nitrogen-containing heterocyclic group has 3 to 30 carbon atoms, more preferably 5 to 30 carbon atoms, and still more preferably 5 to 20 carbon atoms.

Examples of the nitrogen-containing substituent for $R^N$ include the aforementioned nitrogen-containing heterocyclic group, as well as an amino group (—$NH_2$), an imino group (HN=), a cyano group (N≡C—) and an ammonio group ($^+NH_3$—). These nitrogen-containing substituents may have part or all of the hydrogen atoms substituted with a non-nitrogen-containing substituent.

Specific examples of the nitrogen-containing substituent for $R^N$ include nitrogen-containing heterocyclic groups, such as a 2-pyridyl group, a 3-pyridyl group, a 4-pyridyl group and a piperidino group; an amino group; an alkylamino group; a dialkylamino group; an imino group; an alkylimino group; a cyano group; and a trialkylammonio group.

Examples of the non-nitrogen-containing substituent for $R^N$ include an alkyl group, an aryl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

Examples of aryl groups include a phenyl group, a tolyl group and a naphthyl group.

Examples of the halogen atoms include a fluorine atom, a chlorine atom, an iodine atom and a bromine atom.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

Preferred examples of the groups represented by $R^N$—C(=O)—O— in the above formula (c1) include those shown below.

[Chemical Formula 49]
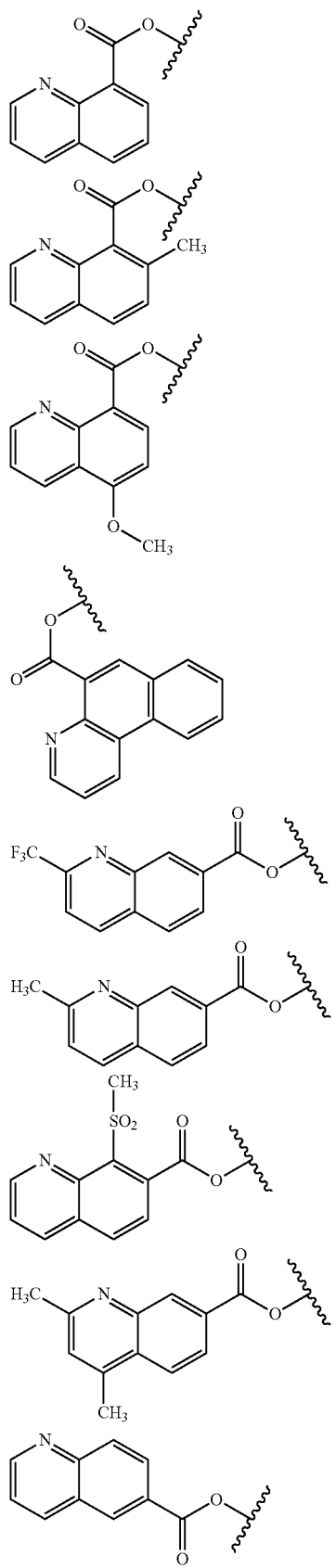
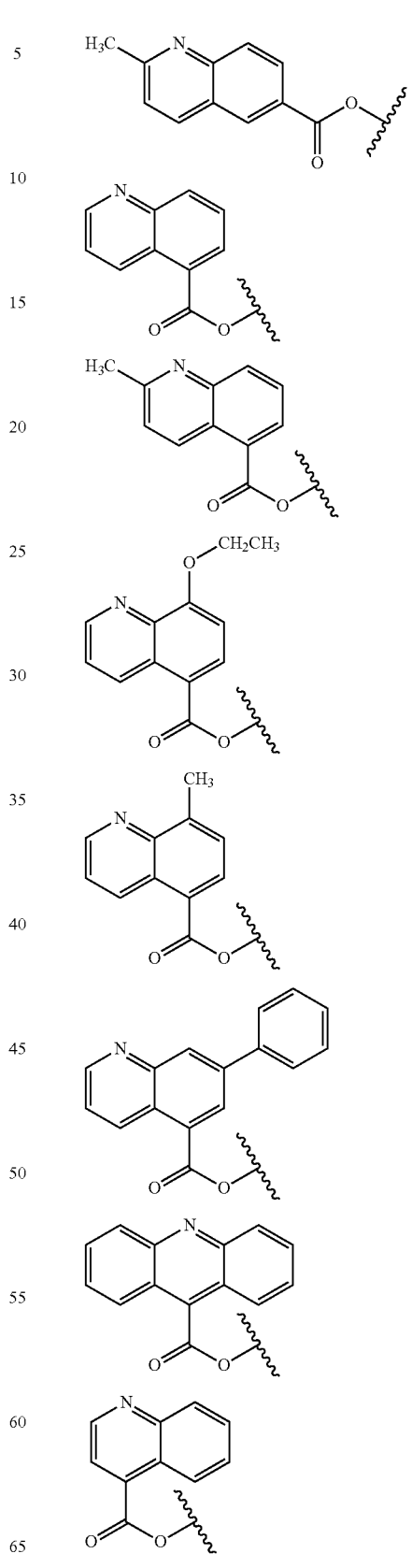

[Chemical Formula 50]

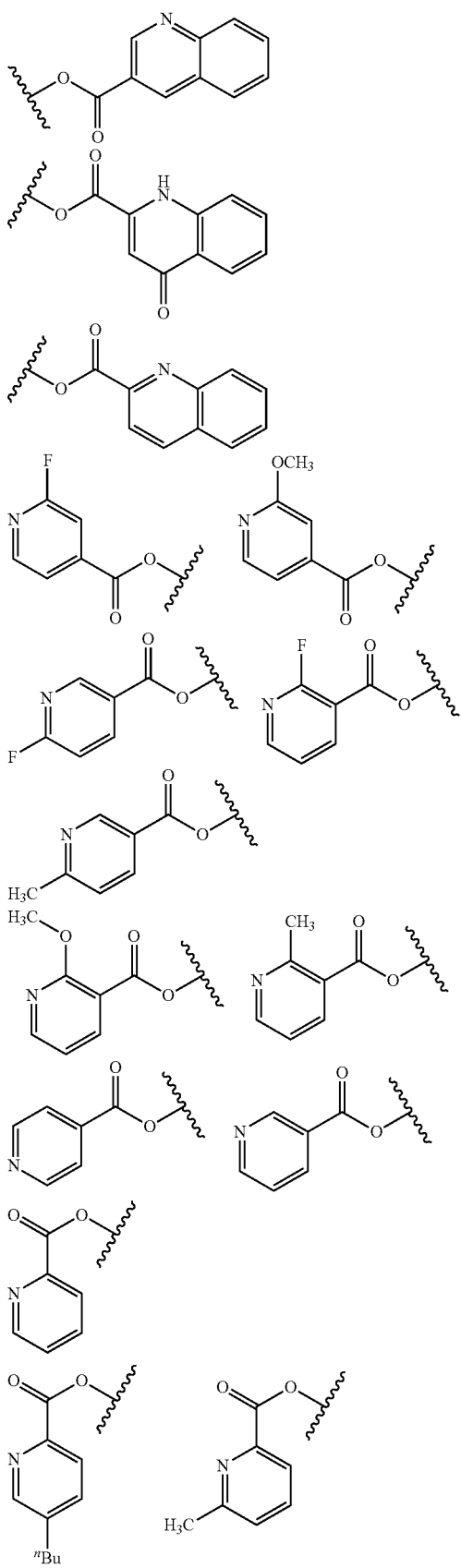

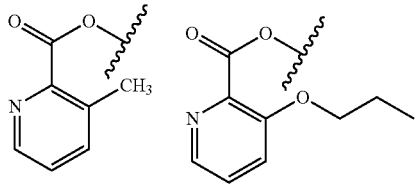

In formula (c1), $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms.

Here, an "aliphatic hydrocarbon group" refers to a hydrocarbon group that has no aromaticity. Further, the aliphatic hydrocarbon group may be saturated or unsaturated. In general, the aliphatic hydrocarbon group is preferably saturated.

The linear or branched divalent aliphatic hydrocarbon group of 1 to 10 carbon atoms for $X^0$ preferably has 1 to 8 carbon atoms, more preferably 1 to 5 carbon atoms, and still more preferably 1 or 2 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as -$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon groups in which some or all of the hydrogen atoms have been substituted with fluorine atoms for $X^0$ are preferably fluorinated alkylene groups.

Specific examples of the fluorinated alkylene groups include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, -$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

The cyclic divalent aliphatic hydrocarbon group of 3 to 20 carbon atoms for $X^o$ refers to a group in which two hydrogen atoms have been removed from an aliphatic hydrocarbon ring.

The divalent aliphatic hydrocarbon group of 3 to 20 carbon having a cyclic partial structure for $X^o$ refers to a group in which the aforementioned cyclic divalent aliphatic hydrocarbon group is either bonded to the terminal of an aforementioned chain-like aliphatic hydrocarbon group, or interposed within the chain of an aforementioned chain-like aliphatic hydrocarbon group.

The cyclic divalent aliphatic hydrocarbon group of 3 to 20 carbon atoms or divalent aliphatic hydrocarbon group of 3 to 20 carbon having a cyclic partial structure preferably has 3 to 12 carbon atoms.

The cyclic divalent aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic divalent aliphatic hydrocarbon group or divalent aliphatic hydrocarbon having a cyclic partial structure may have some or all of the hydrogen atoms substituted with fluorine atoms.

In the present invention, the component (C1) is preferably represented by formula (c1-1) shown below.

[Chemical Formula 51]

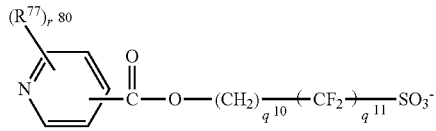

(c1-1)

In the formula, $q^{10}$ represents an integer of 1 to 9; $q^{11}$ represents an integer of 1 to 9; provided that $q^{10}+q^{11}$ is an integer of 2 to 9; $r^{80}$ represents an integer of 0 to 3; and $R^{77}$ represents a substituent.

As the substituent for $R^{77}$, the same groups as those which the aforementioned nitrogen-containing heterocyclic group for $R^N$ may have as a substituent can be used.

When $r^{80}$ represents an integer of 2 or more, then the plurality of the $R^{77}$ groups within this compound may be the same or different from each other.

$q^{10}$ is preferably 1 or 2.

q" is preferably 1 or 2.

$r^{80}$ is preferably an integer of 0 to 2, and more preferably 0 or 1.

In formula (c1), $M^+$ represents an organic cation.

In the above formula (c1), as the organic cation for $M^+$, there is no particular limitation, and any of those conventionally known as cation moiety for an onium salt-based acid generator can be appropriately selected for use.

As the cation moiety, a sulfonium ion or an iodonium ion is preferable, and a sulfonium ion is particularly desirable.

Preferred examples of the organic cations for $Z^+$ include organic cations represented by general formulas (b1-c1) and (b1-c2) shown below.

[Chemical Formula 52]

In the formulas, each of $R^{1'''}$ to $R^{3'''}$, $R^{5'''}$ and $R^{6'''}$ independently represents an aryl group which may have a substituent, an alkyl group or an alkenyl group, with the provision that at least one of $R^{1'''}$ to $R^{3'''}$ represents an aryl group, and at least one of $R^{5'''}$ and $R^{6'''}$ represents an aryl group. In formula (b1-c1), two of $R^{1'''}$ to $R^{3'''}$ may be bonded to each other to form a ring with the sulfur atom in the formula.

In the above formula (b1-c1), each of $R^{1'''}$ to $R^{3'''}$ independently represents an aryl group which may have a substituent, an alkyl group or an alkenyl group. Two of $R^{1'''}$ to $R^{3'''}$ may be bonded to each other to form a ring with the sulfur atom in the formula.

Further, among $R^{1'''}$ to $R^{3'''}$, at least one group represents an aryl group. Among $R^{1'''}$ to $R^{3'''}$, two or more groups are preferably aryl groups, and it is particularly desirable that all of $R^{1'''}$ to $R^{3'''}$ are aryl groups.

Examples the aryl group for $R^{1'''}$ to $R^{3'''}$ include unsubstituted aryl groups of 6 to 20 carbon atoms, and substituted aryl groups in which a part or all of the hydrogen atoms of the aforementioned unsubstituted aryl groups has been substituted with alkyl groups, alkoxy groups, alkoxyalkyloxy groups, alkoxycarbonylalkyloxy groups, halogen atoms, hydroxyl groups, oxo groups (=O), aryl groups, —C(=O)—O—$R^{6'}$, —O—C(=O)—$R^{7'}$, —O—$R^{8'}$, or the like.

Each of $R^{6'}$, $R^{7'}$ and $R^{8'}$ represents a linear or branched saturated hydrocarbon group of 1 to 25 carbon atoms, a cyclic saturated hydrocarbon group of 3 to 20 carbon atoms, or a linear or branched aliphatic unsaturated hydrocarbon group of 2 to 5 carbon atoms.

The linear or branched saturated hydrocarbon group has 1 to 25 carbon atoms, preferably 1 to 15 carbon atoms, and more preferably 4 to 10 carbon atoms.

Examples of the linear, saturated hydrocarbon group include a methyl group, an ethyl group, a propyl group, a butyl group, a pentyl group, a hexyl group, a heptyl group, an octyl group, a nonyl group and a decyl group.

Examples of the branched saturated hydrocarbon groups include, but excluding tertiary alkyl groups, a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The linear or branched saturated hydrocarbon group may have a substituent. Examples of the substituent include an alkoxy group, a halogen atom, a halogenated alkyl group, a hydroxyl group, an oxygen atom (=O), a cyano group and a carboxyl group.

The alkoxy group as the substituent for the linear or branched saturated hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the linear or branched saturated hydrocarbon group include a fluorine atom, a chlorine atom, a bromine atom and an iodine atom, and a fluorine atom is preferable.

Example of the halogenated alkyl group as the substituent for the linear or branched saturated hydrocarbon group includes a group in which a part or all of the hydrogen atoms within the aforementioned linear or branched saturated hydrocarbon group have been substituted with the aforementioned halogen atoms.

The cyclic saturated hydrocarbon group of 3 to 20 carbon atoms for $R^{6'}$, $R^{7'}$ and $R^{8'}$ may be either a polycyclic group or a monocyclic group. Examples thereof include groups in which one hydrogen atom has been removed from a monocycloalkane or a polycycloalkane (e.g., a bicycloalkane, a tricycloalkane or a tetracycloalkane). Specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

The cyclic saturated hydrocarbon group may have a substituent. For example, part of the carbon atoms constituting the ring within the cyclic alkyl group may be substituted with a hetero atom, or a hydrogen atom bonded to the ring within the cyclic alkyl group may be substituted with a substituent.

In the former example, a heterocycloalkane in which part of the carbon atoms constituting the ring within the aforementioned monocycloalkane or polycycloalkane has been substituted with a hetero atom such as an oxygen atom, a sulfur atom or a nitrogen atom, and one or more hydrogen atoms have been removed therefrom, can be used. Further, the ring may contain an ester bond (—C(=O)—O—). More specific examples include a lactone-containing monocyclic group, such as a group in which one hydrogen atom has been removed from γ-butyrolactone; and a lactone-containing polycyclic group, such as a group in which one hydrogen atom has been removed from a bicycloalkane, tricycloalkane or tetracycloalkane containing a lactone ring.

In the latter example, as the substituent, the same substituent groups as those for the aforementioned linear or branched alkyl group can be used.

Alternatively, $R^{6'}$, $R^{7'}$ and $R^{8'}$ may be a combination of a linear or branched alkyl group and a cyclic alkyl group.

Examples of the combination of a linear or branched alkyl group and a cyclic alkyl group include groups in which a cyclic alkyl group as a substituent is bonded to a linear or branched alkyl group, and groups in which a linear or branched alkyl group as a substituent is bonded to a cyclic alkyl group.

Examples of the linear aliphatic unsaturated hydrocarbon groups for $R^{6'}$, $R^{7'}$ and $R^{8'}$ include a vinyl group, a propenyl group (an allyl group) and a butynyl group.

Examples of the branched aliphatic unsaturated hydrocarbon groups for $R^{6'}$, $R^{7'}$ and $R^{8'}$ include a 1-methylpropenyl group and a 2-methylpropenyl group.

The aforementioned linear or branched, aliphatic unsaturated hydrocarbon group may have a substituent. Examples of substituents include the same substituents as those which the aforementioned linear or branched alkyl group may have.

Among the aforementioned examples, as $R^{7'}$ and $R^{8'}$, in terms of the improvements in lithography properties and shape of the resist pattern, a linear or branched saturated hydrocarbon group of 1 to 15 carbon atoms or a cyclic saturated hydrocarbon group of 3 to 20 carbon atoms is preferable.

The unsubstituted aryl group for $R^{1''}$ to $R^{3''}$ is preferably an aryl group having 6 to 10 carbon atoms because it can be synthesized at a low cost. Specific examples thereof include a phenyl group and a naphthyl group.

The alkyl group as the substituent for the substituted aryl group for $R^{1''}$ to $R^{3''}$ is preferably an alkyl group having 1 to 5 carbon atoms, and most preferably a methyl group, an ethyl group, a propyl group, an n-butyl group, or a tert-butyl group.

The alkoxy group as the substituent for the substituted aryl group is preferably an alkoxy group having 1 to 5 carbon atoms, and most preferably a methoxy group, ethoxy group, n-propoxy group, iso-propoxy group, n-butoxy group or tert-butoxy group.

The halogen atom as the substituent for the substituted aryl group is preferably a fluorine atom.

As the aryl group within the substituted aryl group, the same aryl groups as those listed for $R^{1''}$ to $R^{3''}$ can be used, and aryl groups of 6 to 20 carbon atoms are preferred, aryl groups of 6 to 10 carbon atoms are more preferred, and a phenyl group or a naphthyl group is still more preferred.

Examples of the alkoxyalkyloxy group as the substituent for the substituted aryl group include a group represented by a general formula: —O—C($R^{47}$)($R^{48}$)—O—$R^{49}$ (wherein each of $R^{47}$ and $R^{48}$ independently represents a hydrogen atom or a linear or branched alkyl group; and $R^{49}$ represents an alkyl group).

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ be a hydrogen atom, and it is particularly desirable that either one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of polycycloalkane include adamantane, norbornane, isobornane, tricyclodecane and tetracyclododecane. Among these, a group in which one or more hydrogen atoms have been removed from adamantane is preferable.

An example of the alkoxycarbonylalkyloxy group as the substituent for the substituted aryl group includes a group represented by a general formula: —O—$R^{50}$—C(=O)—O—$R^{56}$ [wherein $R^{50}$ represents a linear or branched alkylene group; and $R^{56}$ represents a tertiary alkyl group].

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

Examples of the tertiary alkyl groups for $R^{56}$ include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

Further, a group in which $R^{56}$ in the group represented by the aforementioned general formula: —O—$R^{50}$—C(=O)—O—$R^{56}$ has been substituted with $R^{56'}$ can also be used. $R^{56'}$ represents a hydrogen atom, a fluorinated alkyl group or an aliphatic cyclic group which may contain a hetero atom.

Examples of the fluorinated alkyl group for $R^{56'}$ include groups in which part or all of the hydrogen atoms within the alkyl group for $R^{49}$ has been substituted with fluorine atoms.

Examples of the aliphatic cyclic group which may contain a hetero atom for $R^{56'}$ include an aliphatic cyclic group which does not contain a hetero atom, an aliphatic cyclic group containing a hetero atom in the ring structure, and an aliphatic cyclic group in which a hydrogen atom has been substituted with a hetero atom.

As an aliphatic cyclic group which does not contain a hetero atom for $R^{56'}$, a group in which one or more hydrogen atoms have been removed from a monocycloalkane or a polycycloalkane such as a bicycloalkane, a tricycloalkane or a tetracycloalkane can be mentioned. Examples of the monocycloalkane include cyclopentane and cyclohexane. Examples of polycycloalkane include adamantane, norbornane, isobornane, tricyclodecane and tetracyclododecane. Among these, a group in which one or more hydrogen atoms have been removed from adamantane is preferable.

Specific examples of the aliphatic cyclic group containing a hetero atom in the ring structure for $R^{56'}$ include groups represented by formulas (L1) to (L6) and (S1) to (S4) described later.

Specific examples of the aliphatic cyclic group in which a hydrogen atom has been substituted with a hetero atom for $R^{56'}$ include an aliphatic cyclic group in which a hydrogen atom has been substituted with an oxygen atom (=O).

The aryl group for $R^{1'''}$ to $R^{3'''}$ is preferably a phenyl group or a naphthyl group.

Examples of the alkyl group for $R^{1'''}$ to $R^{3'''}$ include linear, branched or cyclic alkyl groups of 1 to 10 carbon atoms. Among these, in terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

The alkenyl group for $R^{1'''}$ to $R^{3'''}$ preferably has 2 to 10 carbon atoms, more preferably 2 to 5 carbon atoms, and still more preferably 2 to 4 carbon atoms. Specific examples thereof include a vinyl group, a propenyl group (an allyl group), a butynyl group, a 1-methylpropenyl group and a 2-methylpropenyl group.

When two of $R^{1'''}$ to $R^{3'''}$ are bonded to each other to form a ring with the sulfur atom in the formula, it is preferable that the two of $R^{1'''}$ to $R^{3'''}$ form a 3 to 10-membered ring including the sulfur atom, and it is particularly desirable that the two of $R^{1'''}$ to $R^{3'''}$ form a 5 to 7-membered ring including the sulfur atom.

When two of $R^{1'''}$ to $R^{3'''}$ are bonded to each other to form a ring with the sulfur atom in the formula, the remaining one of $R^{1'''}$ to $R^{3'''}$ is preferably an aryl group. As examples of the aryl group, the same as the above-mentioned aryl groups for $R^{1'''}$ to $R^{3'''}$ can be given.

Specific examples of the organic cation represented by the above general formula (b1-c1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl) diphenylsulfonium, (4-(2-methyl-2-adamantyloxycarbonylmethyloxy)phenyl)diphenylsulfonium, (4-(2-methyl-2-adamantyloxycarbonylmethyloxy)-3,5-dimethylphenyl) diphenylsulfonium, tri(4-methylphenyl)sulfonium, dimethyl (4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl) phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl) tetrahydrothiopyranium and 1-(4-methylphenyl)tetrahydrothiopyranium.

Further, preferred examples of the organic cation represented by the above formula (b1-c1) include those shown below.

[Chemical Formula 53]

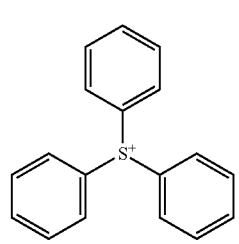

(b1-c1-1)

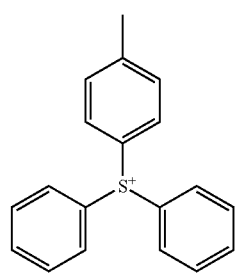

(b1-c1-2)

(b1-c1-3)
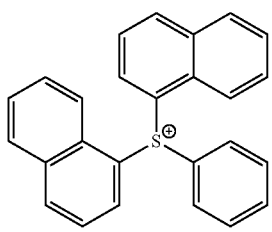
[Chemical Formula 54]
(b1-c1-4)
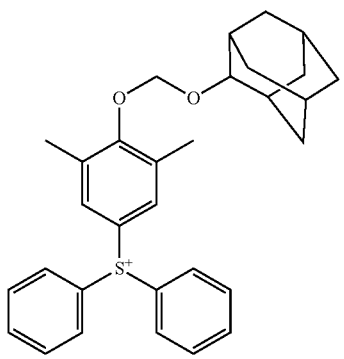
(b1-c1-5)
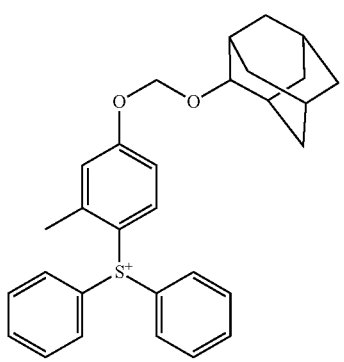
(b1-c1-6)
[Chemical Formula 55]
(b1-c1-7)
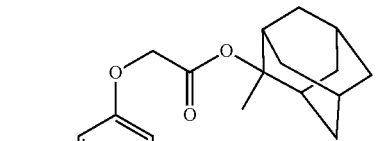
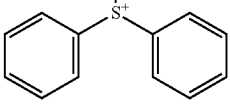
(b1-c1-8)
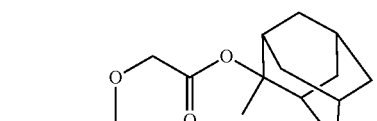
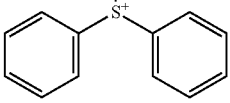
(b1-c1-9)
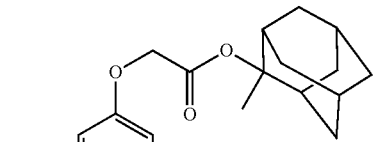
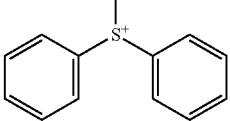
(b1-c1-10)
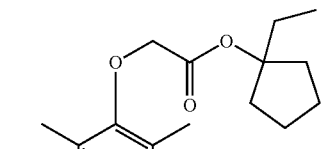
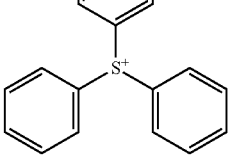

(b1-c1-11)
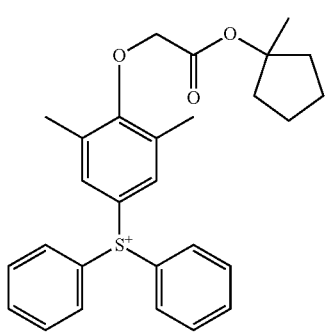
(b1-c1-12)
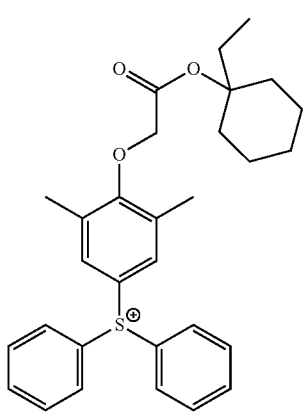
(b1-c1-13)
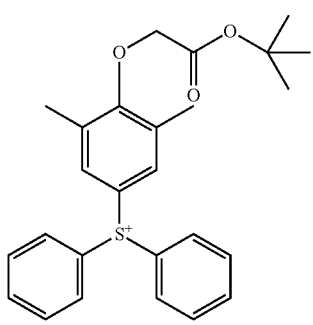
[Chemical Formula 56]
(b1-c1-14)
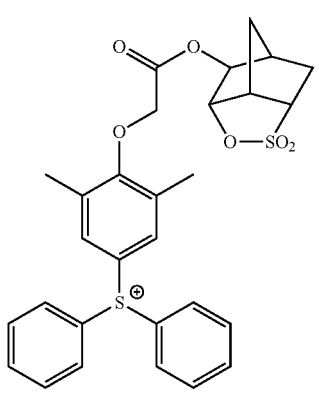
(b1-c1-15)
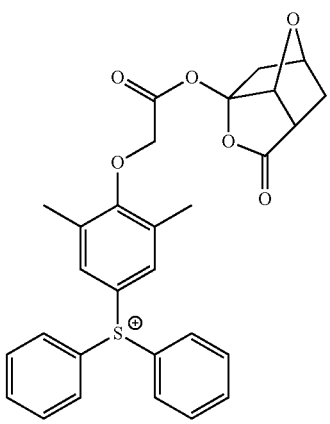
(b1-c1-16)
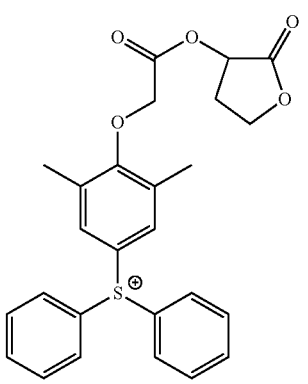
(b1-c1-17)
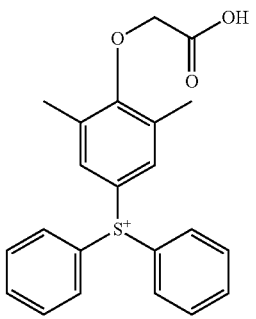
(b1-c1-18)

(b1-c1-19)
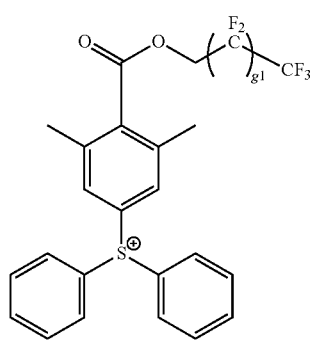
In the formula, g1 represents a recurring number, and is an integer of 1 to 5.
[Chemical Formula 57]
(b1-c1-20)
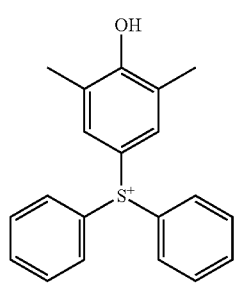
(b1-c1-21)
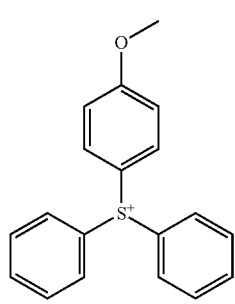
(b1-c1-22)
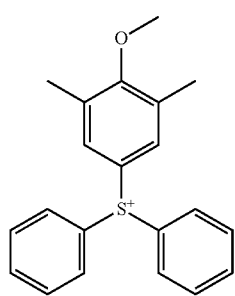
[Chemical Formula 58]
(b1-c1-23)
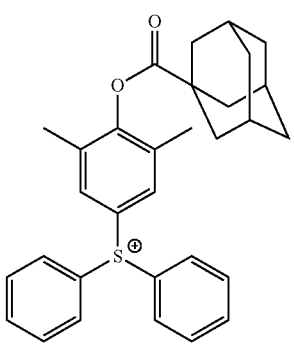
(b1-c1-24)
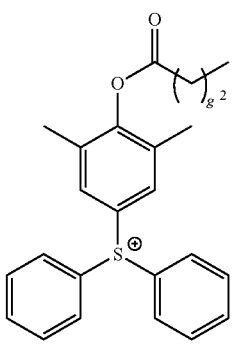
(b1-c1-25)
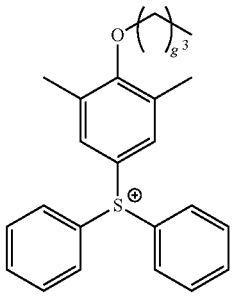
In the formula, g2 and g3 represent recurring numbers, wherein g2 is an integer of 0 to 20, and g3 is an integer of 0 to 20.
[Chemical Formula 59]
(b1-c1-26)
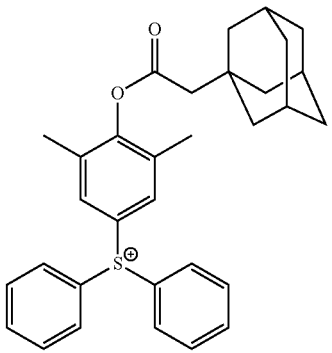

(b1-c1-27)
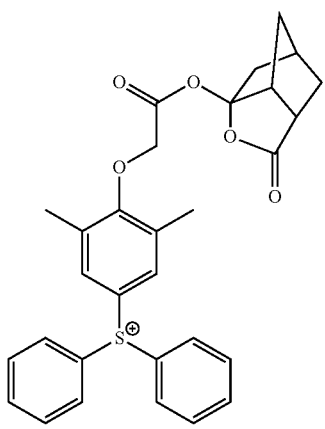

(b1-c1-28)
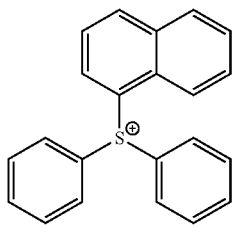

[Chemical Formula 60]

(b1-c1-29)
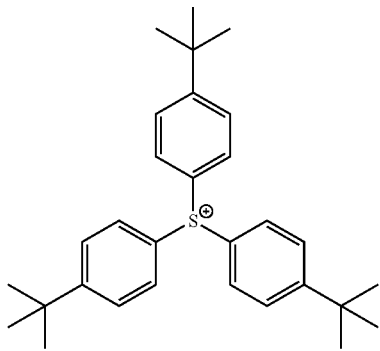 [SMILES: CC(C)(C)c1ccc([S+](c2ccc(C(C)(C)C)cc2)c2ccc(C(C)(C)C)cc2)cc1]

(b1-c1-30)
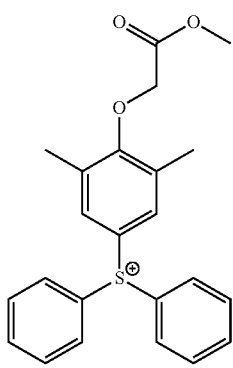 [SMILES: COC(=O)COc1c(C)cc([S+](c2ccccc2)c2ccccc2)cc1C]

(b1-c1-31)
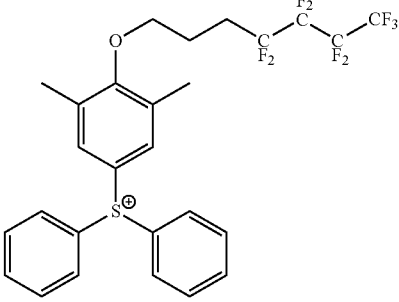

[Chemical Formula 61]

(b1-c1-32)
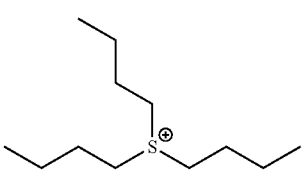

(b1-c1-33)
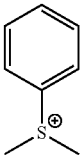

In the above formula (b1-c2), each of $R^{5''}$ and $R^{6''}$ independently represents an aryl group which may have a substituent, an alkyl group or an alkenyl group.

At least one of $R^{5''}$ and $R^{6''}$ represents an aryl group. It is preferable that both of $R^{5''}$ and $R^{6''}$ represent an aryl group.

As the aryl group for $R^{5''}$ and $R^{6''}$, the same as the aryl groups for $R^{1''}$ to $R^{3''}$ can be used.

As the alkyl group for $R^{5''}$ and $R^{6''}$, the same as the alkyl groups for $R^{1''}$ to $R^{3''}$ can be used.

As the alkenyl group for $R^{5''}$ and $R^{6''}$, the same as the alkenyl groups for $R^{1''}$ to $R^{3''}$ can be used.

It is particularly desirable that both of $R^{5''}$ and $R^{6''}$ represents a phenyl group.

Specific examples of the cation moiety represented by general formula (b1-c2) above include diphenyliodonium and bis(4-tert-butylphenyl)iodonium.

Further, preferred examples of the monovalent organic cation for M⁺ also include the cations represented by general formulas (I-1) and (I-2) shown below.

[Chemical Formula 62]

(I-1)
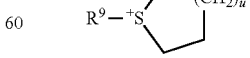

(I-2)
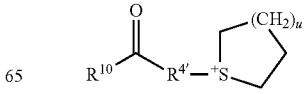

In formulas (I-1) and (I-2), each of $R^9$ and $R^{10}$ independently represents a phenyl group or naphthyl group which may have a substituent, an alkyl group of 1 to 5 carbon atoms, an alkoxy group or a hydroxyl group. Examples of the substituents are the same as the substituents described above for the substituted aryl group in relation to the aryl group for $R^{1''}$ to $R^{3''}$ (i.e., an alkyl group, an alkoxy group, an alkoxyalkyloxy group, an alkoxycarbonylalkyloxy group, a halogen atom, a hydroxyl group, an oxo group (=O), an aryl group, —C(=O)—O—$R^{6'}$, —O—C(=O)—$R^{7'}$, —O—$R^{8'}$, and a group in which $R^{56}$ in the aforementioned general formula —O—$R^{50}$—C(=O)—O—$R^{56}$ has been substituted with $R^{56'}$).

$R^{4'}$ represents an alkylene group of 1 to 5 carbon atoms.

u represents an integer of 1 to 3, and is most preferably 1 or 2.

Preferred examples of the organic cation represented by the above formula (I-1) or (I-2) include those shown below.

[Chemical Formula 63]

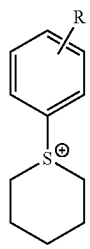

(I-1-1)

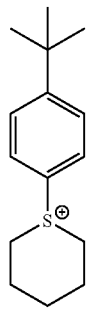

(I-1-2)

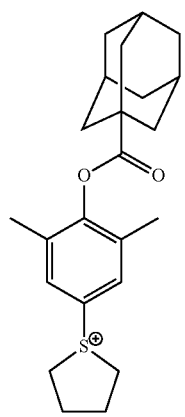 [SMILES: Cc1cc([S+]2CCCC2)cc(C)c1OC(=O)C12CC3CC(CC(C3)C1)C2]

(I-1-3)

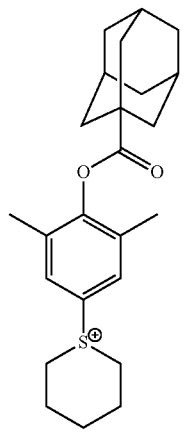 [SMILES: Cc1cc([S+]2CCCCC2)cc(C)c1OC(=O)C12CC3CC(CC(C3)C1)C2]

(I-1-4)

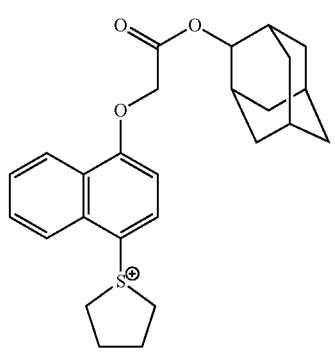

(I-1-5)

[Chemical Formula 64]

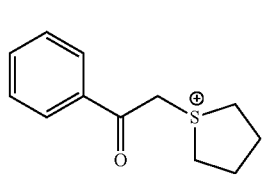

(I-2-1)

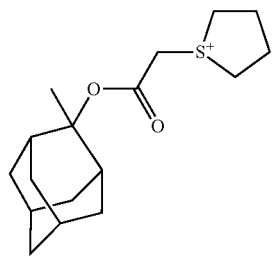

(I-2-2)

Further, preferred examples of the monovalent organic cation for $M^+$ also include the cations represented by general formulas (I-5) and (I-6) shown below.

[Chemical Formula 65]

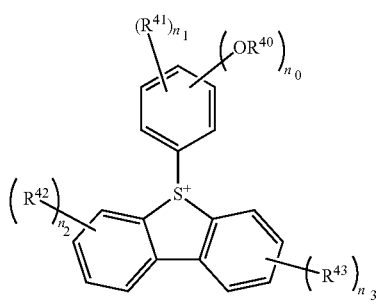

(I-5)

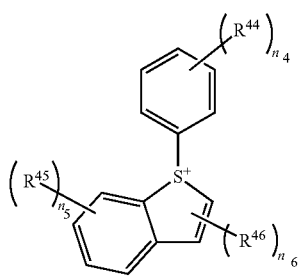

(I-6)

In the formulas, $R^{40}$ represents a hydrogen atom or an alkyl group; $R^{41}$ represents an alkyl group, an acetyl group, a carboxyl group or a hydroxyalkyl group; each of $R^{42}$ to $R^{46}$ independently represents an alkyl group, an acetyl group, an alkoxy group, a carboxyl group or a hydroxyalkyl group; each of $n_0$ to $n_5$ independently represents an integer of 0 to 3, with the proviso that $n_0+n_1$ is 5 or less; and $n_6$ represents an integer of 0 to 2.

In general formula (I-5), the alkyl group for $R^{40}$ is preferably an alkyl group of 1 to 15 carbon atoms, more preferably an alkyl group of 1 to 10 carbon atoms, still more preferably an alkyl group of 4 to 10 carbon atoms, and a linear or branched alkyl group is particularly desirable.

In general formulas (I-5) and (I-6), with respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

When the subscript n0 of $OR^{40}$ represent an integer of 2 or more, then the two or more of the individual $OR^{40}$ group may be the same or different from each other.

When the subscripts n1 to n6 of $R^{41}$ to $R^{46}$ represent an integer of 2 or more, the plurality of $R^{41}$ to $R^{46}$ may be the same or different.

$n_0$ is preferably 0 or 1.

$n_1$ is preferably 0 to 2.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1.

Preferred examples of the organic cation represented by the above formula (I-5) or (I-6) include the cations shown below.

[Chemical Formula 66]

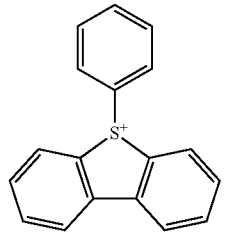

(I-5-1)

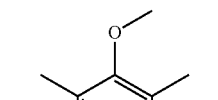

(I-5-2)

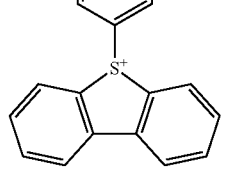

(I-5-3)

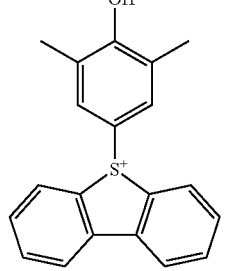

(I-5-4)

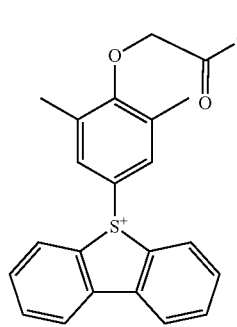

-continued
(I-5-5)
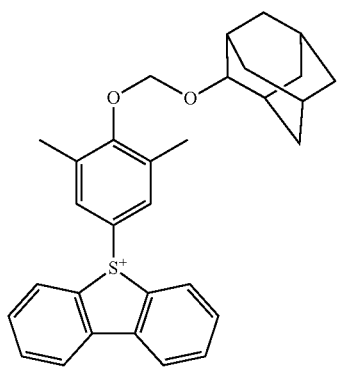
(I-5-6)
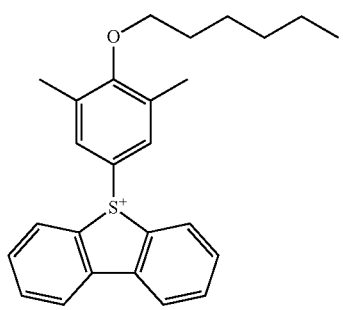
(I-6-1)
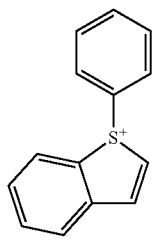
(I-6-2)
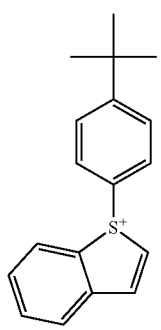
Further, preferred examples of the monovalent organic cation for Z⁺ also include the cations shown below.
[Chemical Formula 67]
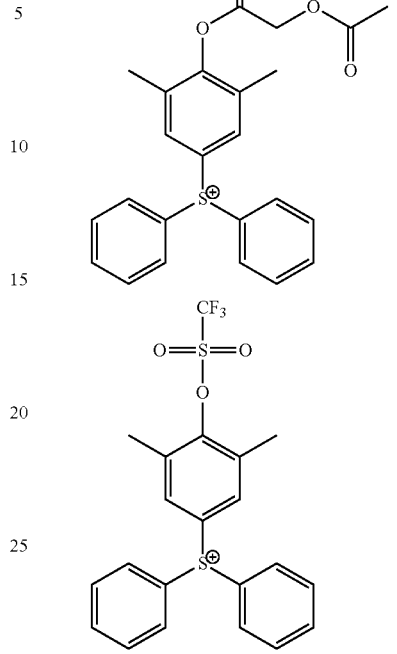
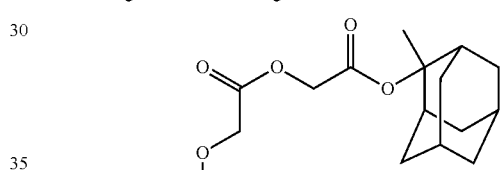
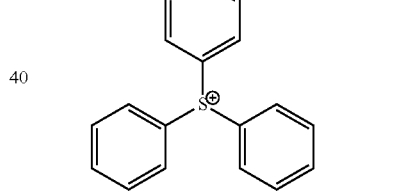
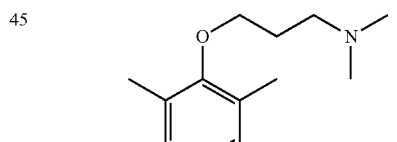
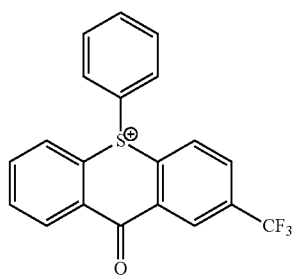

-continued
[Chemical Formula 68]
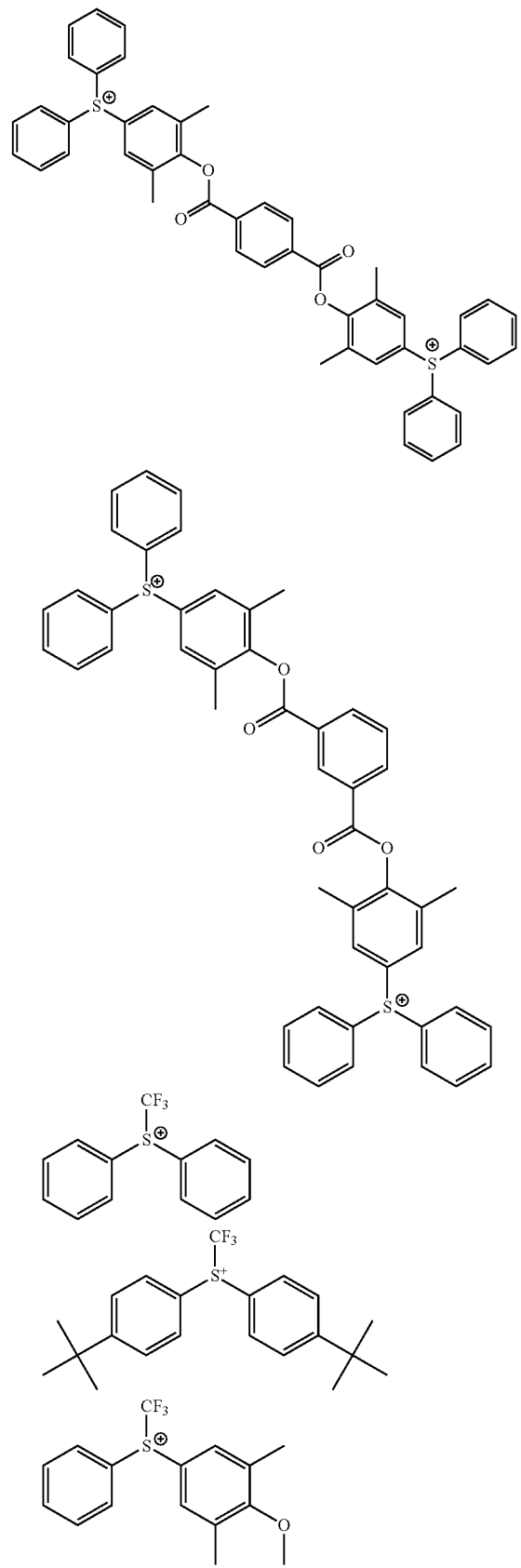
-continued
[Chemical Formula 69]
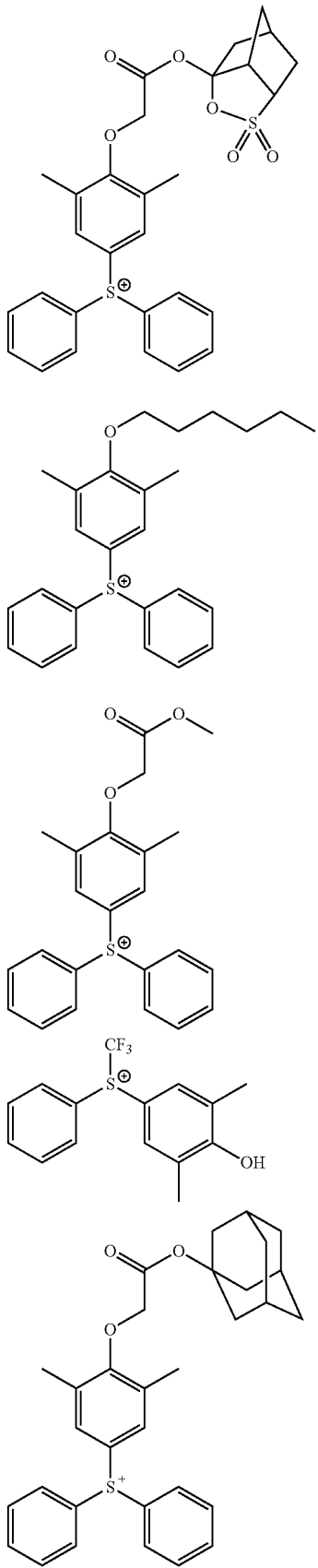

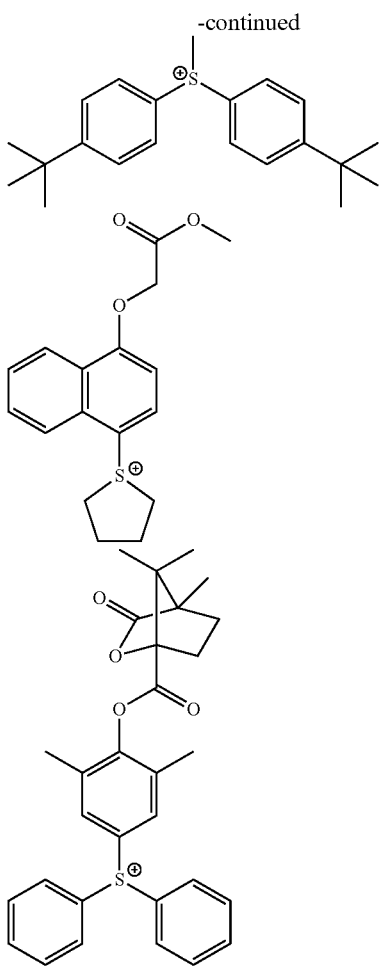

As the component (C1), one type of compound may be used alone, or two or more types of compounds may be used in combination.

The amount of the component (C1) relative to 100 parts by weight of the component (A) is preferably within a range from 0.5 to 15 parts by weight, more preferably from 0.5 to 12 parts by weight, and still more preferably from 1.0 to 10 parts by weight. When the amount of the component (C1) is at least as large as the lower limit of the above-mentioned range, various lithography properties of the resist composition are improved, such as roughness, mask reproducibility and exposure latitude. Further, a resist pattern having an excellent shape with high rectangularity can be reliably obtained. On the other hand, when the amount is no more than the upper limit of the above-mentioned range, a uniform solution can be obtained and the storage stability becomes satisfactory.

[Component (C2)]

The component (C2) is a nitrogen-containing organic compound (C2) which does not fall under the definition of the component (C1).

The component (C2) is not particularly limited, as long as it functions as an acid diffusion control agent, and also does not fall under the definition of the component (C1). As the component (C2), any of the conventionally known compounds may be selected for use. Among these, an aliphatic amine, and particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (that is, alkylamines or alkyl alcohol amines), and cyclic amines.

Specific examples of the alkylamines or alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferred.

Further, as the component (C2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (C2), one type of compound may be used alone, or two or more types of compounds may be used in combination.

The component (C2) is typically used in an amount within a range from 0.01 to 5.0 parts by weight, relative to 100 parts by weight of the component (A). When the amount of the component (C2) is within the above-mentioned range, the shape of the resist pattern and the post exposure stability of the latent image formed by the pattern-wise exposure of the resist layer are improved.

<Component (B)>

In the present invention, the component (B) is not particularly limited as long as it does not fall under the definition of the component (C1), and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

Preferred examples of the component (B) include onium salt-based acid generators represented by general formula (b-1) or (b-2) shown below.

[Chemical Formula 70]

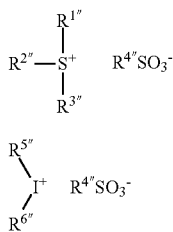

(b-1)

(b-2)

In the formulas, $R^{1''}$ to $R^{3''}$ and $R^{5''}$ to $R^{6''}$ are the same as defined above; and $R^{4''}$ represents a halogenated alkyl group, an aryl group or an alkenyl group which may have a substituent.

In formula (b-1), $R^{1''}$ to $R^{3''}$ are the same as defined above for $R^{1''}$ to $R^{3''}$ in formula (b1-c1).

In formula (b-2), $R^{5''}$ and $R^{6''}$ are the same as defined above for $R^{5''}$ and $R^{6''}$ in formula (b1-c2).

In formulas (b-1) and (b-2), $R^{4''}$ represents a halogenated alkyl group which may have a substituent, an aryl group which may have a substituent or an alkenyl group which may have a substituent.

As an example of the halogenated alkyl group for $R^{4''}$, a group in which part of or all of the hydrogen atoms of the linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

When the alkyl group within the halogenated alkyl group is a linear or branched alkyl group, it preferably has 1 to 10 carbon atoms, more preferably 1 to 8 carbon atoms, and most preferably 1 to 4 carbon atoms. On the other hand, when the alkyl group within the halogenated alkyl group is a cyclic alkyl group, it preferably has 4 to 15 carbon atoms, more preferably 4 to 10 carbon atoms, and most preferably 6 to 10 carbon atoms.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratios are preferable, as they result in increased acid strength.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula: $X-Q^2-$ [in the formula, $Q^2$ represents a divalent linking group containing an oxygen atom; and X represents a hydrocarbon group of 3 to 30 carbon atoms which may have a substituent].

Examples of halogen atoms and alkyl groups as substituents for $R^{4''}$ include the same halogen atoms and alkyl groups as those described above with respect to the halogenated alkyl group for $R^{4''}$.

Examples of the hetero atoms include an oxygen atom, a nitrogen atom, and a sulfur atom.

In the group represented by formula $X-Q^2-$, $Q^2$ represents a divalent linking group containing an oxygen atom.

$Q^2$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amide bond (—C(=O)—NH—), a carbonyl group (—C(=O)—) and a carbonate bond (—O—C(=O)—O—); and combinations of the aforementioned non-hydrocarbon, oxygen atom-containing linking groups with an alkylene group.

Specific examples of the combinations of the aforementioned non-hydrocarbon, oxygen atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5 carbon atoms, and most preferably 1 to 3 carbon atoms.

Specific examples of alkylene groups include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

$Q^2$ is preferably a divalent linking group containing an ester bond or ether bond, and more preferably a group of —$R^{91}$—O—, —$R^{92}$—O—C(=O)— or —C(=O)—O—$R^{93}$—O—C(=O)—.

In the group represented by the formula $X-Q^2-$, the hydrocarbon group for X may be either an aromatic hydrocarbon group or an aliphatic hydrocarbon group.

An aromatic hydrocarbon group is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2 carbon atoms, and most preferably 1 carbon atom.

The aromatic hydrocarbon group may have a substituent. For example, some of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, a n-propoxy group, an iso-propoxy group, a n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for X, there is no particular limitation as long as it is an atom other than carbon and hydrogen. Examples of hetero atoms include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$—, and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 3 to 20 carbon atoms, more preferably 3 to 15 carbon atoms, and most preferably 3 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 3 to 10 carbon atoms, more preferably 3 to 5 carbon atoms, still more preferably 3 to 4 carbon atoms, and most preferably 3 carbon atoms. Examples of linear, monovalent unsaturated hydrocarbon group include a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples of the aliphatic cyclic group include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 71]

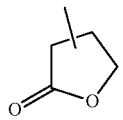
(L1)

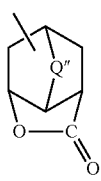
(L2)

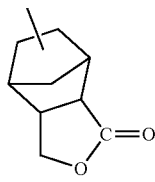
(L3)

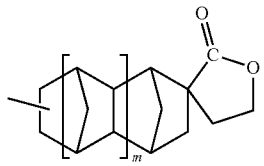
(L4)

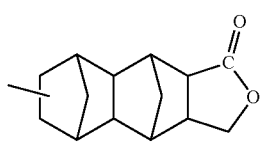
(L5)

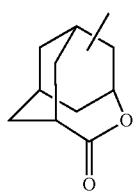
(L6)

-continued

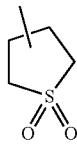
(S1)

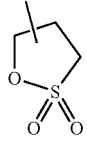
(S2)

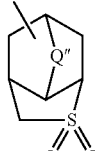
(S3)

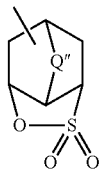
(S4)

In the formulas, Q" represents an alkylene group of 1 to 5 carbon atoms, —O—, —S—, —O—R$^{94}$— or —S—R$^{95}$— (wherein each of R$^{94}$ and R$^{95}$ independently represents an alkylene group of 1 to 5 carbon atoms); and m represents an integer of 0 or 1.

As the alkylene group for Q", R$^{94}$ and R$^{95}$, the same alkylene groups as those described above for R$^{91}$ to R$^{93}$ can be used.

In these aliphatic cyclic groups, part of the hydrogen atoms bonded to the carbon atoms constituting the ring structure may be substituted with a substituent. Examples of the substituent include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

Among the examples described above, as X, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L6), (S3) and (S4) are preferable.

Further, in the present invention, it is particularly desirable that X have a polar moiety, because it results in improved lithographic properties and resist pattern shape.

Specific examples of X having a polar moiety include those in which a part of the carbon atoms constituting the aliphatic hydrocarbon group for X is substituted with a substituent group containing a hetero atom such as —O—, —C(=O)—O—, —C(=O)—, —O—C(=O)—O—, —C(=O)—NH—, —NH— (wherein H may be substituted with a substituent such as an alkyl group or an acyl group), —S—, —S(=O)$_2$— and —S(=O)$_2$—O—.

In the present invention, $R^{4''}$ preferably has X-$Q^2$- as a substituent. In this case, $R^{4''}$ is preferably a group represented by formula X-$Q^2$-$Y^3$— [in the formula, $Q^2$ and X are the same as defined above; and $Y^3$ represents an alkylene group of 1 to 4 carbon atoms which may have a substituent, or a fluorinated alkylene group of 1 to 4 carbon atoms which may have a substituent].

In the group represented by the formula X-$Q^2$-$Y^3$—, as the alkylene group for $Y^3$, the same alkylene group as those described above for $Q^2$ in which the number of carbon atoms is 1 to 4 can be used.

As the fluorinated alkylene group for $Y^3$, the aforementioned alkylene group in which part or all of the hydrogen atoms has been substituted with fluorine atoms can be used.

Specific examples of $Y^3$ include —CF$_2$—, —CF$_2$CF$_2$—, —CF$_2$CF$_2$CF$_2$—, —CF(CF$_3$)CF$_2$—, —CF(CF$_2$CF$_3$)—, —C(CF$_3$)$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CF(CF$_2$CF$_2$CF$_3$)—, —C(CF$_3$)(CF$_2$CF$_3$)—; –CHF—, —CH$_2$CF$_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, —C(CF$_3$)$_2$CH$_2$—; —CH$_2$—, —CH$_2$CH$_2$—, —CH$_2$CH$_2$CH$_2$—, —CH(CH$_3$)CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)—, and —C(CH$_3$)(CH$_2$CH$_3$)—.

$Y^3$ is preferably a fluorinated alkylene group, and particularly preferably a fluorinated alkylene group in which the carbon atom bonded to the adjacent sulfur atom is fluorinated. Examples of such fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—; —CH$_2$CF$_2$—, —CH$_2$CH$_2$CF$_2$—, —CH$_2$CF$_2$CF$_2$—; —CH$_2$CH$_2$CH$_2$CF$_2$—, —CH$_2$CH$_2$CF$_2$CF$_2$—, and —CH$_2$CF$_2$CF$_2$CF$_2$—.

Of these, —CF$_2$—, —CF$_2$CF$_2$—, —CF$_2$CF$_2$CF$_2$— or CH$_2$CF$_2$CF$_2$— is preferable, —CF$_2$—, —CF$_2$CF$_2$— or —CF$_2$CF$_2$CF$_2$— is more preferable, and —CF$_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl) phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

By using any of these onium salt-based acid generators in combination with the component (B1), in the formation of a resist pattern, the critical resolution, sensitivity, exposure latitude (EL margin), mask error factor (MEF), line width roughness (LWR), line edge roughness (LER), circularity, critical dimension uniformity (CDU) or pattern shape can be improved.

Further, as the component (B2), among those represented by the aforementioned general formula (b-1) or (b-2), an onium salt-based acid generator having an anion moiety represented by any one of formulas (b1) to (b8) shown below is particularly desirable.

By using such an onium salt-based acid generator in combination with the component (B1), in the formation of a resist pattern, critical resolution, sensitivity, EL margin, MEF, LWR, LER, circularity, CDU or pattern shape can be particularly improved.

[Chemical Formula 72]

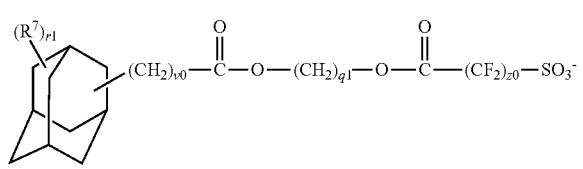
(b1)

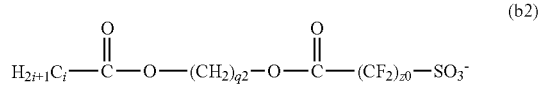
(b2)

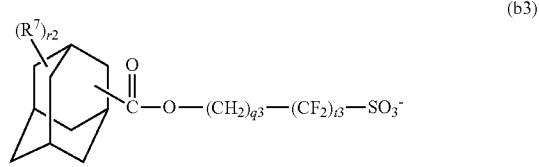
(b3)

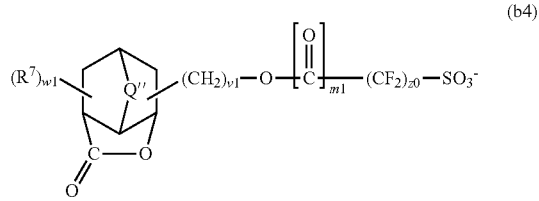
(b4)

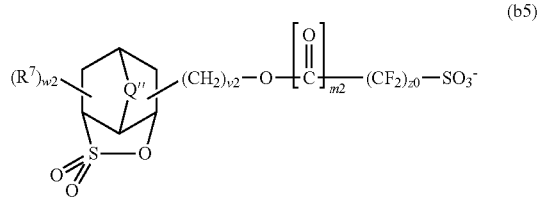
(b5)

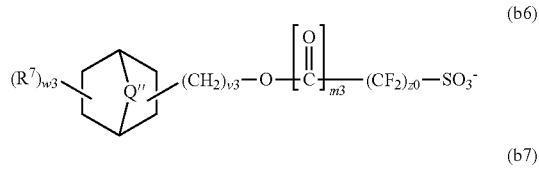
(b6)

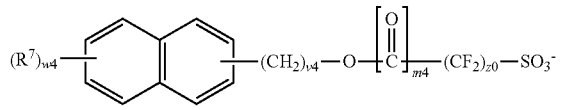
(b7)

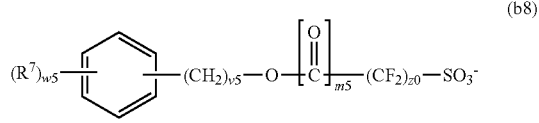
(b8)

In the formulas, z0 represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; i represents an integer of 1 to 20; $R^7$ represents a substituent; each of m1 to m5 independently represents 0 or 1; each of v0 to v5 independently represents an integer of 0 to 3; each of w1 to w5 independently represents an integer of 0 to 3; and Q″ is the same as defined above.

As the substituent for $R^7$, the same groups as those which the aforementioned aliphatic hydrocarbon group or aromatic hydrocarbon group for X may have as a substituent can be used.

If there are two or more of the $R^7$ group, as indicated by the values r1, r2, and w1 to w5, then the two or more of the $R^7$ groups may be the same or different from each other.

Further, as the component (B2), an onium salt-based acid generator in which the anion moiety in general formula (b-1) or (b-2) is replaced by an anion represented by general formula (b-3) or (b-4) shown below can also be preferably used. By using such an onium salt-based acid generator in combination with the component (B1), in the formation of a resist pattern, critical resolution, sensitivity, EL margin, MEF, LWR, LER, circularity, CDU or pattern shape can be further improved.

[Chemical Formula 73]

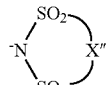
(b-3)

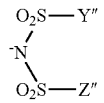
(b-4)

In the formulas, X″ represents an alkylene group of 2 to 6 carbon atoms in which at least one hydrogen atom has been substituted with a fluorine atom; and each of Y″ and Z″ independently represents an alkyl group of 1 to 10 carbon atoms in which at least one hydrogen atom has been substituted with a fluorine atom.

X″ represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y″ and Z″ independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X″ or those of the alkyl group for Y″ and Z″ within the above-mentioned range of the number of carbon atoms, the more the solubility in a resist solvent is improved.

Further, in the alkylene group for X″ or the alkyl group for Y″ and Z″, it is preferable that the number of hydrogen atoms substituted with fluorine atoms is as large as possible because the acid strength increases and the transparency to high energy radiation of 200 nm or less or electron beam is improved.

The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

Further, as the component (B2), an onium salt-based acid generator in which the anion moiety in general formula (b-1) or (b-2) is replaced by an anion represented by general formula (b-5) shown below can also be preferably used.

By using such an onium salt-based acid generator in combination with the component (B1), in the formation of a resist pattern, critical resolution, sensitivity, EL margin, MEF, LWR, LER, circularity, CDU or pattern shape can be particularly improved.

[Chemical Formula 74]

$$R^0\text{—}SO_3^- \quad Z^+ \qquad (b\text{-}5)$$

In the formula, $R^0$ represents a hydrocarbon group of 1 to 12 carbon atoms which may have a substituent, with the provision that the carbon atom adjacent to the sulfur atom within the —$SO_3^-$ group has no fluorine atom bonded thereto; and $Z^+$ represents an organic cation.

In formula (b-5), the hydrocarbon group for $R^0$ may or may not have a substituent.

However, the carbon atom adjacent to the sulfur atom within the —$SO_3^-$ group has no fluorine atom bonded thereto. Therefore, upon exposure, the acid generator component represented by formula (b-5) generates a sulfonic acid exhibiting a weaker acid strength than the acid generated from an acid generator in which a fluorine atom is bonded to the carbon atom adjacent to the sulfur atom within —$SO_3^-$. As a result, in the present invention, the shape of a resist pattern formed can be improved. Further, the lithography properties are also improved.

The substituent preferably contains no fluorine atom, and examples thereof include a lower alkyl group of 1 to 5 carbon atoms and an oxygen atom (═O).

The hydrocarbon group of 1 to 12 carbon atoms for $R^0$ may be an aliphatic hydrocarbon group, or may be an aromatic hydrocarbon group. By virtue of using a hydrocarbon group of 1 to 12 carbon atoms, the rectangularity of the resist pattern is improved.

In those cases where the hydrocarbon group for $R^0$ is an aliphatic hydrocarbon group, the aliphatic hydrocarbon group may be either saturated or unsaturated, but in general, the aliphatic hydrocarbon group is preferably saturated.

Further, the aliphatic hydrocarbon group may be either a chain-like (linear or branched) hydrocarbon group, or a cyclic hydrocarbon group.

As the chain-like hydrocarbon group, a linear or branched alkyl group is preferable. The alkyl group preferably has 1 to 10 carbon atoms, more preferably 1 to 8 carbon atoms, and still more preferably 3 to 8 carbon atoms.

Specific examples of linear or branched alkyl groups include a methyl group, an ethyl group, an n-propyl group, an isopropyl group, an n-butyl group, an isobutyl group, a tert-butyl group, a pentyl group, an isopentyl group, a neopentyl group, an n-hexyl group, an n-heptyl group and an n-octyl group. Among these, a methyl group, an n-propyl group, an n-butyl group and an n-octyl group are preferable, and an n-octyl group is particularly desirable.

Specific examples of the component (B2) having a sulfonate ion as the anion moiety in which $R^0$ represents a linear or branched alkyl group include onium salts having a cation represented by general formula (b1-c1), (b1-c2), (I-1), (I-2), (I-5) or (I-6) above as the cation moiety, and also a sulfonate ion represented by general formula (b-5-1) shown below as the anion moiety.

[Chemical Formula 75]

$$C_aH_{2a+1}SO_3^- \qquad (b\text{-}5\text{-}1)$$

In the formula, a represents an integer of 1 to 10.

In general formula (b-5-1), a represents an integer of 1 to 10, and preferably an integer of 1 to 8.

Specific examples of sulfonate ions represented by general formula (b-5-1) include a methanesulfonate ion, an ethanesulfonate ion, an n-propanesulfonate ion, an n-butanesulfonate ion and an n-octanesulfonate ion.

Examples of cyclic hydrocarbon groups as the hydrocarbon group for $R^0$ include an aliphatic cyclic group and a group in which at least one hydrogen atom within a chain-like hydrocarbon group has been substituted with an aliphatic cyclic group (aliphatic cyclic group-containing group).

As the "aliphatic cyclic group", the same aliphatic cyclic groups as those described above in connection with the acid dissociable, dissolution inhibiting group for the component (A) can be used. The aliphatic cyclic group preferably has 3 to 12 carbon atoms, and more preferably 4 to 10 carbon atoms.

The aliphatic cyclic group may be either a polycyclic group or a monocyclic group.

As the monocyclic group, a group in which one hydrogen atom has been removed from a monocycloalkane of 3 to 6 carbon atoms is preferable, and specific examples thereof include a cyclopentyl group and a cyclohexyl group.

The polycyclic group preferably has 7 to 12 carbon atoms, and specific examples thereof include an adamantyl group, a norbornyl group, an isobornyl group, a tricyclodecanyl group and a tetracyclododecanyl group.

Among the aforementioned examples, a polycyclic group is preferable, and an adamantyl group, a norbornyl group or a tetracyclododecanyl group is preferable from an industrial viewpoint. As described above, these aliphatic cyclic groups may or may not have a substituent.

As the aliphatic cyclic group within the "aliphatic cyclic group-containing group", the same groups as those described above can be used. As the chain-like hydrocarbon group to which the aliphatic cyclic group is bonded to form the "aliphatic cyclic group-containing group", a linear or branched alkyl group is preferable, and a lower alkyl group of 1 to 5 carbon atoms is more preferable. Specific examples thereof include a methyl group, an ethyl group, an n-propyl group, an isopropyl group, an n-butyl group, an isobutyl group, a tert-butyl group, a pentyl group, an isopentyl group and a neopentyl group. Among these, a linear alkyl group is preferable, and from industrial viewpoint, a methyl group or an ethyl group is more preferable.

Specific examples of sulfonate ion in which $R^0$ is a cyclic hydrocarbon group include sulfonate ions represented by formulas (b-5-21) to (b-5-26) shown below.

[Chemical Formula 76]

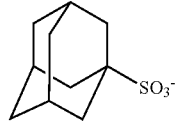

(b-5-21)

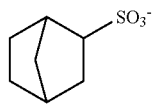

(b-5-22)

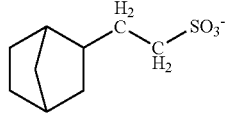

(b-5-23)

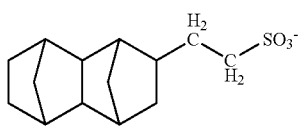
(b-5-24)

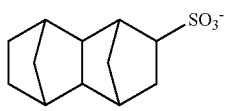
(b-5-25)

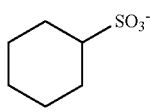
(b-5-26)

Further, as a sulfonate ion in which $R^0$ represents a cyclic hydrocarbon group, an ion represented by general formula (b-5-3) shown below is also preferable.

[Chemical Formula 77]

(b-5-3)

In the formula, $R^{OX}$ represents a cyclic alkyl group of 4 to 12 carbon atoms that has an oxygen atom (=O) as a substituent; and r represents 0 or 1.

In general formula (b-5-3), $R^{OX}$ represents a cyclic alkyl group of 4 to 12 carbon atoms that has an oxygen atom (=O) as a substituent.

The expression "has an oxygen atom (=O) as a substituent" means that two hydrogen atoms bonded to a carbon atom constituting the cyclic alkyl group of 4 to 12 carbon atoms are substituted with an oxygen atom (=O).

The cyclic alkyl group represented by $R^{OX}$ is not particularly limited as long as it has 4 to 12 carbon atoms, and may be either a polycyclic group or a monocyclic group. Examples thereof include a group in which one hydrogen atom has been removed from a monocycloalkane or a polycycloalkane such as a bicycloalkane, tricycloalkane or tetracycloalkane. As the monocyclic group, a group in which one hydrogen atom has been removed from a monocycloalkane of 3 to 8 carbon atoms is preferable, and specific examples thereof include a cyclopentyl group, a cyclohexyl group, a cycloheptyl group and a cyclooctyl group. The polycyclic group preferably has 7 to 12 carbon atoms, and specific examples thereof include an adamantyl group, a norbornyl group, an isobornyl group, a tricyclodecanyl group and a tetracyclododecanyl group.

As $R^{OX}$, a polycyclic alkyl group of 4 to 12 carbon atoms that has an oxygen atom (=O) as a substituent is preferable. From an industrial viewpoint, a group in which two hydrogen atoms bonded to a carbon atom constituting an adamantyl group, a norbornyl group or a tetracyclododecanyl group are substituted with an oxygen atom (=O) is preferable, and a norbornyl group having an oxygen atom (=O) as a substituent is particularly desirable.

$R^{OX}$ may have a substituent other than an oxygen atom. As an example of such a substituent, a lower alkyl group of 1 to 5 carbon atoms can be given.

In general formula (b-5-3), r represents 0 or 1, and preferably 1.

Specific examples of preferable anions represented by formula (b-5-3) include anions represented by formulas (b-5-31) and (b-5-32) shown below.

Of these, in terms of the excellent effects of using in combination with the component (B1), a camphorsulfonate ion represented by formula (b-5-31) shown below is preferable.

[Chemical Formula 78]

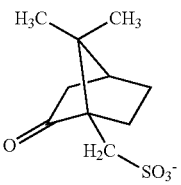
(b-5-31)

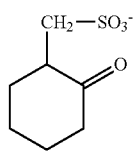
(b-5-32)

In formula (b-5), examples of aromatic hydrocarbon groups as the hydrocarbon group for $R^0$ include a phenyl group, a tolyl group, a xylyl group, a mesityl group, a phenethyl group and a naphthyl group. As described above, the aromatic hydrocarbon group may or may not have a substituent.

Specific examples of aromatic hydrocarbon groups for $R^0$ include groups represented by general formula (b-5-41) or (b-5-42) shown below.

[Chemical Formula 79]

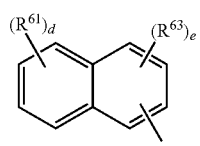
(b-5-41)

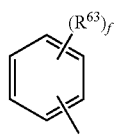
(b-5-42)

In formula (b-5-41), each of $R^{61}$ and $R^{62}$ independently represents an alkyl group of 1 to 5 carbon atoms, an alkoxy group of 1 to 5 carbon atoms or an halogen atom.

Examples of the alkyl group for $R^{61}$ and $R^{62}$ include a methyl group, an ethyl group, a propyl group, an isopropyl group, an n-butyl group, an isobutyl group, a tert-butyl group, a pentyl group, an isopentyl group and a neopentyl group. Among these, a methyl group is particularly desirable.

Examples of the alkoxy group for $R^{61}$ and $R^{62}$ include a methoxy group, an ethoxy group, an n-propoxy group, an isopropoxy group, an n-butoxy group and a tert-butoxy group. Among these, a methoxy group or an ethoxy group is particularly desirable.

Each of d and e independently represents an integer of 0 to 4, preferably 0 to 2, and most preferably 0.

If there are two or more of the $R^{61}$ group and/or $R^{62}$ group, as indicated by the value d and/or e, then the two or more of the $R^{61}$ groups and/or the $R^{62}$ groups may be the same or different from each other.

In formula ((b-5-42), $R^{63}$ represents an alkyl group of 1 to 5 carbon atoms, an alkoxy group of 1 to 5 carbon atoms or an halogen atom.

Examples of the alkyl group for $R^{63}$ include a methyl group, an ethyl group, a propyl group, an isopropyl group, an n-butyl group, an isobutyl group, a tert-butyl group, a pentyl group, an isopentyl group and a neopentyl group. Among these, a methyl group is particularly desirable.

Examples of the alkoxy group for $R^{63}$ include a methoxy group, an ethoxy group, an n-propoxy group, an isopropoxy group, an n-butoxy group and a tert-butoxy group. Among these, a methoxy group or an ethoxy group is particularly desirable.

f represents an integer of 0 to 3, preferably 1 or 2, and most preferably 1.

If there are two or more of the $R^{63}$ group, as indicated by the value f, then the two or more of the $R^{63}$ groups may be the same or different from each other.

Examples of sulfonates having an aromatic hydrocarbon group represented by formula (b-5-42) include benzenesulfonate, perfluorobenzenesulfonate and p-toluenesulfonate.

Further, an onium salt-based acid generator in which the anion moiety ($R^{4''}SO_3^-$) in general formula (b-1) or (b-2) has been replaced with $R^a$—COO$^-$ [in the formula, $R^a$ represents an alkyl group or a fluorinated alkyl group] (and the cation moiety is the same as cation moiety within formula (b-1) or (b-2)) may also be used as the onium salt-based acid generator for the component (B2).

In the formula above, as $R^a$, the same groups as those described above for $R^{4''}$ can be used.

Specific examples of the group represented by the formula "$R^a$—COO$^-$" include a trifluoroacetic acid ion, an acetic acid ion, and a 1-adamantanecarboxylic acid ion.

Further, onium salt-based acid generators having a cation moiety represented by general formula (I-1), (I-2), (I-5) or (I-6) above, and having a fluorinated alkylsulfonate ion (e.g., the anion moiety ($R^{4''}SO_3^-$) in general formula (b-1) or (b-2) above) or an anion moiety represented by general formulas (b1) to (b8), (b-3), (b-4) or (b-5) above as the anion moiety, can also be used.

In the present description, an oximesulfonate acid generator is a compound having at least one group represented by general formula (B-1) shown below, and has a feature of generating acid by irradiation (exposure). Such an oximesulfonate acid generator can also be preferably used as the component (B2). By using such an oximesulfonate acid generator in combination with the component (B1), in the formation of a resist pattern, critical resolution, sensitivity, EL margin, MEF, LWR, LER, circularity, CDU or pattern shape can be further improved.

[Chemical Formula 80]

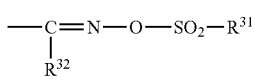

(B-1)

In formula (B-1), each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 81]

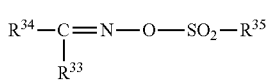

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 82]

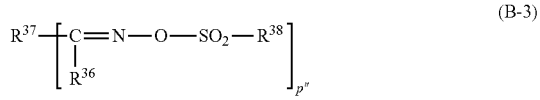

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 85) may be preferably used.

Furthermore, as preferable examples, the following can be used.

[Chemical Formula 83]

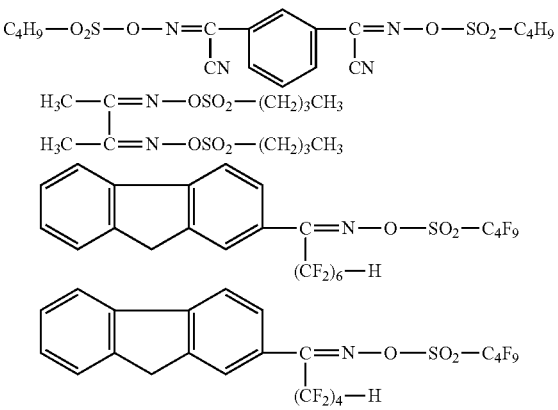

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), one type of acid generator may be used alone, or two or more types may be used in combination.

In the resist composition of the present invention, the total amount of the component (B) relative to 100 parts by weight of the component (A) is preferably 0.5 to 50 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>
[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or as a mixed solvent containing two or more different solvents.

Among these, propylene glycol monomethyl ether acetate (PGMEA), propylene glycol monomethyl ether (PGME), ethyl lactate (EL) and γ-butyrolactone are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of a mixture of PGMEA and PGME with γ-butyrolactone is also preferable. In this case, the mixing ratio (former:latter) of such a mixed solvent is preferably from 99.9:0.1 to 80:20, more preferably 99.9:0.1 to 90:10, and most preferably 99.9:0.1 to 95:5. By virtue of the above-mentioned range, the rectangularity of the resist pattern is improved.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is preferably within a range from 0.5 to 20% by weight, and more preferably from 1 to 15% by weight.

Dissolving of the components for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

As described above, according to the resist composition of the present invention, excellent lithography properties such as roughness, mask reproducibility and exposure latitude can be achieved, and a resist pattern having an excellent shape with high rectangularity can be formed. The reasons why these effects can be achieved have not been elucidated yet, but are presumed as follows.

The resist composition of the present invention includes a nitrogen-containing organic compound component (C) containing a compound (C1) represented by general formula (c1).

The anion moiety of the compound (C1) has a structure in which the skeleton "$X^O$—$SO_3^-$" has an $R^N$—C(=O)—O— group bonded thereto. As a result, the anion moiety of the compound (C1) exhibits a high polarity and has a three-dimensionally bulky structure, as compared to a fluorinated alkylsulfonic ion which has been conventionally used as an anion moiety. By virtue of the intermolecular force due to the high polarity, and also the three-dimensionally bulky structure, it is presumed that diffusion of acid within the resist film is chemically and physically suppressed, as compared to the anion moiety of a conventional acid generator such as nonafluorobutanesulfonate. Therefore, diffusion of the acid generated in the exposed regions to the unexposed regions can be suppressed.

Following photodegradation, the compound (C1) undergoes a neutralization reaction with acid, thereby losing the function as a quencher.

As a result, it is presumed that the contrast between the exposed portions and the unexposed portions can be increased, thereby improving the pattern shape and lithography properties. Further, since the anion moiety has a short-chain skeleton, as compared to the compound used in the acid generator disclosed in Patent Document 2, the molecular motion of the compound (C1) is suppressed, thereby efficiently suppressing the diffusion of acid.

Moreover, the divalent aliphatic hydrocarbon group for $X^O$ exhibits an excellent decomposability, as compared to, for example, a perfluoroalkyl chain of 6 to 10 carbon atoms. Therefore, the effects of improving handling properties in terms of bioaccumulation can also be achieved.

Furthermore, because the $R^N$ group is bound while being included in the compound (C1), compatibility with the acid generator is improved, and the distribution of the $R^N$ group within the resist film becomes more uniform, thereby suppressing the bias in distributions of the $R^N$ group and the acid generator.

For the reasons described above, by using the resist composition of the present invention, it is presumed that a line and space pattern (L/S pattern) having excellent properties in terms of the line width roughness (LWR), exposure margin (EL margin), mask error factor (MEF), resist pattern shape, and the like, can be formed.

<<Method of Forming a Resist Pattern>>

Next, a method of forming a resist pattern according to a second aspect of the present invention will be described.

The method of forming a resist pattern according to the present invention includes: applying a resist composition of the first aspect according to the present invention to a substrate to form a resist film on the substrate; conducting exposure of the resist film; and developing the resist film to form a resist pattern.

More specifically, the method of forming a resist pattern according to the present invention can be performed, for example, as follows.

Firstly, a resist composition of the present invention is applied onto a substrate using a spinner or the like, and a bake treatment (post applied bake (PAB)) is conducted at a temperature of 80 to 150° C. for 40 to 120 seconds, preferably 60 to 90 seconds, to form a resist film.

Following selective exposure of the thus formed resist film, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, a baking treatment (post exposure baking (PEB)) is conducted under temperature conditions of 80 to 150° C. for 40 to 120 seconds, and preferably 60 to 90 seconds.

Subsequently, the resist film is subjected to a developing treatment.

The developing treatment is conducted using an alkali developing solution in the case of alkali developing process, and a developing solution containing an organic solvent (organic developing solution) in the case of solvent developing process.

After the developing treatment, a rinsing treatment is preferably conducted. With respect to the rinsing treatment, a water rinse using pure water is preferred in the case of alkali developing process, and a rinsing liquid containing an organic solvent is preferably used in the case of solvent developing process.

In the case of solvent developing process, a treatment to remove the developing solution or rinsing liquid remaining on the pattern using a supercritical fluid may be conducted following the developing treatment or rinsing treatment.

After the developing treatment or rinsing treatment, drying is carried out. If desired, a bake treatment (post bake) may be conducted following the developing treatment. In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is highly useful for KrF excimer laser, ArF excimer laser, EB and EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

Examples of the alkali developing solutions to be used in the alkali developing process include a 0.1 to 10% by weight aqueous solution of tetramethylammonium hydroxide (TMAH).

The organic solvent included in the organic developing solution used for the developing treatment in the solvent developing process may be any organic solvent which can dissolve the component (A) (namely, the component (A) prior to exposure), and can be selected appropriately from amongst the known organic solvents. More specifically, polar solvents such as ketone-based solvents, ester-based solvents, alcohol-based solvents, amide-based solvents and ether-based solvents; and hydrocarbon-based solvents can be used.

If required, known additives can be added to the developing solution. Examples of the additives include surfactants. The surfactant is not particularly limited, and for example, an ionic or non-ionic fluorine and/or silicon surfactant can be used.

When a surfactant is added, the amount thereof based on the total amount of the developing solution is generally 0.001 to 5% by weight, preferably 0.005 to 2% by weight, and more preferably 0.01 to 0.5% by weight.

The developing treatment can be conducted using a known developing method. Examples of these methods include a method in which the substrate is immersed in the developing solution for a certain period of time (dipping method), a method in which the developing solution is accumulated by surface tension to remain still at the surface of the substrate for a certain period of time (puddle method), a method in which the developing solution is sprayed onto the surface of the substrate (spraying method), and a method in which the substrate rotating at a constant speed is scanned with a developing-solution ejecting nozzle at a constant speed while continuously ejecting the developing solution (dynamic dispensing method).

As an organic solvent included in the rinsing liquid which is used for the rinsing treatment following the developing treatment in the solvent developing process, for example, an organic solvent which hardly dissolves the resist pattern can be appropriately selected for use from amongst the organic solvents listed above as the organic solvents included in the developing solution. In general, at least one type of solvent selected from amongst hydrocarbon-based solvents, ketone-based solvents, ester-based solvents, alcohol-based solvents, amide-based solvents and ether-based solvents is used. Of these, it is preferable to use at least one type of solvent selected from amongst hydrocarbon-based solvents, ketone-based solvents, ester-based solvents, alcohol-based solvents and amide-based solvents; it is more preferable to use at least one type of solvent selected from amongst alcohol-based solvents and ester-based solvents; and alcohol solvents are particularly desirable.

The rinsing treatment (washing treatment) using a rinsing liquid can be conducted using a known rinsing method. Examples of these methods include a method in which the rinsing liquid is continuously applied onto the substrate rotating at a constant speed (rotational coating method), a method in which the substrate is immersed in the rinsing liquid for a certain period of time (dipping method), and a method in which the rinsing liquid is sprayed onto the surface of the substrate (spraying method).

<<Compound>>

A compound according to a third aspect of the present invention is a compound represented by general formula (c1') shown below, and is the same compound as the aforementioned component (C1) included in the component (C) of the resist composition according to the first aspect of the present invention.

[Chemical Formula 84]

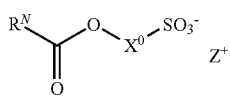

(c1')

In the formula, $R^N$ represents a nitrogen-containing heterocyclic group which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $Z^+$ represents an organic cation or a metal cation.

The same explanations as those provided for the above component (C1) can be applied to the compound of the present invention. However, in the compound according to the present invention, the cation moiety $Z^+$ may be a metal cation.

—Metal Cation

The metal cation for $Z^+$ is not particularly limited, although an alkali metal ion is preferable. Specific examples thereof include a sodium ion, a lithium ion and a potassium ion, and a sodium ion or a lithium ion is more preferable.

(Production Method of Compound)

Hereafter, a compound represented by a chemical formula (I) is designated as "compound (I)", and the same applies for compounds represented by other formulas.

The compound (c1') of the present invention can be produced by reacting a compound (c1'-0) shown below with a compound (1') shown below.

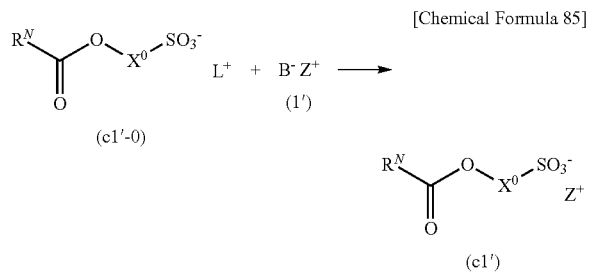

In the formula, $Z^+$ is the same as defined above for $Z^+$ in formula (c1'); $L^+$ represents an alkali metal ion or an ammonium ion which may have a substituent; and $B^-$ represents an anion.

In formula (c1'-0), $L^+$ represents an alkali metal ion or an ammonium ion which may have a substituent.

Examples of the alkali metal ion include a sodium ion, a lithium ion and a potassium ion.

Examples of the ammonium ion which may have a substituent include those represented by general formula (b1-c0) shown below.

[Chemical Formula 86]

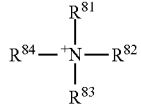

(b1-c0)

In the formula, each of $R^{81}$ to $R^{84}$ independently represents a hydrogen atom or a hydrocarbon group which may have a substituent, provided that at least one of $R^{81}$ to $R^{84}$ represents the hydrocarbon group, and at least two of $R^{81}$ to $R^{84}$ may be mutually bonded to form a ring.

In formula (b1-c0), each of $R^{81}$ to $R^{84}$ independently represents a hydrogen atom or a hydrocarbon group which may have a substituent, and at least one of $R^{81}$ to $R^{84}$ represents the hydrocarbon group.

Examples of the hydrocarbon groups for $R^{81}$ to $R^{84}$ include the same hydrocarbon groups as those described above for X.

The hydrocarbon group may be either an aliphatic hydrocarbon group or an aromatic hydrocarbon group. When the hydrocarbon group is an aliphatic hydrocarbon group, it is particularly desirable that the aliphatic hydrocarbon group is an alkyl group of 1 to 12 carbon atoms which may have a substituent.

At least one of $R^{81}$ to $R^{84}$ represents the hydrocarbon group, and it is preferable that two or three of $R^{81}$ to $R^{84}$ represent the hydrocarbon group.

At least two of $R^{81}$ to $R^{84}$ may be mutually bonded to form a ring. For example, two of $R^{81}$ to $R^{84}$ may be bonded together to form a single ring, three of $R^{81}$ to $R^{84}$ may be bonded together to form a single ring, or two different sets of $R^{81}$ to $R^{84}$ may be bonded together separately to form two rings.

The ring which is formed by at least two of $R^{81}$ to $R^{84}$ bonded together with the nitrogen atom in the formula (namely, a heterocycle including the nitrogen atom as a hetero atom) may be either an aliphatic heterocycle, or an aromatic heterocycle. Further, the heterocycle may be either monocyclic or polycyclic.

Specific examples of the ammonium ion represented by general formula (b1-c0) include ammonium ions derived from an amine.

Here, the expression "ammonium ions derived from an amine" includes cations in which a hydrogen atom is bonded to the nitrogen atom of an amine, and quaternary ammonium ions in which an additional substituent is bonded to the nitrogen atom of an amine.

The amine that gives rise to the above ammonium ion may be either an aliphatic amine or an aromatic amine.

As the aliphatic amine, an amine in which at least one hydrogen atom of ammonia ($NH_3$) has been substituted with an alkyl group or hydroxyalkyl group of not more than 12 carbon atoms (namely, an alkylamine or alkyl alcohol amine), or a cyclic amine is particularly desirable.

Specific examples of the alkylamines or alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably contains 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of the aromatic amine include aniline, pyridine, 4-dimethylaminopyridine (DMAP), pyrrole, indole, pyrazole, and imidazole.

Examples of the quaternary ammonium ion include a tetramethylammonium ion, a tetraethylammonium ion and a tetrabutylammonium ion.

As the ammonium ion represented by general formula (b1-c0), an ion in which at least one of $R^{81}$ to $R^{84}$ represents an alkyl group and also at least one represents a hydrogen atom is particularly desirable.

Of these, ions in which three of $R^{81}$ to $R^{84}$ represent alkyl groups while the remaining one group represents a hydrogen atom (namely, trialkylammonium ions), or ions in which two of $R^{81}$ to $R^{84}$ represent alkyl groups while one of the remaining groups represents a hydrogen atom (namely, dialkylammonium ions) are preferred.

It is preferable that each of the alkyl groups within the trialkylammonium ions or the dialkylammonium ions independently has 1 to 10 carbon atoms, more preferably 1 to 8 carbon atoms, and most preferably 1 to 5 carbon atoms. Specific examples include a methyl group, an ethyl group, a propyl group, a butyl group, a pentyl group, a hexyl group, a heptyl group, an octyl group, a nonyl group and a decanyl group. Of these, an ethyl group is the most desirable.

In formula (1'), $B^-$ represents an anion.

Examples of anions in formula (1') include halogen ions, alkyl sulfate, alkyl sulfonate and aryl sulfonate.

—Reaction Between Compound (c1'-0) and Compound (1')

The compound (c1'-0) can be reacted with the compound (1'), for example, by dissolving these compounds in a solvent such as water, dichloromethane, acetonitrile, methanol, chloroform or methylene chloride, and then stirring the resulting solution to effect a reaction.

The reaction temperature is preferably 0 to 150° C., and more preferably 0 to 100° C. The reaction time varies depending on the reactivity of the compound (c1'-0) and the compound (1'), and the reaction temperature and the like, but in general, the reaction time is preferably 0.5 to 48 hours, and more preferably 1 to 24 hours.

Generally, the amount of the compound (1') used in the reaction is preferably 0.5 to 2 moles per 1 mole of the compound (c1'-0).

After the reaction, the compound (c1') within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The compound (c1'-0) can be produced, for example, by the following methods (I) to (III).

Method (I): A dehydration condensation reaction between $R^N$—C(=O)—OH and HO—$X^0$—$SO_3^-$.$Na^+$ is effected under the presence of a condensation agent (such as diisopropylcarbodiimide), followed by an appropriate cation exchange using a salt corresponding to $L^+$ in formula (c1'-0).

An example of a synthetic pathway is shown below.

[Chemical Formula 87]

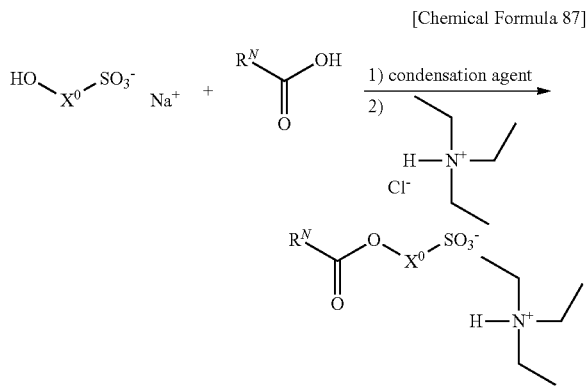

Method (II): A reaction between $R^N$—C(=O)—Cl and HO—$X^0$—$SO_3^-$.$Na^+$ is effected under the presence of a base.

An example of a synthetic pathway is shown below.

[Chemical Formula 88]

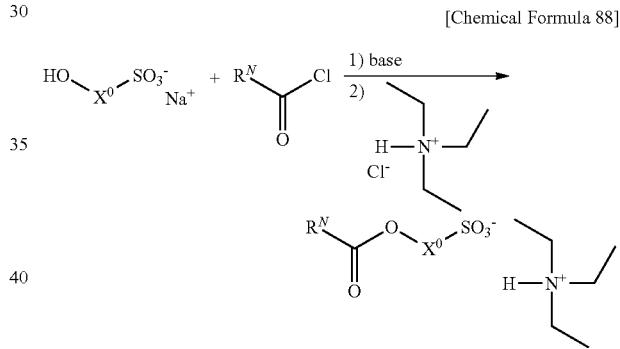

Method (III): A reaction between $R^N$—C(=O)—Cl and HO—$X^0$—Br is effected under the presence of a basic catalyst, and then the terminal group is substituted by the addition of $Na_2S_2O_4$, followed by an oxidation reaction. An example of a synthetic pathway is shown below.

[Chemical Formula 89]

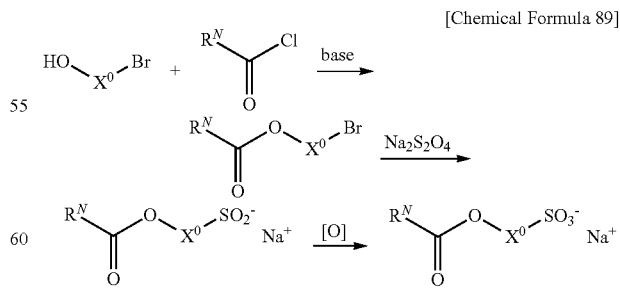

The structures of the compound according to the present invention and the intermediate products that are obtained in the above-described manner can be confirmed by a general organic analysis methods such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The compound of the present invention described above is a novel compound that is useful as a quencher for resist compositions, and can be blended within a resist composition as a quencher.

EXAMPLES

As follows is a more detailed description of the present invention based on a series of examples, although the scope of the present invention is in no way limited by these examples. In the NMR analysis, the internal standard for $^1$H-NMR was tetramethylsilane, and the internal standard for $^{19}$F-NMR was hexafluorobenzene (provided that the peak of hexafluorobenzene was regarded as −160 ppm).

Synthesis Example 1

Synthesis of Anion-1

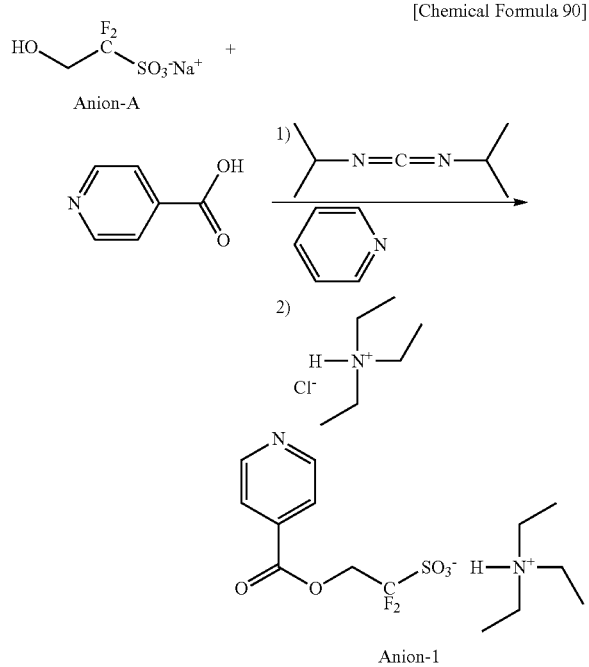

Under a nitrogen atmosphere, 26 g of isonicotinic acid and 130 g of pyridine were added and cooled to 5° C. 35 g of diisopropylcarbodiimide was then added thereto, and the resulting mixture was stirred at 5° C. for 10 minutes. Thereafter, 37 g of Anion-A was gradually added thereto, and a reaction was effected at 5° C. for 20 hours. Then, 580 g of pure water was added to the resulting solution. After stirring the resulting mixture for 30 minutes, the precipitated diisopropylurea was removed by filtration. The filtrate was collected, and 33 g of triethylamine hydrochloride was then added thereto, followed by stirring at room temperature for 1 hour. Extraction was conducted three times with 578.4 g of dichloromethane, and the resultant was then washed with pure water. The resulting dichloromethane layer was concentrated and dried, thereby obtaining 37 g of Anion-1.

The obtained Anion-1 was analyzed by NMR.
$^1$H-NMR (DMSO, 400 MHz): δ (ppm)=8.86 (d, 2H, ArH), 7.89 (d, 2H, ArH), 4.89 (t, 2H, CH$_2$CF$_2$), 3.13 (q, 6H, CH$_2$CH$_3$), 1.20 (t, 9H, CH$_2$CH$_3$).
$^{19}$F-NMR (DMSO, 376 MHz): δ (ppm)=−111.0.

From the results shown above, it was confirmed that Anion-1 had a structure shown above.

Example 1

Synthesis of Compound PAG-1

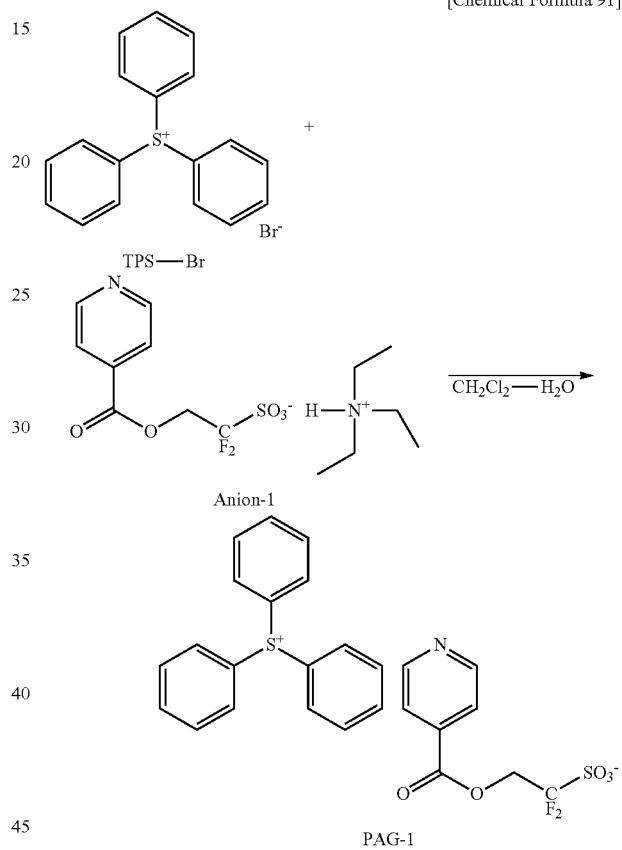

3.53 g of TPS-Br, 3.68 g of Anion-1, 26.5 g of dichloromethane, and 26.5 g pure water were added to a recovery flask, and the resulting mixture was stirred at room temperature for 1 hour. Then, a liquid separation was conducted, and the resulting dichloromethane layer was repeatedly washed with 26.5 g of pure water. The obtained organic layer was then concentrated under reduced pressure, thereby yielding 4.4 g of PAG-1 in the form of a white solid.

The obtained compound PAG-1 was analyzed by NMR.
$^1$H-NMR (DMSO, 400 MHz): δ (ppm)=8.86 (d, 2H, ArH), 7.74-7.90 (m, 17H, ArH), 4.89 (t, 2H, CH$_2$CF$_2$).
$^{19}$F-NMR (DMSO, 376 MHz): δ (ppm)=−111.0. From the results shown above, it was confirmed that the compound PAG-1 had a structure shown above.

Examples 2 to 56

Synthesis of Compounds PAG-2 to PAG-56

The same operations were conducted as in Example 1 described above with the exception that synthesis was carried out by using the respective compounds indicated in Tables 1 to 20 shown below (in an equimolar amount) instead of the compound (M⁺X⁻). As a result, the products (namely, compounds PAG-2 to PAG-56) constituted of anions and cations indicated in Tables 1 to 20 were obtained.

Each of the obtained compounds was analyzed by NMR. The results are also indicated in Tables 1 to 20. The symbols "↑" in Tables 1 to 20 indicate that an anion of the compounds PAG-2 to PAG-56 is the same as the anion of the compound PAG-1.

TABLE 1

| Example | Compound | NMR | Salt M⁺X⁻ | Cation | Anion |
|---|---|---|---|---|---|
| 1 | PAG-1 | ¹H-NMR (DMSO-d6, 400 MHz): δ (ppm) = 8.86 (d, 2H ArH), 7.74-7.90 (m, 17H, ArH), 4.89 (t, 2H, CH2CF2), ¹⁹F-NMR (DMSO-d6, 376 MHz): δ (ppm) = −111.0. | [structure] | [structure] | [structure] |
| 2 | PAG-2 | ¹H-NMR (DMSO-d6, 400 MHz): δ (ppm) = 8.86 (d, 2H ArH), 8.50 (d, 2H, ArH), 8.37 (d, 2H, ArH), 7.93 (t, 2H, ArH), 7.89 (d, 2H, ArH), 7.55-7.75 (m, 7H, ArH), 4.89 (t, 2H, CH2CF2), ¹⁹F-NMR (DMSO-d6, 376 MHz): δ (ppm) = −111.0. | [structure] | [structure] | ↑ |
| 3 | PAG-3 | ¹H-NMR (DMSO-d6, 400 MHz): δ (ppm) = 8.86 (d, 2H ArH), 7.89 (d, 2H, ArH), 7.72-7.84 (m, 12H, ArH), 7.56 (d, 2H, ArH), 4.89 (t, 2H, CH2CF2), 3.35 (s, 3H, CH3), ¹⁹F-NMR (DMSO-d6, 376 MHz): δ (ppm) = −111.0. | [structure] | [structure] | ↑ |
| 4 | PAG-4 | ¹H-NMR (DMSO-d6, 400 MHz): δ (ppm) = 8.86(d, 2H ArH), 7.89 (d, 2H, ArH), 7.75-7.86 (m, 10H, ArH), 7.61 (s, 2H, ArH), 4.89 (t, 2H, CH2CF2), 4.62 (s, 2H, CH2), 2.31 (s, 6H, CH3), 1.49-1.97 (m, 17H, Adamantane) ¹⁹F-NMR (DMSO-d6, 376 MHz): δ (ppm) = −111.0 | [structure] | [structure] | ↑ |
| 5 | PAG-5 | ¹H-NMR (DMSO-d6, 400 MHz): δ (ppm) = 8.86 (d, 2H ArH), 7.89 (d, 2H, ArH), 7.76-7.82 (m, 10H, ArH), 7.59 (s, 2H, ArH), 4.89 (t, 2H, CH2CF2), 4.55 (s, 2H, CH2), 2.29 (m, 6H, CH3), 1.90-1.93 (m, 4H, CH2, cyclopentyl), 1.48-1.75 (m, 6H, cyclopentyl), 0.77-0.81 (t, 3H, CH3), ¹⁹F-NMR (DMSO-d6, 376 MHz): δ (ppm) = −111.0 | [structure] | [structure] | ↑ |

TABLE 3

| Example | Compound | NMR | Salt M+X− | Cation | Anion |
|---|---|---|---|---|---|
| 6 | PAG-6 | ¹H-NMR (DMSO-d6, 400 MHz): δ (ppm) = 8.86 (d, 2H, ArH), 7.89 (d, 2H, ArH), 7.76-7.82 (m, 10H, ArH), 7.59 (s, 2H, ArH), 4.89 (t, 2H, CH2CF2), 4.55 (s, 2H, CH2), 2.29 (m, 6H, CH3), 1.90-2.08 (m, 2H, cyclopentyl), 1.48-1.75 (m, 9H, CH3, cyclopentyl). ¹⁹F-NMR (DMSO-d6, 376 MHz): δ (ppm) = −111.0 | 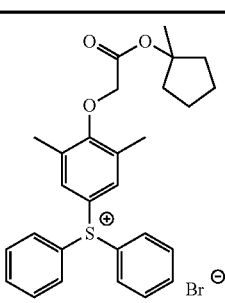 | 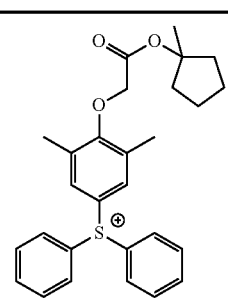 | ↑ |
| 7 | PAG-7 | ¹H-NMR (DMSO-d6, 400 MHz): δ (ppm) = 10.05 (s, 1H, OH), 8.86 (d, 2H, ArH), 7.89 (d, 2H, ArH), 7.64-7.87 (m, 10H, ArH), 7.56 (s, 2H, ArH), 4.89 (t, 2H, CH2CF2), 2.22 (m, 6H, CH3),. ¹⁹F-NMR (DMSO-d6, 376 MHz): δ (ppm) = −111.0 | 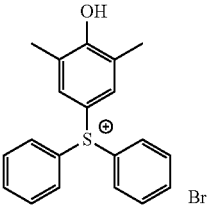 | 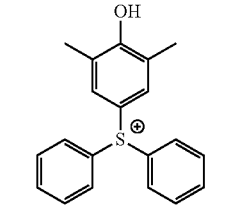 | ↑ |
| 8 | PAG-8 | ¹H-NMR (DMSO-d6, 400 MHz): δ (ppm) = 8.86 (d, 2H, ArH), 7.71-7.89 (m, 12H, ArH), 7.59 (s, 2H, ArH), 4.89 (t, 2H, CH2CF2), 4.53 (s, 2H, CH2), 2.30 (d, 6H, CH3),. ¹⁹F-NMR (DMSO-d6, 376 MHz): δ (ppm) = −111.0 | 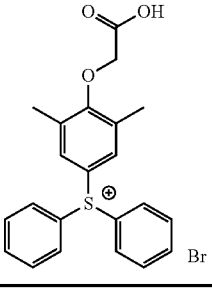 | 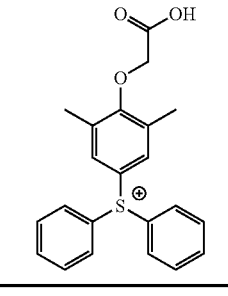 | ↑ |

TABLE 4

| Example | Compound | NMR | Salt M+X− | Cation | Anion |
|---|---|---|---|---|---|
| 9 | PAG-9 | ¹H-NMR (DMSO-d6, 400 MHz): δ (ppm) = 8.86 (d, 2H, ArH), 7.89 (d, 2H, ArH), 7.75-7.86 (m, 10H, ArH), 7.63 (s, 2H, ArH), 4.89 (t, 2H, CH2CF2), 4.55 (s, 2H, CO—CH2), 2.30 (s, 6H, ArCH3), 1.43 (s, 9H, t-Butyl), ¹⁹F-NMR (DMSO-d6, 37 MHz): δ (ppm) = −111.0 | 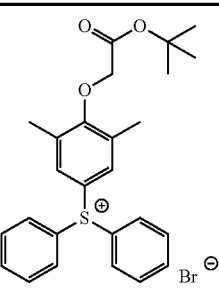 | 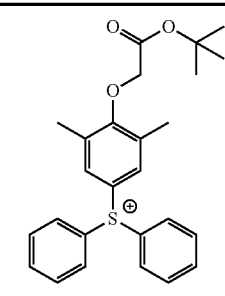 | ↑ |
| 10 | PAG-10 | ¹H-NMR (DMSO-d6, 400 MHz): δ (ppm) = 8.86 (d, 2H, ArH), 7.89 (d, 2H, ArH), 7.75-7.87 (m, 10H, ArH), 7.63 (s, 2H, ArH), 4.94 (t, 2H, OCH2CF2), 4.89 (t, 2H, CH2CF2), 4.84 (s, 2H, OCH2), 2.37 (s, 6H, CH3), ¹⁹F-NMR (DMSO-d6, 37 MHz): δ (ppm) = −80.4, −111.0, −119.7. | 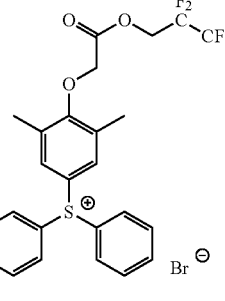 | 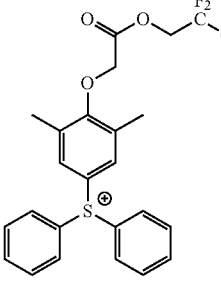 | ↑ |

TABLE 4-continued

| Example | Compound | NMR | Salt M⁺X⁻ | Cation | Anion |
|---|---|---|---|---|---|
| 11 | PAG-11 | ¹H-NMR (DMSO-d6, 400 MHz): δ (ppm) = 8.86 (d, 2H, ArH), 7.89 (d, 2H, ArH), 7.72-7.83 (m, 10H, ArH), 7.59 (s, 2H, ArH), 4.90 (m, 1H, sultone), 4.89 (t, 2H, CH2CF2), 4.62-4.68 (m, 3H, CH2O + sultone), 3.83-3.89 (m, 1H, sultone), 3.43 (m, 1H, sultone), 1.75-2.49 (m, 11H, sultone + ArH – CH3), ¹⁹F-NMR (DMSO-d6, 37 MHz): δ (ppm) = –111.0. | | | ↑ |

TABLE 5

| Example | Compound | NMR | Salt Wk. | Cation | Anion |
|---|---|---|---|---|---|
| 12 | PAG-12 | ¹H-NMR (DMSO-d6, 400 MHz): δ (ppm) = 8.86(d, 2H, ArH), 7.89 (d, 2H, ArH), 7.74-7.84 (m, 10H, ArH), 7.61 (s, 2H, ArH), 5.42 (t, 1H, oxo-norbornane), 4.97 (s, 1H, oxo-norbornane), 4.89 (t, 2H, CH2CF2), 4.67-4.71 (m, 4H, CH2 + oxo-norbornane), 2.69-2.73 (m, 1H, oxo-norbornane), 2.32(s, 6H, Ar—CH3), 2.06-2.16 (m, 2H, oxo-norbornane), ¹⁹F-NMR (DMSO-d6, 376 MHz): δ (ppm) = –111.0. | | | ↑ |
| 13 | PAG-13 | ¹H-NMR (DMSO-d6, 400 MHz): δ (ppm) = 8.86 (d, 2H, ArH), 7.89 (d, 2H, ArH), 7.73-7.85 (m, 10H, ArH), 7.59 (s, 2H, ArH), 4.89 (t, 2H, CH2CF2), 3.83 (t, 2H, OCH2), 2.33 (s, 6H, CH3), 1.45 (m, 4H, CH2), 1.29 (m, 4H, CH2), 0.87 (t, 3H, CH3), ¹⁹F-NMR (DMSO-d6, 376 MHz): δ (ppm) = –111.0. | | | ↑ |
| 14 | PAG-14 | ¹H-NMR (DMSO-d6, 400 MHz): δ (ppm) = 8.86 (d, 2H, ArH), 8.53 (d, 2H, ArH), 8.27 (d, 2H, ArH), 7.95 (t, 2H, ArH), 7.89 (d, 2H, ArH), 7.74 (t, 2H, ArH), 7.20 (s, 1H, ArH), 6.38 (s, 1H, ArH), 4.89 (t, 2H,CH2CF2), 4.05 (t, 2H, cation-OCH2), 2.86 (s, 3H, ArCH3), 1.84 (s, 3H, ArCH3), 1.69 (quin, 2H, CH2), 1.37 (quin, 2H, CH2), 1.24-1.26 (m, 4H, CH2), 0.82 (t, 3H, CH3), ¹⁹F-NMR (DMSO-d6, 376 MHz): δ (ppm) = –111.0. | | | ↑ |

TABLE 6

| Example | Compound | NMR | Salt M⁺X⁻ | Cation | Anion |
|---|---|---|---|---|---|
| 15 | PAG-15 | ¹H-NMR (DMSO-d6, 400 MHz): δ (ppm) = 8.86(d, 2H, ArH), 7.99-8.01(d, 2H, Ar), 7.89(d, 2H, ArH), 7.73-7.76(t, 1H, Ar), 7.58-7.61(t, 2H, Ar), 5.31(s, 2H, SCH2C=O), 4.89(t, 2H, CH2CF2), 3.49-3.62(m, 4H, CH2), 2.18-2.49(m, 4H, CH2S). ¹⁹F-NMR (DMSO-d6, 376 MHz): δ (ppm) = −111.0. | phenyl-C(=O)-CH2-S⁺(tetrahydrothiophene) Br⁻ | phenyl-C(=O)-CH2-S⁺(tetrahydrothiophene) | ↑ |
| 16 | PAG-16 | ¹H-NMR (DMSO-d6, 400 MHz): δ (ppm) = 8.86(d, 2H, ArH), 8.02-8.05(m, 2H, Phenyl), 7.89(d, 2H, ArH), 7.61-7.73(m, 3H, Phenyl), 4.89(t, 2H, CH2CF2), 3.76-3.86(m, 4H, SCH2), 2.09-2.12(m, 2H, CH2), 1.84-1.93(m, 2H, CH2), 1.61-1.70(m, 2H, CH2), ¹⁹F-NMR (DMSO-d6, 376 MHz): δ (ppm) = −111.0. | phenyl-S⁺(tetrahydrothiopyran) Br⁻ | phenyl-S⁺(tetrahydrothiopyran) | ↑ |
| 17 | PAG-17 | ¹H-NMR (DMSO-d6, 400 MHz): δ (ppm) = 8.86(d, 2H, ArH), 8.04-8.09(m, 2H, Phenyl), 7.89(d, 2H, ArH), 7.69-7.79(m, 3H, Phenyl), 4.89(t, 2H, CH2CF2), 3.29(s, 6H, CH3), ¹⁹F-NMR (DMSO-d6, 376 MHz): δ (ppm) = −111.0. | phenyl-S⁺(CH3)2 Br⁻ | phenyl-S⁺(CH3)2 | ↑ |

TABLE 7

| Example | Compound | NMR | Salt M⁺X⁻ | Cation | Anion |
|---|---|---|---|---|---|
| 18 | PAG-18 | ¹H-NMR (DMSO-d6, 400 MHz): δ (ppm) = 8.86(d, 2H, ArH), 8.07(d, 2H, Phenyl), 7.89(d, 2H, ArH), 7.81(d, 2H, Phenyl), 4.89(t, 2H, CH2CF2), 4.10(t, 2H, CH2), 3.59(d, 2H, CH2), 2.20(d, 2H, CH2), 1.71-2.19(m, 4H, CH2), 1.23(s, 9H, t-Bu) ¹⁹F-NMR (DMSO-d6, 376 MHz): δ (ppm) = −111.0. | 4-tBu-phenyl-S⁺(tetrahydrothiopyran) Br⁻ | 4-tBu-phenyl-S⁺(tetrahydrothiopyran) | ↑ |
| 19 | PAG-19 | ¹H-NMR (DMSO-d6, 400 MHz): δ (ppm) = 8.86(d, 2H, ArH), 7.77-7.89(m, 12H, ArH), 7.70(s, 2H, ArH), 5.10(s, 2H, OCOCH2O), 4.89(t, 2H, CH2CF2), 2.07-2.19(m, 9H, CH3) ¹⁹F-NMR (DMSO-d6, 376 MHz): δ (ppm) = −111.0. | 2,6-dimethyl-4-(triphenylsulfonium)phenyl acetoxyacetate Br⁻ | 2,6-dimethyl-4-(triphenylsulfonium)phenyl acetoxyacetate | ↑ |

TABLE 7-continued

| Example | Compound NMR | Salt M+X− | Cation | Anion |
|---|---|---|---|---|
| 20 | PAG-20 | ¹H-NMR (DMSO-d6, 400 MHz): δ (ppm) = 8.86(d, 2H, ArH), 7.89(d, 2H, ArH), 7.84(d, 6H, ArH), 7.78(d, 6H, ArH), 4.89(t, 2H, CH2CF2), 1.33(s, 27H, tBu—CH3) ¹⁹F-NMR (DMSO-d6, 376 MHz): δ (ppm) = −111.0. | | ↑ |

TABLE 8

| Example | Compound NMR | Salt M+X− | Cation | Anion |
|---|---|---|---|---|
| 21 | PAG-21 | ¹H-NMR (DMSO-d6, 400 MHz): δ (ppm) = 8.86(d, 2H, ArH), 7.73-7.89(m, 14H, ArH), 4.89(t, 2H, CH2CF2), 2.38(s, 6H, CH3) ¹⁹F-NMR (DMSO-d6, 376 MHz): δ (ppm) = −70.2, −111.0. | | ↑ |
| 22 | PAG-22 | ¹H-NMR (DMSO-d6, 400 MHz): δ (ppm) = 8.86(d, 2H, ArH), 7.89(d, 2H, ArH), 7.69-7.85(m, 10H, ArH), 7.56(s, 2H, ArH), 4.89(t, 2H, CH2CF2), 4.75(s, 4H, CH2), 2.31(s, 6H, ArCH3), 2.19(m, 2H, Adamantane), 1.47-1.98(m, 15H, Adamantane). ¹⁹F-NMR (DMSO-d6, 376 MHz): δ (ppm) = −−111.0. | | ↑ |

TABLE 9

| Example | Compound | NMR | Salt M⁺X⁻ | Cation | Anion |
|---|---|---|---|---|---|
| 23 | PAG-23 | ¹H-NMR (DMSO-d6, 400 MHz): δ (ppm) = 8.86(d, 2H, ArH), 7.89(d, 2H, ArH), 7.72-7.84(m, 10H, ArH), 7.59(s, 2H, ArH), 4.89(t, 2H, CH2CF2), 4.56(s, 2H, CH2), 2.49(m, 2H, Adamantane), 2.27-2.34(m, 13H, CH3 Adamantane), 1.94-1.97(m, 2H, Adamantane), 1.72-1.79(m, 2H, Adamantane) ¹⁹F-NMR (DMSO-d6, 376 MHz): δ (ppm) = −111.0. | | | ↑ |
| 24 | PAG-24 | ¹H-NMR (DMSO-d6, 400 MHz): δ (ppm) = 8.86(d, 2H, ArH), 7.89(d, 2H, ArH), 7.72-7.84(m, 10H, ArH), 7.59(s, 2H, ArH), 4.89(t, 2H, CH2CF2), 4.64(s, 2H, CH2), 3.70(s, 3H, OCH3), 2.29(s, 6H, CH3). ¹⁹F-NMR (DMSO-d6, 376 MHz): δ (ppm) = −111.0. | | | ↑ |
| 25 | PAG-25 | ¹H-NMR (DMSO-d6, 400 MHz): δ (ppm) = 8.86(d, 2H, ArH), 7.78-7.89(m, 12H, ArH), 7.64(s, 2H, ArH), 4.89(t, 2H, CH2CF2), 3.79(s, 3H, OCH3), 2.32(s, 6H, CH3) ¹⁹F-NMR (DMSO-d6, 376 MHz): δ (ppm) = −111.0. | | | ↑ |

TABLE 10

| Example | Compound | NMR | Salt M⁺X⁻ |
|---|---|---|---|
| 26 | PAG-26 | ¹H-NMR (DMSO-d6, 400 MHz): δ (ppm) = 8.86(d, 4H, ArH), 8.44(s, 4H, ArH in ArC=O), 7.78-7.90(m, 28H, ArH), 4.89(t, 4H, CH2CF2), 2.23(s, 12H, CH3).<br>¹⁹F-NMR (DMSO-d6, 376 MHz): δ (ppm) = −111.0. | |
| 27 | PAG-27 | ¹H-NMR (DMSO-d6, 400 MHz): δ (ppm) = 8.90(s, 1H, ArH in ArC=O), 8.86(d, 4H, ArH), 8.60(dd, 2H, ArH in ArC=O), 7.77-7.96(m, 29H, ArH in cation + ArH in ArC=O + ArF in Pyridine), 4.89(t, 4H, CH2CF2), 2.24(s, 12H, CH3).<br>¹⁹F-NMR (DMSO-d6, 376 MHz): δ (ppm) = −111.0. | |

TABLE 10-continued

| Example | Compound | Cation | Anion |
|---|---|---|---|
| 26 | PAG-26 | (structure) | ↑ |
| 27 | PAG-27 | (structure) | ↑ |

TABLE 11

| Example | Compound | NMR | Salt M⁺X⁻ | Cation | Anion |
|---|---|---|---|---|---|
| 28 | PAG-28 | ¹H-NMR (DMSO-d6, 400 MHz): δ (ppm) = 8.86(d, 2H, ArH), 7.89(d, 2H, ArH), 7.76-7.87(m, 10H, ArH), 7.69(s, 2H, ArH), 4.89(t, 2H, CH2CF2), 2.13(s, 6H, CH3), 1.66-2.03(m, 15H, Adamantane) ¹⁹F-NMR (DMSO-d6, 376 MHz): δ (ppm) = −111.0. | | | ↑ |
| 29 | PAG-29 | ¹H-NMR (DMSO-d6, 400 MHz): δ (ppm) = 8.86(d, 2H, ArH), 7.79-7.93(m, 14H, ArH), 4.89(t, 2H, CH2CF2), 2.73(t, 2H, CO—CH2), 2.19(s, 6H, ArCH3), 1.65-1.72(m, 2H, CH2), 1.25-1.38(m, 14H, CH2), 0.85(t, 3H, CH3). ¹⁹F-NMR (DMSO-d6, 376 MHz): δ (ppm) = −111.0. | | | ↑ |
| 30 | PAG-30 | ¹H-NMR (DMSO-d6, 400 MHz): δ (ppm) = 8.86(d, 2H, ArH), 8.76(s, 1H, ArH), 8.59-8.64(m, 1H, ArH), 8.42(t, 2H, ArH), 8.03-8.19(m, 5H, ArH), 7.89(d, 2H, ArH), 7.81(t, 1H, ArH), 7.69(t, 2H, ArH), 4.89(t, 2H, CH2CF2). ¹⁹F-NMR (DMSO-d6, 376 MHz): δ (ppm) = −62.1, −111.0. | | | ↑ |

TABLE 12

| Example | Compound | NMR | Salt M⁺X⁻ | Cation | Anion |
|---|---|---|---|---|---|
| 31 | PAG-31 | ¹H-NMR (DMSO-d6, 400 MHz): δ (ppm) = 8.86(d, 2H, ArH), 7.89(d, 2H, ArH) 4.89(t, 2H, CH2CF2), 3.36(t, 6H, CH2), 1.68(quintet, 6H, CH2), 1.35-1.44(m, 6H, CH2), 0.81-0.93(m, 9H, CH3). ¹⁹F-NMR (DMSO-d6, 376 MHz): δ (ppm) = −111.0. | | | ↑ |

TABLE 12-continued

| Example | Compound | NMR | Salt M+X− | Cation | Anion |
|---|---|---|---|---|---|
| 32 | PAG-32 | ¹H-NMR (DMSO-d6, 400 MHz): δ (ppm) = 8.86(d, 2H, ArH), 8.29(d, 4H, ArH), 7.93-8.09(m, 6H, ArH), 7.89(d, 2H, ArH), 4.89(t, 2H, CH2CF2). ¹⁹F-NMR (DMSO-d6, 376 MHz): δ (ppm) = −47.9, −111.0. | | | ↑ |
| 33 | PAG-33 | ¹H-NMR (DMSO-d6, 400 MHz): δ (ppm) = 8.86(d, 2H, ArH), 7.89-8.24(m, 9H, ArH), 4.89(t, 2H, CH2CF2), 3.85(s, 3H, OCH3), 2.40(s, 6H, ArCH3). ¹⁹F-NMR (DMSO-d6, 376 MHz): δ (ppm) = −48.8, −111.0. | | | ↑ |

TABLE 13

| Example | Compound | NMR | Salt M+X− | Cation | Anion |
|---|---|---|---|---|---|
| 34 | PAG-34 | ¹H-NMR (DMSO-d6, 400 MHz): δ (ppm) = 10.12(s, 1H, OH), 8.86(d, 2H, ArH), 7.89-8.24(m, 9H, ArH), 4.89(t, 2H, CH2CF2), 2.40(s, 6H, ArCH3). ¹⁹F-NMR (DMSO-d6, 376 MHz): δ (ppm) = −48.2, −111.0. | | | ↑ |
| 35 | PAG-35 | ¹H-NMR (DMSO-d6, 400 MHz): δ (ppm) = 8.86(d, 2H, ArH), 8.49(d, 2H, ArH), 8.30(d, 2H, ArH), 7.93(t, 2H, ArH), 7.89(d, 2H, ArH), 7.73(t, 2H, ArH), 7.30(s, 2H, ArH), 4.89(t, 2H, CH2CF2), 4.52(s, 2H, OCH2), 2.16-2.24(m, 8H, Ar—CH3 + Adamantane), 1.44-1.92(m, 15H, Adamantane + CH3). ¹⁹F-NMR (DMSO-d6, 376 MHz): δ (ppm) = −111.0. | | | ↑ |
| 36 | PAG-36 | ¹H-NMR (DMSO-d6, 400 MHz): δ (ppm) = 9.73(br s, 1H, OH), 8.86(d, 2H, ArH), 8.47(d, 2H, ArH), 8.24(d, 2H, ArH), 7.91(t, 2H, ArH), 7.89(d, 2H, ArH), 7.71(t, 2H, ArH), 7.18(s, 2H, ArH), 4.89(t, 2H, CH2CF2), 2.10(s, 6H, ArCH3). ¹⁹F-NMR (DMSO-d6, 376 MHz): δ (ppm) = −111.0. | | | ↑ |

TABLE 14

| Example | Compound NMR | Salt M⁺X⁻ | Cation | Anion |
|---|---|---|---|---|
| 37 | PAG-37 | ¹H-NMR (DMSO-d6, 400 MHz): δ (ppm) = 8.86(d, 2H, ArH), 7.89(d, 2H, ArH), 7.75-7.87(m, 10H, ArH), 7.62(s, 2H, ArH), 4.89(t, 2H, CH2CF2), 3.97(t, 2H, CH2), 2.03-2.56(m, 10H, CH2, CH3). ¹⁹F-NMR (DMSO-d6, 376 MHz): δ (ppm) = −123.5, −121.8, −111.6, −111.0, −78.3. | [structure with Br⁻] | [cation structure] | ↑ |
| 38 | PAG-38 | ¹H-NMR (DMSO-d6, 400 MHz): δ (ppm) = 8.86(d, 2H, ArH), 7.89(d, 2H, ArH), 7.75-7.86(m, 10H, ArH), 7.60(s, 2H, ArH), 4.89(t, 2H, CH2CF2), 3.87(t, 2H, CH2), 2.40(m, 2H, CH2), 2.24-2.35(m, 6H, CH2), 2.12(m, 6H, N—CH3), 1.86(t, 2H, CH2). ¹⁹F-NMR (DMSO-d6, 376 MHz): δ (ppm) = −111.0. | [structure with Br⁻] | [cation structure] | ↑ |
| 39 | PAG-39 | ¹H-NMR (DMSO-d6, 400 MHz): δ (ppm) = 8.86(d, 2H, ArH), 7.77-7.89(m, 12H, ArH), 7.71(s, 2H, ArH), 4.89(t, 2H, CH2CF2), 2.51(s, 2H, CH2), 2.20(s, 6H, CH3), 1.97(s, 3H, Adamantane), 1.62-1.73(m, 12H, Adamantane). ¹⁹F-NMR (DMSO-d6, 376 MHz): δ (ppm) = −111.0. | [structure with Br⁻] | [cation structure] | ↑ |

TABLE 15

| Example | Compound | NMR | Salt M+X− | Cation | Anion |
|---|---|---|---|---|---|
| 40 | PAG-40 | ¹H-NMR (DMSO-d6, 400 MHz): δ (ppm) = 8.86(d, 2H, ArH), 7.89(d, 2H, ArH), 7.74-7.84(m, 10H, ArH), 7.61(s, 2H, ArH), 4.89(t, 2H, CH2CF2), 4.49-4.66(m, 4H, norbornane + OCH2), 3.24(m, 1H, norbornane), 2.44-2.54(m, 2H, norbornane), 2.37(s, 6H, ArCH3), 1.91-2.06(m, 2H, norbornane), 1.57-1.67(m, 2H, norbornane). ¹⁹F-NMR (DMSO-d6, 376 MHz): δ (ppm) = −111.0. | Br⊖ | | ↑ |
| 41 | PAG-41 | ¹H-NMR (DMSO-d6, 400 MHz): δ (ppm) = 8.86(d, 2H, ArH), 7.80-7.92(m, 12H, ArH), 7.67(s, 2H, ArH), 4.89(t, 2H, CH2CF2), 4.66(s, 2H, CH2), 2.37(s, 6H, ArCH3), 2.13-2.16(m, 2H, cyclohexyl), 1.93(q, 2H, CH2), 1.14-1.57(m, 8H, cyclohexyl), 0.84(t, 3H, CH3). ¹⁹F-NMR (DMSO-d6, 376 MHz): δ (ppm) = −111.0. | Br⊖ | | ↑ |
| 42 | PAG-42 | ¹H-NMR (DMSO-d6, 400 MHz): δ (ppm) = 8.86(d, 2H, ArH), 8.44(d, 1H, ArH), 8.22(m, 2H, ArH), 7.73-7.89(m, 15H, ArH), 7.50(d, 1H, ArH), 4.89(t, 2H, CH2CF2). ¹⁹F-NMR (DMSO-d6, 376 MHz): δ (ppm) = −111.0. | Br⊖ | | ↑ |

TABLE 16

| Example | Compound | NMR | Salt M+X− | Cation | Anion |
|---|---|---|---|---|---|
| 43 | PAG-43 | ¹H-NMR (DMSO-d6, 400 MHz): δ (ppm) = 8.86(d, 2H, ArH), 8.24(d, 4H, ArH), 7.89(d, 2H, ArH), 7.59(t, 2H, ArH), 7.47(t, 4H, ArH), 4.89(t, 2H, CH2CF2). ¹⁹F-NMR (DMSO-d6, 376 MHz): δ (ppm) = −111.0. | Br⊖ | | ↑ |

TABLE 16-continued

| Example | Compound NMR | Salt M⁺X⁻ | Cation | Anion |
|---|---|---|---|---|
| 44 | PAG-44 ¹H-NMR (DMSO-d6, 400 MHz): δ (ppm) = 8.86(d, 2H, ArH), 8.55(d, 2H, ArH), 8.38(d, 2H, ArH), 8.32(d, 2H, ArH), 8.03(d, 2H, ArH), 7.93-7.97(m, 1H, ArH), 7.82-7.89(m, 10H, ArH), 7.55(d, 2H, ArH), 4.89(t, 2H, CH2CF2). ¹⁹F-NMR (DMSO-d6, 376 MHz): δ (ppm) = −111.0. | | | ↑ |
| 45 | PAG-45 ¹H-NMR (DMSO-d6, 400 MHz): δ (ppm) = 8.86(d, 2H, ArH), 7.89(d, 2H, ArH), 4.89(t, 2H, CH2CF2), 4.46(s, 2H, CH2(C=O)), 3.38-3.58(m, 4H, CH2SCH2), 1.56-2.33(m, 21H, Ad + CH2CH2) ¹⁹F-NMR (DMSO-d6, 376 MHz): δ (ppm) = −111.0. | | | ↑ |

TABLE 17

| Example | Compound NMR | Salt M⁺X⁻ | Cation | Anion |
|---|---|---|---|---|
| 46 | PAG-46 ¹H-NMR (DMSO-d6, 400 MHz): δ (ppm) = 8.86(d, 2H, ArH), 7.89(d, 2H, ArH), 7.75(s, 2H, Ar), 4.89(t, 2H, CH2CF2), 3.91-3.96(m, 2H, CH2), 3.72-3.79(m, 2H, CH2), 2.29-2.41(m, 4H, CH2), 1.75-2.19(m, 21H, Ar—CH3 + Adamantane). ¹⁹F-NMR (DMSO-d6, 376 MHz): δ (ppm) = −111.0. | | | ↑ |
| 47 | PAG-47 ¹H-NMR (DMSO-d6, 400 MHz): δ (ppm) = 8.86(d, 2H, ArH), 7.89(d, 2H, ArH), 7.82 (m, 2H, Ar), 4.89(t, 2H, CH2CF2), 3.73-3.91(m, 4H, CH2), 1.56-2.43(m, 27H, Ar—CH3 + CH2 + adamantane). ¹⁹F-NMR (DMSO-d6, 376 MHz): δ (ppm) = −111.0. | | | ↑ |

TABLE 17-continued

| Example | Compound | NMR | Salt M⁺X⁻ | Cation | Anion |
|---|---|---|---|---|---|
| 48 | PAG-48 | ¹H-NMR (DMSO-d6, 400 MHz): δ (ppm) = 8.86(d, 2H, ArH), 8.23(d, 4H, ArH), 7.98(d, 4H, ArH), 7.89(d, 2H, ArH), 4.89(t, 2H, CH2CF2), 1.37(s, 18H, CH3 of tert-butyl). ¹⁹F-NMR (DMSO-d6, 376 MHz): δ (ppm) = −48.5, −111.0. | 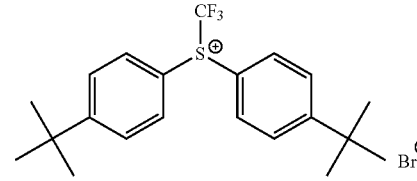 | 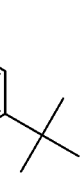 | ↑ |

TABLE 18

| Example | Compound | NMR | Salt M⁺X⁻ | Cation | Anion |
|---|---|---|---|---|---|
| 49 | PAG-49 | ¹H-NMR (DMSO-d6, 400 MHz): δ (ppm) = 8.86(d, 2H, ArH), 7.77-7.89(m, 12H, ArH), 7.64(s, 2H, ArH), 4.89(t, 2H, CH2CF2), 4.57(s, 2H, CH2O), 2.40(s, 6H, CH3), 2.02-2.26(m, 9H, Adamantane), 1.76(br s, 6H, Adamantane). ¹⁹F-NMR (DMSO-d6, 376 MHz): δ (ppm) = −111.0. | 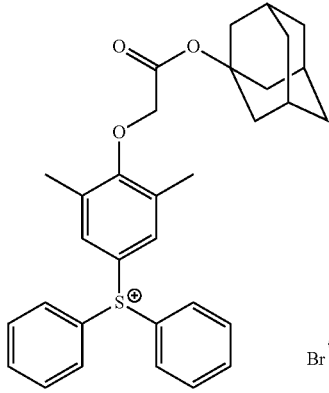 [SMILES: Cc1cc([S+](c2ccccc2)c2ccccc2)cc(C)c1OCC(=O)OC12CC3CC(CC(C3)C1)C2] |  | ↑ |
| 50 | PAG-50 | ¹H-NMR (DMSO-d6, 400 MHz): δ (ppm) = 8.86(d, 2H, ArH), 7.77-7.89(m, 12H, ArH), 7.64(s, 2H, ArH), 5.70(t, 1H, OCHC=O), 4.89(t, 2H, CH2CF2), 4.82(s, 2H, ArOCH2), 4.46-4.30(m, 2H, OCOCH2), 2.71-2.64(m, 1H, OCH2CH2), 2.33-2.24(m, 7H, CH3 + OCH2CH2). ¹⁹F-NMR (DMSO-d6, 376 MHz): δ (ppm) = −111.0. | 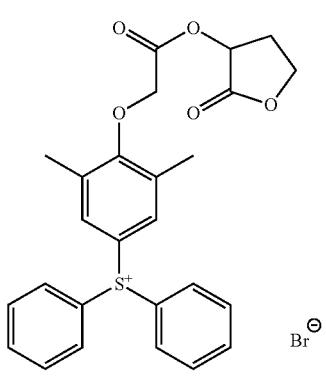 [SMILES: Cc1cc([S+](c2ccccc2)c2ccccc2)cc(C)c1OCC(=O)OC1CCOC1=O ; [Br-]] |  | ↑ |
| 51 | PAG-51 | ¹H-NMR (DMSO-d6, 400 MHz): δ (ppm) = 8.86(d, 2H, ArH), 8.28(d, 2H, ArH), 8.11(d, 1H, ArH), 7.89(d, 2H, ArH), 7.86(t, 1H, ArH), 7.63-7.81(m, 7H, ArH), 4.89(t, 2H, CH2CF2). ¹⁹F-NMR (DMSO-d6, 376 MHz): δ (ppm) = −111.0. | 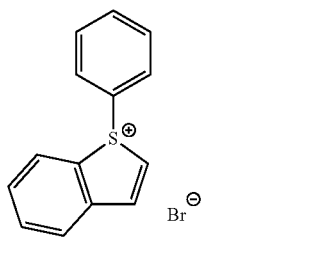 [SMILES: c1ccc(-[s+]2ccc3ccccc32)cc1 ; [Br-]] |  | ↑ |

TABLE 19

| Example | Compound NMR | Salt M+X− | Cation | Anion |
|---|---|---|---|---|
| 52 | PAG-52 ¹H-NMR (DMSO-d6, 400 MHz): δ (ppm) = 8.86(d, 2H, ArH), 8.05(d, 2H, ArH), 7.89(d, 2H, ArH), 7.74(d, 2H, ArH), 4.89(t, 2H, CH2CF2), 3.85(s, 3H, S—CH3), 1.30(s, 18H, t-Bu). ¹⁹F-NMR (DMSO-d6, 376 MHz): δ (ppm) = −111.0. | | | ↑ |
| 53 | PAG-53 ¹H-NMR (DMSO-d6, 400 MHz): δ (ppm) = 8.86(d, 2H, ArH), 8.41(m, 2H, ArH), 8.12(d, 1H, ArH), 7.73-7.93(m, 4H, ArH), 7.19(d, 1H, ArH), 5.23(s, 2H, CH2), 4.95(m, 1H, Adamantane), 4.89(t, 2H, CH2CF2), 4.03(m, 2H, CH2S), 3.75(m, 2H, CH2S), 2.27-2.43(m, 4H, SCH2CH2), 1.42-1.99(m, 14H, Adamantane). ¹⁹F-NMR (DMSO-d6, 376 MHz): δ (ppm) = −111.0. | | | ↑ |
| 54 | PAG-54 ¹H-NMR (DMSO-d6, 400 MHz): δ (ppm) = 8.86(d, 2H, ArH), 8.42(m, 2H, ArH), 8.17(d, 1H, ArH), 7.78-7.91(m, 4H, ArH), 7.23(d, 1H, ArH), 5.26(s, 2H, CH2), 4.89(t, 2H, CH2CF2), 3.75-4.19(m, 7H, SCH2 + CH3), 2.29-2.60(m, 4H, SCH2CH2). ¹⁹F-NMR (DMSO-d6, 376 MHz): δ (ppm) = −111.0. | | | ↑ |

TABLE 20

| Example | Compound | NMR | Salt M⁺X⁻ Cation | Anion |
|---|---|---|---|---|
| 55 | PAG-55 | $^1$H-NMR (DMSO-d6, 400 MHz): δ (ppm) = 8.86(d, 4H, ArH), 8.28(d, 2H, ArH), 8.12(d, 1H, ArH), 7.85-7.91(m, 3H, ArH), 7.80(d, 1H, ArH), 7.62-7.74(m, 5H, ArH), 4.89(t, 2H, CH2CF2), 1.27(s, 9H, CH3). $^{19}$F-NMR (DMSO-d6, 376 MHz): δ (ppm) = −111.0. | Bis(4-tert-butylphenyl-benzothiophenium) Br⁻ | ↑ |
| 56 | PAG-56 | $^1$H-NMR (DMSO-d6, 400 MHz): δ (ppm) = 8.86(d, 2H, ArH), 7.76-7.90(m, 14H, ArH), 4.89(t, 2H, CH2CF2), 2.62-2.69(m, 1H, camphene), 2.08-2.26(m, 8H, Ar—CH3 + camphene), 1.65-1.72(m, 1H, camphene), 1.19(s, 3H, CH3), 1.09(s, 3H, CH3), 1.04(s, 3H, CH3). $^{19}$F-NMR (DMSO-d6, 376 MHz): δ (ppm) = −111.0. | Bis(camphanoyloxy-dimethylphenyl-diphenylsulfonium) Br⁻ | ↑ |

<Production of Positive Resist Composition>

The components shown in Table 21 were mixed together and dissolved to obtain positive resist compositions.

TABLE 21

| | Component (A) | Component (B) | Component (C) | Component (C) | Component (S) |
|---|---|---|---|---|---|
| Comp. Ex. 1 | (A)-1 [100] | (B)-1 [8.50] | — | — | (C)-7 [1.20] | (S)-1 [2,220] |
| Comp. Ex. 2 | (A)-1 [100] | (B)-1 [8.50] | — | (C)-1 [2.61] | — | (S)-1 [2,220] |
| Comp. Ex. 3 | (A)-1 [100] | (B)-1 [8.50] | — | (C)-2 [3.10] | — | (S)-1 [2,220] |
| Comp. Ex. 4 | (A)-1 [100] | (B)-1 [8.50] | — | (C)-3 [3.82] | — | (S)-1 [2,220] |
| Comp. Ex. 5 | (A)-2 [100] | (B)-1 [8.50] | — | (C)-3 [3.82] | — | (S)-1 [2,220] |
| Comp. Ex. 6 | (A)-2 [100] | (B)-2 [11.56] | — | (C)-3 [3.82] | — | (S)-1 [2,220] |
| Ex. 57 | (A)-1 [100] | (B)-1 [8.50] | — | (C)-4 [2.79] | — | (S)-1 [2,220] |
| Ex. 58 | (A)-1 [100] | (B)-1 [8.50] | — | (C)-5 [2.82] | — | (S)-1 [2,220] |
| Ex. 59 | (A)-1 [100] | (B)-1 [8.50] | — | (C)-6 [3.88] | — | (S)-1 [2,220] |

TABLE 21-continued

| | Component (A) | Component (B) | | Component (C) | | Component (S) |
|---|---|---|---|---|---|---|
| Ex. 60 | (A)-1 [100] | (B)-1 [5.72] | (B)-2 [4.29] | (C)-4 [2.79] | — | (S)-1 [2,220] |
| Ex. 61 | (A)-1 [100] | (B)-1 [8.50] | — | (C)-4 [2.79] | (C)-7 [0.30] | (S)-1 [2,220] |
| Ex. 62 | (A)-2 [100] | (B)-1 [8.50] | — | (C)-4 [2.79] | — | (S)-1 [2,220] |
| Ex. 63 | (A)-2 [100] | (B)-2 [11.56] | — | (C)-4 [2.79] | — | (S)-1 [2,220] |
| Ex. 64 | (A)-2 [100] | (B)-2 [11.56] | — | (C)-6 [3.88] | — | (S)-1 [2,220] |

In Table 21, the reference characters indicate the following. Further, the values in brackets [ ] indicate the amount (in terms of parts by weight) of the component added.

(A)-1: a copolymer (A1-11-1) represented by chemical formula shown below. Mw=7,000, Mw/Mn=1.70. In the chemical formula, the subscript numerals shown on the bottom right of the parentheses ( ) indicate the percentage (mol %) of the respective structural units.

[Chemical Formula 92]

(A1-11-1)

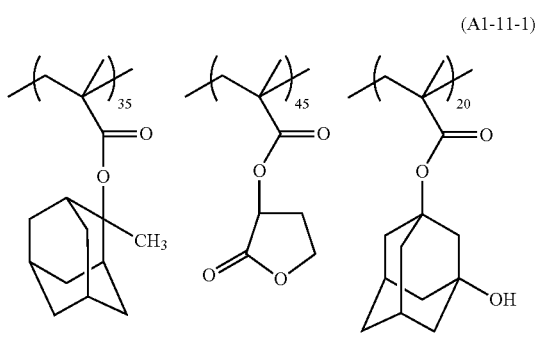

(A)-2: a copolymer (A1-13-1) represented by chemical formula shown below. Mw=6,900, Mw/Mn=1.61. In the chemical formula, the subscript numerals shown on the bottom right of the parentheses ( ) indicate the percentage (mol %) of the respective structural units.

[Chemical Formula 93]

(A1-13-1)

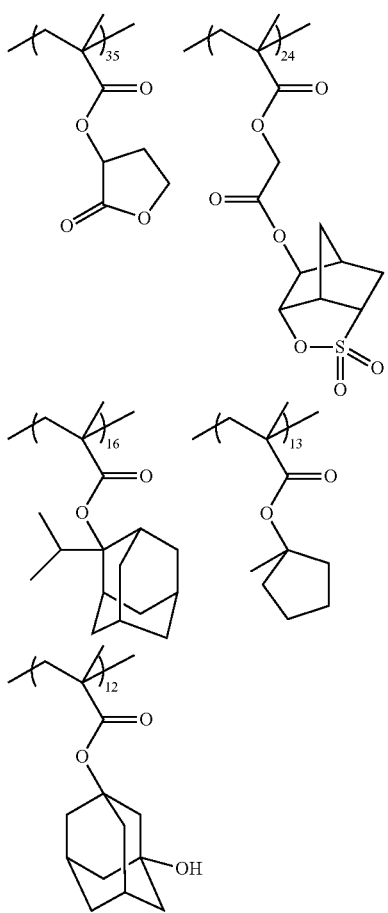

(B)-1: a compound represented by formula (B)-1 shown below.

(B)-2: a compound represented by formula (B)-2 shown below.

[Chemical Formula 94]

(B)-1

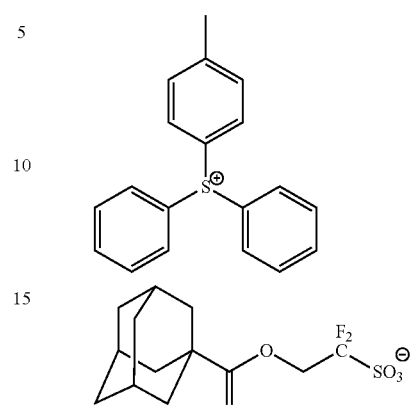

[Chemical Formula 95]

(B)-2

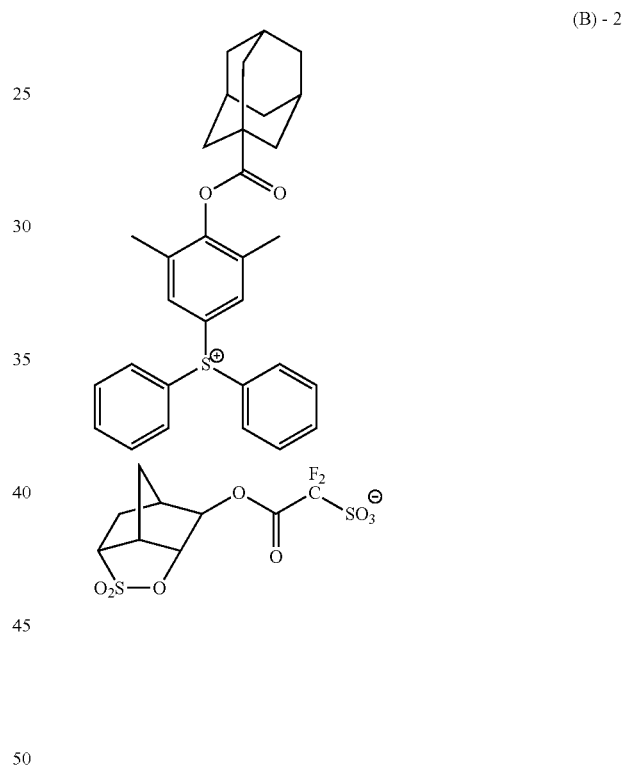

(C)-1: a compound represented by formula (C)-1 shown below.

(C)-2: a compound represented by formula (C)-2 shown below.

(C)-3: a compound represented by formula (C)-3 shown below.

(C)-4: a compound represented by formula (C)-4 shown below.

(C)-5: a compound represented by formula (C)-5 shown below.

(C)-6: a compound represented by formula (C)-6 shown below.

(C)-7: a compound represented by formula (C)-7 shown below.

[Chemical Formula 96]

(C)-1

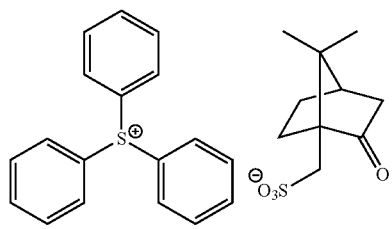

[Chemical Formula 97]

(C)-2

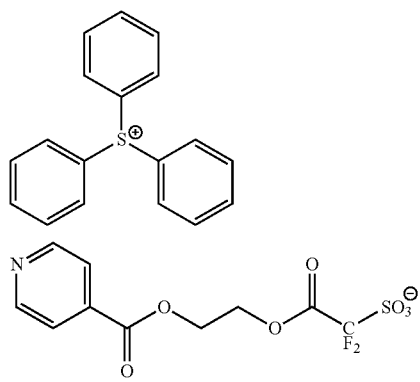

[Chemical Formula 98]

(C)-3

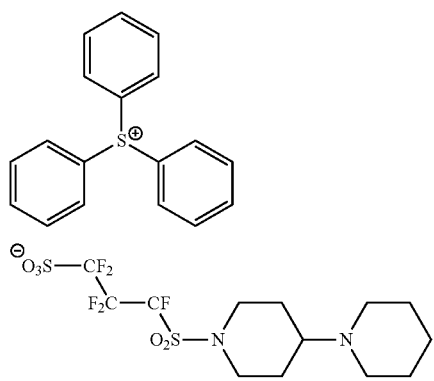

[Chemical Formula 99]

(C)-4

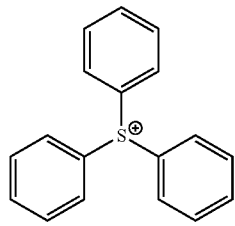

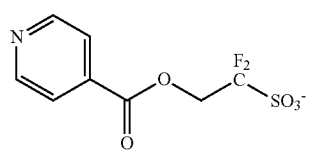

[Chemical Formula 100]

(C)-5

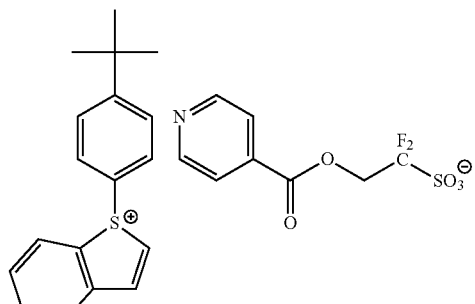

[Chemical Formula 101]

(C)-6

[Chemical Formula 102]

(C)-7

(S)-1: a mixed solvent of PGMEA/PGME=6/4 (weight ratio).

<Evaluation of Lithography Properties and Shape of Resist Pattern>

Using the obtained positive resist compositions, resist patterns were formed in the following manner, and the following evaluations were conducted.

[Formation of Resist Pattern]

An organic anti-reflection film composition (product name: ARC-29A, manufactured by Brewer Science Ltd.) was applied onto an 8-inch silicon wafer using a spinner, and the composition was then baked and dried on a hotplate at 205° C.

for 60 seconds, thereby forming an organic anti-reflection film having a film thickness of 82 nm.

Then, each of the positive resist composition obtained above was applied onto the thus formed anti-reflection film using a spinner, and was then prebaked (PAB) on a hotplate at the PAB temperature indicated in Table 22 for 60 seconds and dried, thereby forming a resist film having a film thickness of 150 nm.

Subsequently, the resist film was selectively irradiated with an ArF excimer laser (193 nm) through a mask (6% half tone), using an ArF exposure apparatus NSR-S302 (manufactured by Nikon Corporation; NA (numerical aperture)=0.60, ⅔ annular illumination).

Thereafter, a post exposure bake (PEB) treatment was conducted at the PEB temperature indicated in Table 22 for 60 seconds, followed by alkali development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was rinsed for 30 seconds with pure water, followed by drying by shaking.

As a result, in each of the examples, a space and line resist pattern (hereafter, referred to as "SL pattern") in which spaces having a width of 120 nm were arranged at equal intervals (pitch: 240 nm) was formed on the resist film.

The optimum exposure dose (namely, sensitivity: Eop, mJ/cm$^2$) with which such SL patterns were formed was determined. The results are shown in Table 2.

[Evaluation of Line Width Roughness (LWR)]

With respect to each of the SL patterns having a space width of 120 nm and a pitch of 240 nm that was formed with the above Eop in accordance with the same procedure for forming the resist patterns as described above, the space width in the lengthwise direction of the space were measured at 400 points using a measuring scanning electron microscope (SEM) (product name: S-9220, manufactured by Hitachi, Ltd.; acceleration voltage: 800V). From the results, the value of 3 times the standard deviation s (i.e., 3s) was determined, and the average of the 3s values at 5 points was calculated as a yardstick of LWR. The results are shown in Table 22.

The smaller this 3s value is, the lower the level of roughness of the line width, indicating that an SL pattern with a uniform width was obtained.

[Evaluation of Mask Error Factor (MEF)]

In accordance with the same procedure for forming the resist patterns as described above, with the above Eop, SL patterns were formed using a mask pattern targeting a space width of 120 nm and a pitch of 260 nm, and a mask pattern targeting a space width of 130 nm and a pitch of 260 nm, and the MEF value was calculated by the following formula. The results are shown in Table 22.

$$\text{MEF} = |CD_{130} - CD_{120}| / |MD_{130} - MD_{120}|$$

In this formula, $CD_{130}$ and $CD_{120}$ represent the respective space widths (nm) of the actual SL patterns respectively formed using the mask pattern targeting a space width of 120 nm and the mask pattern targeting a space width of 130 nm, and $MD_{130}$ and $MD_{120}$ represent the respective target space widths (nm), meaning $MD_{130}=130$ and $MD_{120}=120$.

An MEF value closer to 1 indicates that a resist pattern faithful to the mask pattern was formed.

[Evaluation of Exposure Latitude (EL Margin)]

With respect to the above Eop, the exposure dose with which an SL pattern having a space within the range of target dimension (space width: 120 nm)±5% (i.e., 114 nm to 126 nm) was formed was determined, and the EL margin (unit: %) was determined by the following formula. The results are shown in Table 22.

$$\text{EL margin}(\%) = (|E1 - E2|/Eop) \times 100$$

E1: Exposure dose (mJ/cm$^2$) with which an SL pattern having a space width of 114 nm was formed.

E2: Exposure dose (mJ/cm$^2$) with which an SL pattern having a space width of 126 nm was formed.

The larger the value of EL margin, the smaller the fluctuation in the pattern size accompanied by the variation in the exposure dose.

[Evaluation of Resist Pattern Shape]

SL patterns having a space width of 120 nm and a pitch of 240 nm that were formed with the above Eop were observed using a scanning electron microscope (SEM), and the cross sectional shape of the SL patterns was evaluated. The results are shown in Table 22.

TABLE 22

| | PAB temp. (° C.) | PEB temp. (° C.) | Sensitivity (mJ/cm$^2$) | LWR (nm) | MEF | EL margin (%) | Resist pattern shape |
|---|---|---|---|---|---|---|---|
| Comp. Ex. 1 | 110 | 110 | 33.9 | 15.9 | 2.61 | 6.39 | T-top |
| Comp. Ex. 2 | 110 | 110 | 26.7 | 14.5 | 2.55 | 6.34 | Round top shape |
| Comp. Ex. 3 | 110 | 110 | 31.2 | 13.9 | 2.68 | 5.87 | Round top shape |
| Comp. Ex. 4 | 110 | 110 | 34.7 | 14.8 | 2.77 | 6.04 | Round top shape |
| Comp. Ex. 5 | 90 | 90 | 36.1 | 13.7 | 2.66 | 6.31 | Round top shape |
| Comp. Ex. 6 | 90 | 90 | 39.8 | 13.4 | 2.59 | 6.42 | T-top |
| Ex. 57 | 110 | 110 | 32.6 | 12.9 | 2.53 | 6.53 | Rectangular |
| Ex. 58 | 110 | 110 | 38.9 | 11.6 | 2.49 | 6.47 | Rectangular |
| Ex. 59 | 110 | 110 | 34.7 | 12.3 | 2.50 | 6.71 | Rectangular |
| Ex. 60 | 110 | 110 | 35.2 | 11.8 | 2.53 | 6.56 | Rectangular |
| Ex. 61 | 110 | 110 | 35.5 | 11.9 | 2.50 | 6.60 | Rectangular |
| Ex. 62 | 90 | 90 | 35.1 | 11.7 | 2.40 | 7.04 | Rectangular |
| Ex. 63 | 90 | 90 | 38.9 | 10.9 | 2.37 | 7.11 | Rectangular |
| Ex. 64 | 90 | 90 | 39.5 | 10.5 | 2.41 | 6.99 | Rectangular |

As seen from the results in Table 22, it was confirmed that the resist patterns formed using the resist compositions of Examples 57 to 64 exhibited superior lithography properties in terms of LWR, MEF and EL margin, and having an excellent shape with high rectangularity, as compared to the resist patterns formed using the resist compositions of Comparative Examples 1 to 6.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A resist composition comprising:
   a base component (A) which exhibits changed solubility in a developing solution under action of acid;
   a nitrogen-containing organic compound component (C) containing a compound (C1) represented by general formula (c1) shown below; and
   an acid generator component (B) which generates acid upon exposure, provided that said compound (C1) is excluded from the acid generator component (B):

(c1)

wherein $R^N$ represents a nitrogen-containing heterocyclic group having aromaticity which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $M^+$ represents an organic cation.

2. The resist composition according to claim 1, wherein said base component (A) is a base component (A0) which exhibits increased polarity by action of acid.

3. The resist composition according to claim 2, wherein said base component (A0) contains a resin component (A1) that includes a structural unit (a1) derived from an acrylate ester in which the hydrogen atom bonded to the carbon atom on the α-position may be substituted with a substituent, and containing an acid decomposable group that exhibits increased polarity by action of acid.

4. The resist composition according to claim 3, wherein said resin component (A1) further comprises at least one type of structural unit (a2) derived from an acrylate ester in which the hydrogen atom bonded to the carbon atom on the α-position may be substituted with a substituent,
wherein said structural unit (a2) is selected from the group consisting of a structural unit (a2$^L$) containing a lactone-containing cyclic group and a structural unit (a2$^S$) containing a —SO$_2$-containing cyclic group.

5. The resist composition according to claim 3, wherein said resin component (A1) also includes a structural unit (a3) derived from an acrylate ester in which the hydrogen atom bonded to the carbon atom on the α-position may be substituted with a substituent, and containing a polar group-containing aliphatic hydrocarbon group.

6. The resist composition according to claim 1, wherein said nitrogen-containing organic compound component (C) also includes a nitrogen-containing organic compound component (C2) which does not fall under the definition of said component (C1).

7. A method of forming a resist pattern, comprising:
   applying the resist composition of any one of claims 1 to 6 to a substrate to form a resist film on the substrate;
   exposing said resist film; and
   developing said resist film to form a resist pattern.

8. A compound represented by general formula (c1') shown below:

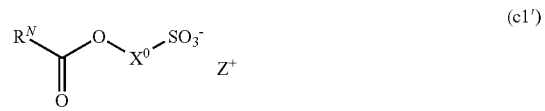
(c1')

wherein $R^N$ represents a nitrogen-containing heterocyclic group having aromaticity which may have a substituent; $X^0$ represents a linear or branched divalent aliphatic hydrocarbon group of 1 to 10 carbon atoms, a cyclic divalent aliphatic hydrocarbon group of 3 to 20 carbon atoms or a divalent aliphatic hydrocarbon group of 3 to 20 carbon having a cyclic partial structure, or any one of these groups in which some or all of the hydrogen atoms thereof have been substituted with fluorine atoms; and $Z^+$ represents an organic cation or a metal cation.

9. The resist composition according to claim 1, wherein, in the formula (c1'), $R^N$—C(=O)—O— represents a group selected from the group consisting of groups shown below:

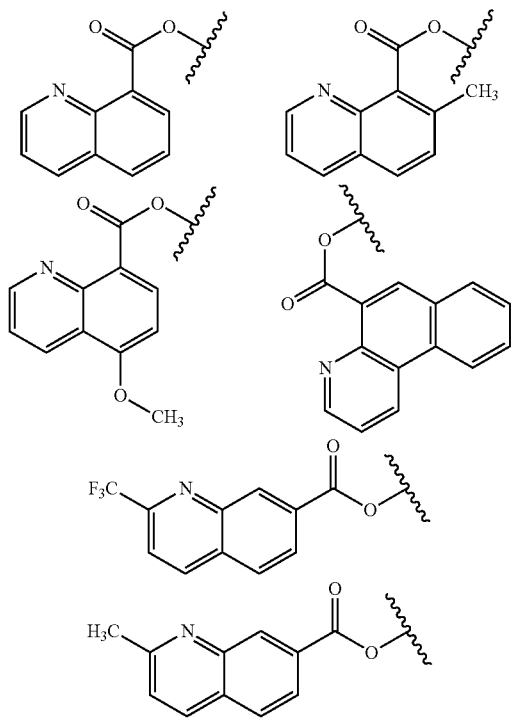

-continued
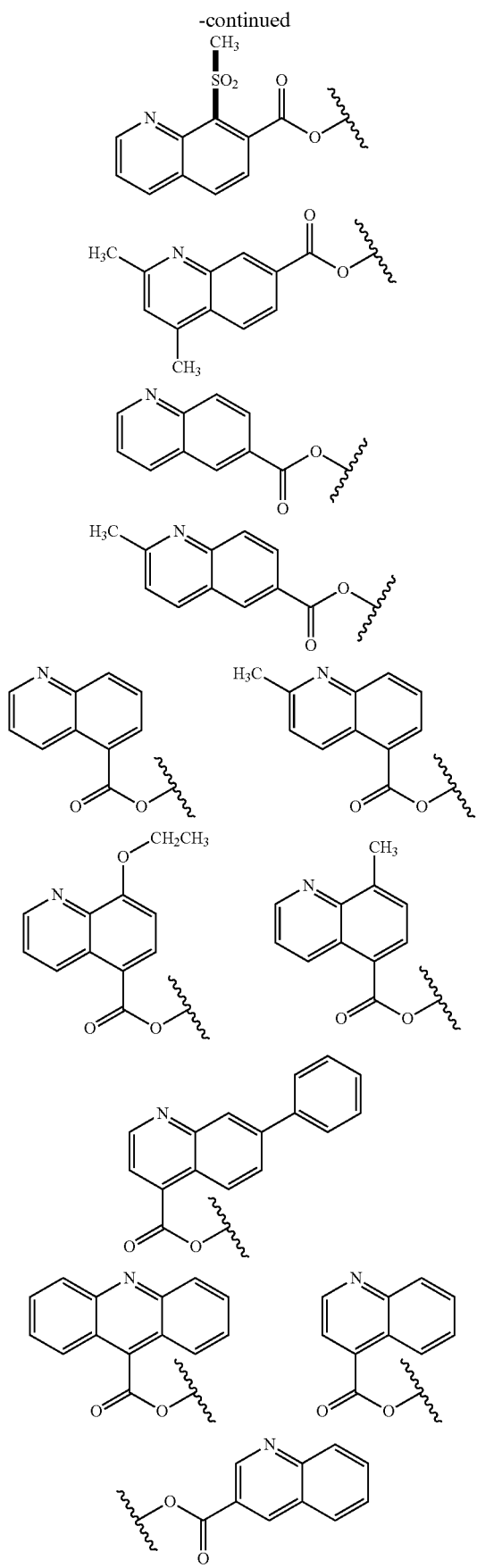
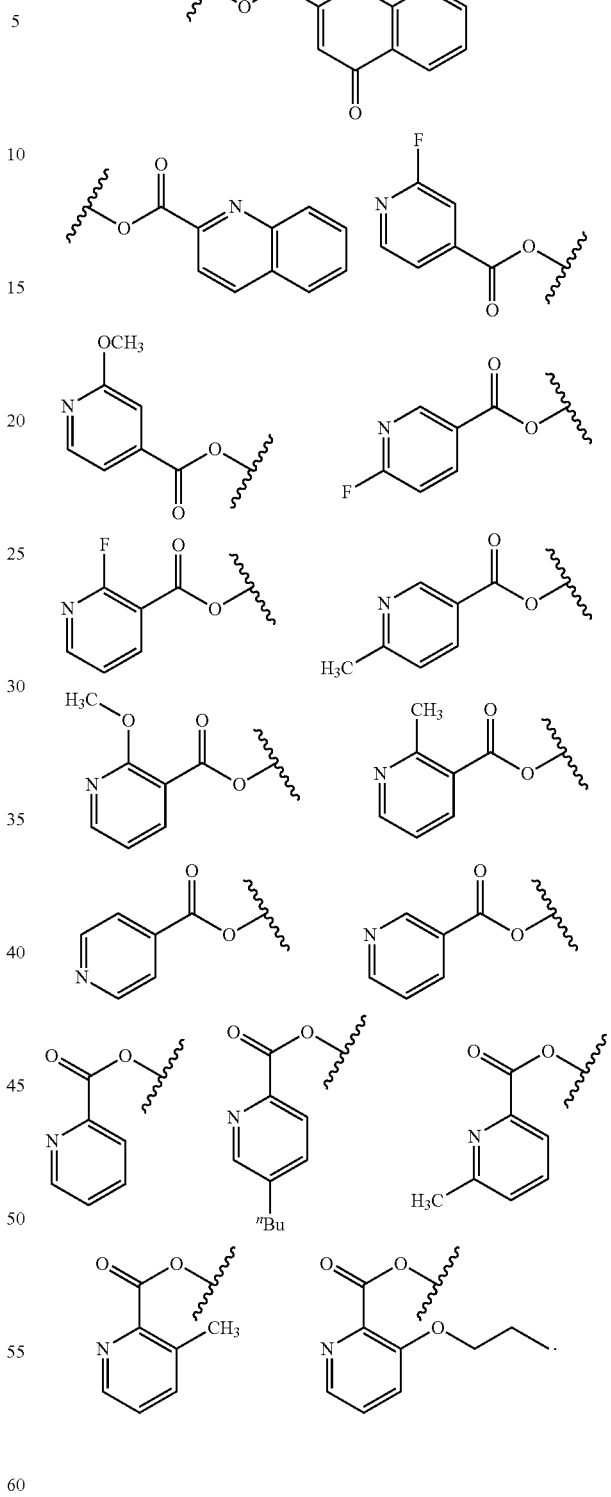
10. The resist composition according to claim 1, wherein the anion moiety of compound (C1) is represented by formula (c1-1) shown below:

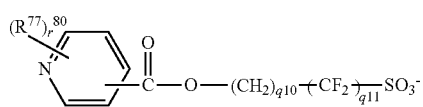
(c1-1)
wherein $q^{10}$ represents an integer of 1 to 9; $q^{11}$ represents an integer of 1 to 9; provided that $q^{10}+q^{11}$ is an integer of 2 to 9; $r^{80}$ represents an integer of 0 to 3; and $R^{77}$ represents a substituent.
11. The compound according to claim 8, wherein, in the formula (c1'), $R^N$—C(=O)—O— represents a group selected from the group consisting of groups shown below:
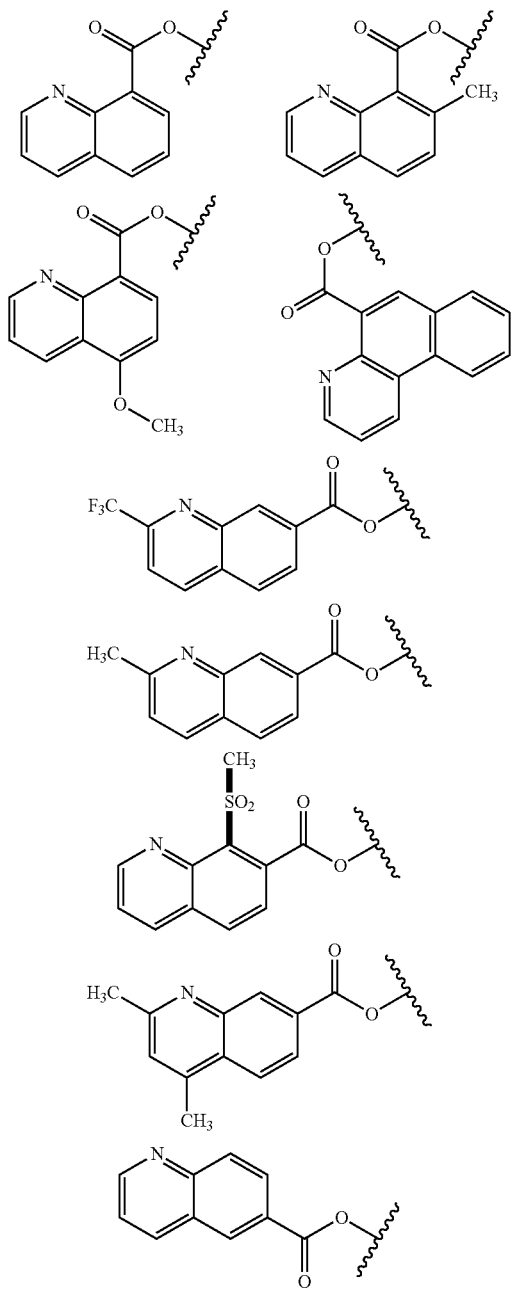
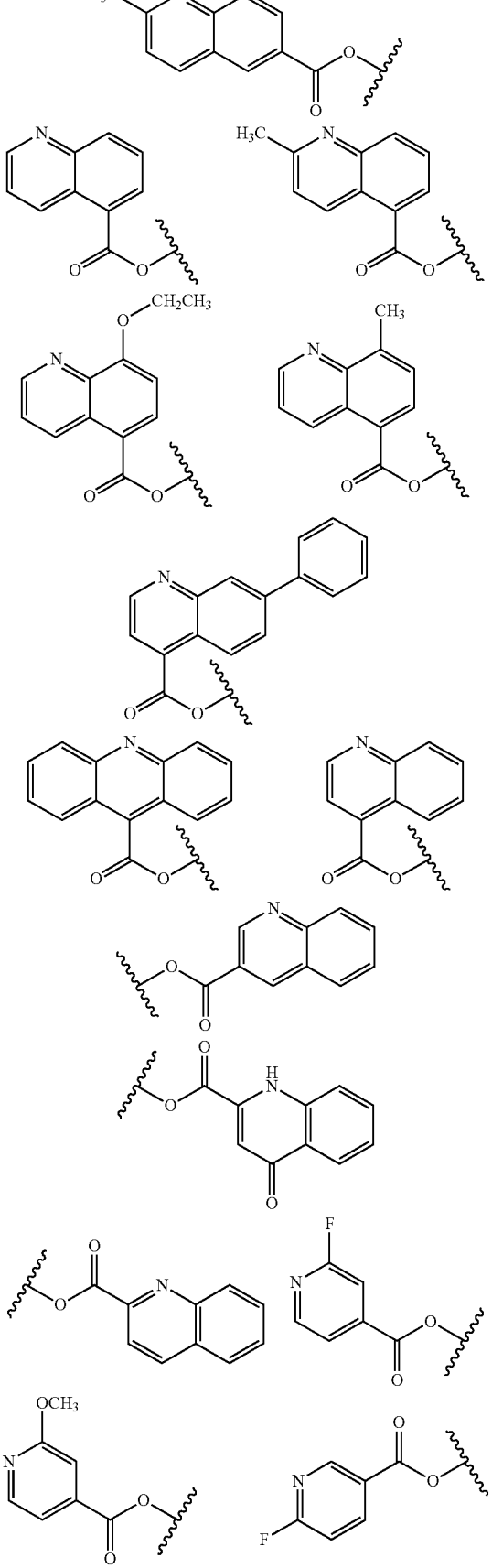

-continued
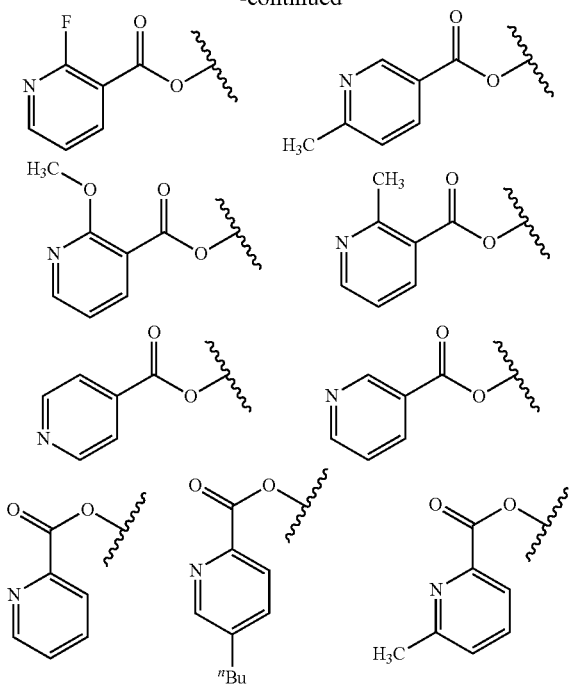
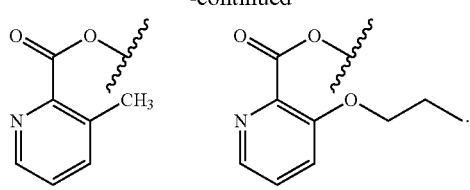
12. The compound according to claim 8, wherein the anion moiety of the compound represented by the formula (c1'-1) is an anion moiety represented by formula (c1-1) shown below:
(c1-1)
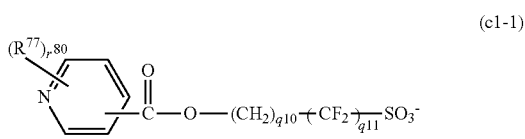
wherein $q^{10}$ represents an integer of 1 to 9; $q^{11}$ represents an integer of 1 to 9; provided that $q^{10}+q^{11}$ is an integer of 2 to 9; $r^{80}$ represents an integer of 0 to 3; and $R^{77}$ represents a substituent.
* * * * *

UNITED STATES PATENT AND TRADEMARK OFFICE
CERTIFICATE OF CORRECTION

PATENT NO.         : 8,846,291 B2
APPLICATION NO.    : 13/312013
DATED              : September 30, 2014
INVENTOR(S)        : Yoshiyuki Utsumi et al.

Page 1 of 2

It is certified that error appears in the above-identified patent and that said Letters Patent is hereby corrected as shown below:

In the Specification

At Column 60, Lines 17-28,

Change " 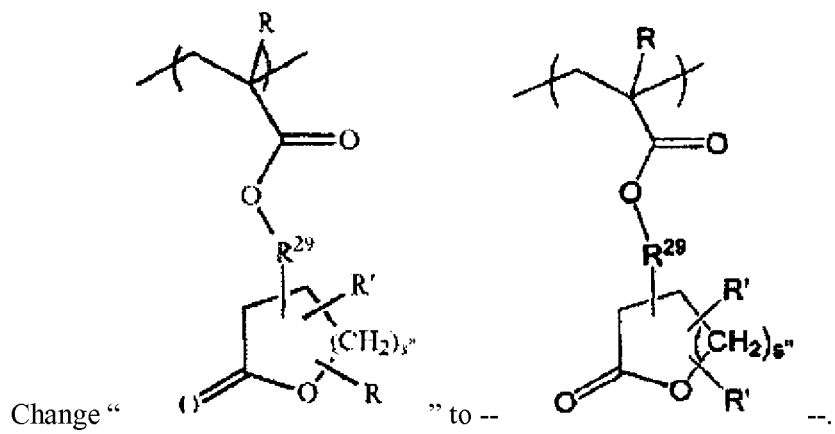 " to -- --.

At Column 74, Line 24, Change "(A 1)" to --(A1)--.

At Column 76, Line 38, Change "(a-4-1)" to --(a4-1)--.

At Column 76, Line 39, Change "(a-4-5)" to --(a4-5)--.

At Column 80, Line 65, After "A'" insert --$R^{24}$,--.

At Column 91, Line 55, Change "q'''" to --$q^{11}$--.

At Column 139, Line 41, Change "(I)" to --(1)--.

At Column 139, Line 41, Change "(I)" to --(1)--.

Signed and Sealed this
Thirtieth Day of June, 2015

Michelle K. Lee
*Director of the United States Patent and Trademark Office*

CERTIFICATE OF CORRECTION (continued)
U.S. Pat. No. 8,846,291 B2

At Columns 149-150, Line 7 (Table 5), Change "norbomane)," to --norbornane),--.

At Columns 149-150, Line 8 (Table 5), Change "norbomane)," to --norbornane),--.

At Columns 149-150, Line 10 (Table 5), Change "norbomane)," to --norbornane),--.

UNITED STATES PATENT AND TRADEMARK OFFICE
CERTIFICATE OF CORRECTION

PATENT NO. : 8,846,291 B2
APPLICATION NO. : 13/312013
DATED : September 30, 2014
INVENTOR(S) : Yoshiyuki Utsumi et al.

It is certified that error appears in the above-identified patent and that said Letters Patent is hereby corrected as shown below:

IN THE SPECIFICATION

At Column 6, Line 3, Change "sulfoneamide" to --sulfonamide--.

At Column 6, Line 8, Change "polycyclolefin" to --polycycloolefin--.

At Column 10, Line 15 (Approx.), Change "(a $1^2$-1)" to --(a1"-1)--.

At Column 10, Line 30 (Approx.), Change "(a $1^2$-2)" to --(a1"-2)--.

At Column 10, Line 42 (Approx.), Change "(a $1^2$-3)" to --(a1"-3)--.

At Column 10, Line 55 (Approx.), Change "(a $1^2$-4)" to --(a1"-4)--.

At Column 11, Line 2 (Approx.), Change "(a $1^2$-5)" to --(a1"-5)--.

At Column 11, Line 17 (Approx.), Change "(a $1^2$-6)" to --(a1"-6)--.

At Column 13, Line 28, Change "(a1-O-1)" to --(a1-0-1)--.

At Column 13, Line 29, Change "(a1-O-2)" to --(a1-0-2)--.

At Column 16, Line 35 (Approx.), Change "(a 1-1)" to --(a1-1)--.

At Column 16, Line 44 (Approx.), Change "(a 1-2)" to --(a1-2)--.

At Column 16, Line 55 (Approx.), Change "(a 1-3)" to --(a1-3)--.

At Column 17, Line 2 (Approx.), Change "(a 1-4)" to --(a1-4)--.

Signed and Sealed this
Twenty-seventh Day of October, 2015

Michelle K. Lee
*Director of the United States Patent and Trademark Office*

CERTIFICATE OF CORRECTION (continued)
U.S. Pat. No. 8,846,291 B2

IN THE SPECIFICATION

At Column 47, Line 4 (Approx.), Change "(a 1-3-02)" to --(a1-3-02)--.